US012049476B2

(12) United States Patent
Isern Amengual et al.

(10) Patent No.: US 12,049,476 B2
(45) Date of Patent: Jul. 30, 2024

(54) PROCESSES FOR THE PREPARATION OF SOLUBLE SALTS OF INOSITOL PHOSPHATES

(71) Applicant: SANIFIT THERAPEUTICS, S.A., Palma de Mallorca (ES)

(72) Inventors: Bernat Isern Amengual, Palma de Mallorca (ES); Marco Antonio Moreno Santurino, Palma de Mallorca (ES); Joan Perelló Bestard, Palma de Mallorca (ES)

(73) Assignee: SANIFIT THERAPEUTICS, S.A., Palma de Mallorca (ES)

( * ) Notice: Subject to any disclaimer, the term of this patent is extended or adjusted under 35 U.S.C. 154(b) by 0 days.

(21) Appl. No.: 18/320,823

(22) Filed: May 19, 2023

(65) Prior Publication Data
US 2023/0340003 A1 Oct. 26, 2023

Related U.S. Application Data

(63) Continuation of application No. PCT/EP2021/085854, filed on Dec. 15, 2021.

(30) Foreign Application Priority Data

Dec. 15, 2020 (EP) .................... 20383092

(51) Int. Cl.
C07H 11/04 (2006.01)
A61K 9/08 (2006.01)
A61K 45/06 (2006.01)
A61K 47/02 (2006.01)
C07H 1/06 (2006.01)

(52) U.S. Cl.
CPC ............... C07H 11/04 (2013.01); A61K 9/08 (2013.01); A61K 45/06 (2013.01); A61K 47/02 (2013.01); C07H 1/06 (2013.01)

(58) Field of Classification Search
None
See application file for complete search history.

(56) References Cited

U.S. PATENT DOCUMENTS

| | | | |
|---|---|---|---|
| 2,718,523 A | 9/1955 | Thomas | |
| 2,750,400 A | 6/1956 | Cowan et al. | |
| 3,159,581 A | 12/1964 | Diehl | |
| 4,024,175 A | 5/1977 | Satzinger et al. | |
| 4,668,813 A | 5/1987 | Ogawa et al. | |
| 5,007,790 A | 4/1991 | Shell | |
| 5,023,248 A * | 6/1991 | Siren | A23L 29/05 514/738 |
| 5,362,886 A | 11/1994 | Berglund | |
| 5,582,837 A | 12/1996 | Shell | |
| 5,972,389 A | 10/1999 | Shell et al. | |
| 6,340,475 B2 | 1/2002 | Shell et al. | |
| 6,451,808 B1 | 9/2002 | Cowles | |
| 6,488,962 B1 | 12/2002 | Berner et al. | |
| 8,377,909 B2 | 2/2013 | Grases Freixedas et al. | |
| 8,778,912 B2 | 7/2014 | Grases Freixedas et al. | |
| 9,358,243 B2 | 6/2016 | Castagner et al. | |
| 9,612,250 B2 | 4/2017 | Perello Bestard et al. | |
| 9,629,872 B2 | 4/2017 | Ratsimbazafy et al. | |
| 2002/0051820 A1 | 5/2002 | Shell et al. | |
| 2003/0039688 A1 | 2/2003 | Shell et al. | |
| 2003/0044466 A1 | 3/2003 | Markey et al. | |
| 2003/0104053 A1 | 6/2003 | Gusler et al. | |
| 2003/0104062 A1 | 6/2003 | Berner et al. | |
| 2003/0147952 A1 | 8/2003 | Lim et al. | |
| 2007/0066574 A1 | 3/2007 | Grases Freixedas | |

FOREIGN PATENT DOCUMENTS

| | | | | |
|---|---|---|---|---|
| CN | 102964381 A | 3/2013 | | |
| CN | 105524106 A | 4/2016 | | |
| JP | 2006342128 A | * 12/2006 | ........... | A61K 31/047 |
| WO | WO-1990011757 A1 | 10/1990 | | |
| WO | WO-1992016534 A1 | 10/1992 | | |
| WO | WO-1993018755 A1 | 9/1993 | | |
| WO | WO-1997047285 A1 | 12/1997 | | |
| WO | WO-1998011879 A1 | 3/1998 | | |
| WO | WO-1998055107 A1 | 12/1998 | | |
| WO | WO-2001032217 A2 | 5/2001 | | |
| WO | WO-2001056544 A2 | 8/2001 | | |

(Continued)

OTHER PUBLICATIONS

Posternak, S. (1921) The synthesis of inositohexaphosphoric acid. Helvetica Chimica Acta, 4, 150-65. (Year: 1921).*
Bhatty, R., et al., "Relationship between phytic acid and cooking quality in lentil," Canadian Institute of Food Science and Technology Journal 22:137-142, Elsevier, Netherlands (Apr. 1989).
Conte, A., et al., "Urinary lithogen risk test: usefulness in the evaluation of renal lithiasis treatment using crystallization inhibitors (citrate and phytate)," Arch. Esp. Urol. 52:305-310, Iniestares, S.A., Spain (Apr. 1999).
Frossard, E., et al., "Potential for increasing the content and bioavailability of Fe, Zn and Ca in plants for human nutrition," J. Sci. Food Agric. 80:861-879, Wiley, United States (May 2000).
Grases Freixedas., et al., "Variation of InsP(4),InsP(5) and InsP(6) levels in tissues and biological fluids depending on dietary phytate," J. Nutr. Chem. 12:595-601, Elsevier, Netherlands (Oct. 2001).
Grases Freixedas., et al., "Phytate (IP6) is a powerful agent for preventing calcifications in biological fluids: usefulness in renal lithiasis treatment," Anticancer Res. 19:3717-3722, International Institute of Anticancer Research, Greece (Sep. 1999).

(Continued)

Primary Examiner — Dale R Miller
(74) Attorney, Agent, or Firm — STERNE, KESSLER, GOLDSTEIN & FOX P.L.L.C.

(57) ABSTRACT

The present invention provides processes for preparing soluble salts of inositol phosphate characterized by a low level of impurities. Processes for preparing soluble salts (e.g., alkali-metal or ammonium) of inositol phosphates (e.g., hexasodium or dodecasodium salts), and of inositol hexaphosphate in particular (e.g., $Na_6IP_6$ and $Na_{12}IP_6$), are described. Also provided are pharmaceutical compositions, methods of use, combination treatments, kits, and articles of manufacture comprising soluble salts of inositol phosphates prepared according to the method of the invention.

30 Claims, 19 Drawing Sheets

(56) References Cited

FOREIGN PATENT DOCUMENTS

| WO | WO-2001097783 A1 | 12/2001 |
|---|---|---|
| WO | WO-2002032416 A2 | 4/2002 |
| WO | WO-2002096404 A1 | 12/2002 |
| WO | WO-200335029 A1 | 5/2003 |
| WO | WO-200335040 A1 | 5/2003 |
| WO | WO-200335041 A1 | 5/2003 |
| WO | WO-2003035039 A1 | 5/2003 |
| WO | WO-2003035177 A2 | 5/2003 |
| WO | WO-2017098033 A1 | 6/2017 |
| WO | WO-2017098047 A1 | 6/2017 |
| WO | WO-2017131127 A1 | 8/2017 |
| WO | WO-2022129148 A1 | 6/2022 |

OTHER PUBLICATIONS

Grases Freixedas., et al., "Phytate (Myo-inositol hexakisphosphate) inhibits cardiovascular calcifications in rats," Front. Biosci. 11:136-42, IMR Press Limited, Singapore (Jan. 2006).

Harland, B., et al., "A Modified Method for Phytate Analysis Using an Ion-Exchange Procedure: Application to Textured Vegetable Proteins.," Cereal Chem. 54:827-32, John Wiley & Sons Inc., United States (Jan. 1977).

Haynes, D., et al., "Occurrence of pharmaceutically acceptable anions and cations in the Cambridge Structural Database," J. Pharmaceutical Sci. 94:2111-2120, Elsevier, Netherlands (Oct. 2005).

International Search Report and Written Opinion for International Application No. PCT/EP2021/085854, European Patent Office, Netherlands, mailed on Feb. 28, 2022, 6 pages.

Kreimeyer, I., et al., "Autoproteolytic cleavage mediates cytotoxicity of *Clostridium difficile* toxin A," Naunyn Schmiedebergs Arch Pharmacol. 383(3):253-262, Springer, Germany (Mar. 2011).

Madsen, C.K., et al., "Lab-scale preparation and QC of phytase assay substrate from rice bran," Analytical Biochemistry 578:7-12, Elsevier, Netherlands (Aug. 2019).

Perelló, J., et al., "SNF472, a novel inhibitor of vascular calcification, could be administered during hemodialysis to attain potentially therapeutic phytate levels," Journal of Nephrology 31(2):287-296, American Society of Nephrology, United States (Jan. 2018).

Ruyter-Hooley, M., et al., "Surface complexation modeling of inositol hexaphosphate sorption onto gibbsite," Journal of Colloid and Interface Science 440(15):282-291, Elsevier, Netherlands (Feb. 2015).

Schlemmer, U., et al., "Phytate in foods and significance for humans: food sources, intake, processing, bioavailability, protective role and analysis," Mol. Nutr. Food Res. 53:S330-S375, Wiley-Blackwell, United States (Sep. 2009).

Summary of Clinical Trial List, Search of NCT02790073, ClinicalTrials.gov, accessed at https://clinicaltrials.gov/study/NCT02790073?term=NCT02790073&rank=1, accessed on Oct. 2, 2023, 9 pages.

Summary of Clinical Trial List, Search of NCT02966028, ClinicalTrials.gov, accessed at https://clinicaltrials.gov/study/NCT02966028?term=NCT02966028&rank=1, accessed on Oct. 2, 2023, 15 pages.

Yoshida, K., et al., "Temporal and spatial patterns of accumulation of the transcript of Myo-inositol-1-phosphate synthase and phytin-containing particles during seed development in rice," Plant Physiol. 119:65-72, American Society of Plant Biologists, United States (Jan. 1999).

* cited by examiner

OP = phosphate moeity

PROCESSES FOR THE PREPARATION OF SOLUBLE SALTS OF INOSITOL PHOSPHATES

CROSS-REFERENCE TO RELATED APPLICATIONS

The present application is a continuation of International Application No. PCT/EP2021/085854, filed Dec. 15, 2021, which claims the priority of European Patent Application No., EP20383092.2, filed Dec. 15, 2020, both of which are herein incorporated by reference in their entireties.

FIELD OF THE INVENTION

The present invention relates to processes for preparing soluble salts of inositol phosphates, the compounds obtained thereby, compositions containing the compounds, and methods of using the compounds and compositions for treating ectopic calcifications in human health.

BACKGROUND ART

Inositol hexaphosphate ($IP_6$, phytic acid, phytate) is a potent inhibitor of the crystallization of calcium salts (Grases F, et al., Anticancer Res. 1999; 19:3717-3722). As it is a molecule with six phosphate groups, it shows a high affinity for divalent and trivalent metallic ions such as calcium. This property allows $IP_6$ preventing the development of pathological calcifications, such as renal lithiasis (Conte A, et al., Arch. Esp. Urol. 1999; 52:305-310) or cardiovascular calcifications (Grases F, et al., Front. Biosci. 2006; 11:136-42), among others. This property also allows it to chelate calcium ions in environments such as the intestinal tract, where it can prevent or treat *Clostridium difficile* infections (Kreimeyer I, et al., Naunyn Schmiedebergs Arch Pharmacol. 2011; 383(3):253-262.

$IP_6$ is a molecule abundant in vegetable seeds and legumes. Between 1.5% and 6.4% of the dry weight of grains consists of $IP_6$ (Reddy N, Sathe S, Eds., Food phytates (CRC, Boca Raton, FL, USA, 2002); Schlemmer U, et al., Mol. Nutr. Food Res. 2009; 53:S330-S375)). It may also be found in all organs and tissues of animals in ionized form (Grases F, et al., J. Nutr. Chem. 2001; 12:595-601). Most of the $IP_6$ currently used is of vegetable origin.

In the plant and seed tissues, $IP_6$ is naturally present as a mixture of K, Mg, Ca, Mn, Zn and Fe salts of $IP_6$ (Frossard E, et al., J. Sci. Food Agric. 2000; 80:861-887). The most abundant $IP_6$ salt is its Ca—Mg salt also known as phytin (Bhatty R, et al., Can. Inst. Food Sci. Tech. J. 1989; 22:137-142; Yoshida K, et al., Plant Physiol. 1999; 119:65-72). However, phytin is insoluble in water and is thus inadequate for preparing aqueous solutions for intravenous administration.

The $IP_6$ commercially available is obtained mainly from raw materials such as rice bran or corn steep liquor. These materials are treated with organic or inorganic acids to extract phytin, which is then precipitated and separated from the extract, usually by filtration, to remove any unwanted proteins and carbohydrates. Afterwards, phytin is hydrolyzed under pressure to recover $IP_6$. Various methods based on the use of ionic exchange columns for extracting $IP_6$ and its salts have been described in the art (Harland B, et al., Cereal Chem. 1977; 54:827-32). See also, U.S. Pat. No. 2,718,523 describing the preparation of phytic acid and soluble salts thereof by cation exchange; U.S. Pat. No. 2,750,400 describing the preparation of phytic acid from calcium magnesium phytates using cation exchange; and U.S. Pat. No. 4,668,813 describing the preparation of phytin using anion exchange followed by alkali elution. In addition, CN102964381 describes the purification of $IP_6$ by an ethanol crystallization process; and WO1992016534 describes a process for the direct purification of phytate using a solid-phase free base polymer having tertiary amine functions.

$IP_6$ and its salts have many therapeutic applications. For instance, calcium phytate is used as calcium enrichment, while sodium phytate is used for the prevention of the relapse of calculosis, and potassium phytate is used for the treatment of hypercalcemia. More recently, the hexasodium salt of $IP_6$ ($Na_6IP_6$) has been employed for reducing or preventing pathological calcification (FIG. 1), e.g., as a drug substance in the preparation formulations indicated for treating calciphylaxis (CUA). See Clinical Trail NCT02790073 (Phase 2 Study with SNF472 in Calciphylaxis Patients) at https://clinicaltrials.gov/, December 2020.

$Na_6IP_6$ has also been used in formulations indicated for reducing cardiovascular events related to cardiovascular calcification (CVC) in patients with end stage renal disease (ESRD) undergoing hemodialysis (HD). See Clinical Trail NCT02966028 (Effect of SNF472 on Progression of Cardiovascular Calcification in End-Stage-Renal-Disease (ESRD) Patients on Hemodialysis (HD)) at https://clinicaltrials.gov/, December 2020.

Thus, there is present need in the art for soluble salts of inositol phosphate (e.g., $Na_6IP_6$) having a high degree of purity and for processes for its preparation thereof which are industrially scalable, reproducible, and safe.

SUMMARY OF THE INVENTION

The present invention provides a process for purifying (i.e., recrystallizing) an inositol phosphate (IP) salt, the process comprising the steps of (i) dissolving the IP salt in water to obtain an IP solution, (ii) converting the IP solution to an IP suspension, (iii) washing the IP suspension with an alcohol solution to obtain a solid, and (iv) drying the solid to obtain the purified (i.e., recrystallized) IP salt.

In some aspects, the IP salt and water of step (i) are mixed in a 1:2 weight ratio. In some aspects, the IP solution of step (i) is heated. In some aspects, the IP solution is heated at about 45° C. to about 50° C. In some aspects, the IP solution is heated for about 4 hours or less. In some aspects, the IP solution is heated for about 2 hours or less. In some aspects, the IP solution is filtered. In some aspects, the IP solution is seeded with crystals of the IP salt previously recrystallized. In some aspects, the IP solution is seeded with crystals of the IP salt previously recrystallized representing about 0.4% (w/w) or less of the IP salt of step (i). In some aspects, the IP solution is seeded with crystals of the IP salt previously recrystallized representing about 0.2% (w/w) or less of the IP salt of step (i). In some aspects, the IP solution is seeded with crystals of the IP salt previously recrystallized representing about 0.1% (w/w) or less of the IP salt of step (i).

In some aspects, the IP solution is stirred. In some aspects, the alcohol solution in step (iii) comprises, consists or consists essentially of a $C_1$-$C_4$ alcohol. In some aspects, the $C_1$-$C_4$ alcohol is ethanol. In some aspects, the drying of the solid of step (iv) is conducted at about 50° C. or less.

The present invention also provides a process for preparing a soluble salt of an inositol phosphate (IP), the process comprising the steps of (a) dissolving an IP salt in water to obtain an IP solution, (b) contacting the IP solution with an ion exchange medium, (c) concentrating the ion exchanged IP solution from step (b) to obtain an IP syrup, and (d) separating the soluble IP salt from the IP syrup in the presence of an alkoxide.

In some aspects, the present invention provides a process for preparing a purified soluble salt of an inositol phosphate (IP), the process comprising the steps of (a) dissolving a purified (i.e., recrystallized) IP salt in water to obtain an IP solution, (b) contacting the IP solution with an ion exchange medium, (c) concentrating the ion exchanged IP solution from step (b) to obtain an IP syrup, and (d) separating the purified soluble IP salt from the IP syrup in the presence of an alkoxide.

In some further aspects, the present invention also provides a process for preparing an unpurified soluble salt of an inositol phosphate (IP), the process comprising the steps of (a) dissolving an unpurified IP salt in water to obtain an IP solution, (b) contacting the IP solution with an ion exchange medium, (c) concentrating the ion exchanged IP solution from step (b) to obtain an IP syrup, and (d) separating the unpurified soluble IP salt from the IP syrup in the presence of an alkoxide.

In some aspects, the present invention provides a process for preparing a purified soluble salt of an inositol phosphate (IP), the process comprising the steps of (i) dissolving an IP salt in water to obtain a first IP solution, (ii) converting the first IP solution to an IP suspension, (iii) washing the IP suspension with an alcohol solution to obtain an IP solid, (iv) dissolving the IP solid in water to obtain a second IP solution, (v) contacting the second IP solution with an ion exchange medium, (vi) concentrating the ion exchanged IP solution from step (v) to obtain an IP syrup, and (vii) separating the purified soluble IP salt from the IP syrup in the presence of an alkoxide. See General Scheme 1. In some aspects, the purified soluble IP salt of step (vii) is dried. In some further aspects, the purified soluble IP salt of step (vii) is spray-dried.

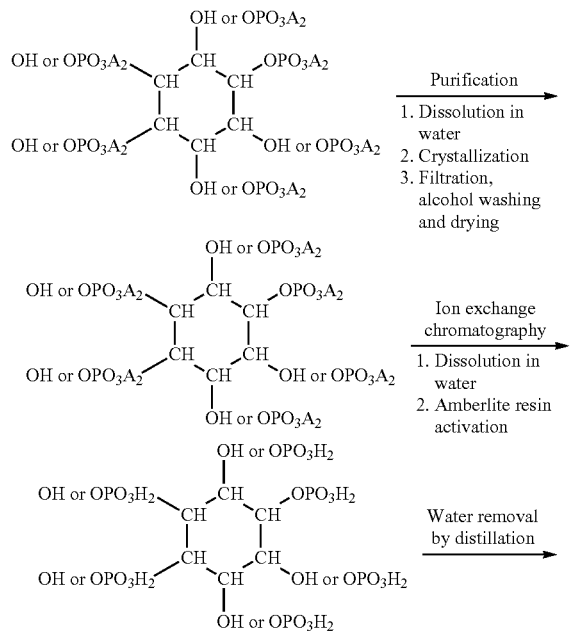

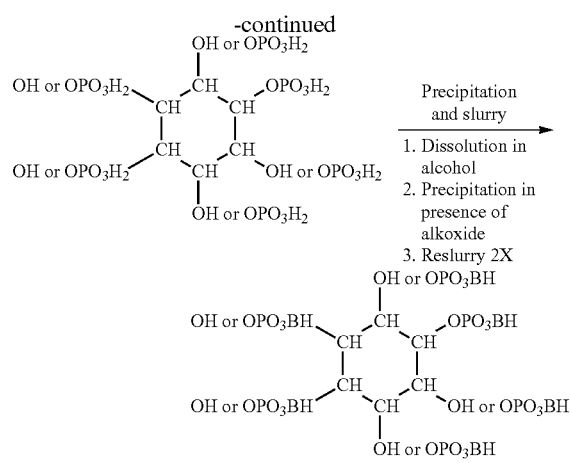

Wherein A is a monovalent cation such as an alkali cation (e.g., $Na^+$, $K^+$), ammonium (i.e., $NH4^+$) or a combination thereof. In some aspects, the cation of the end product B may be the same (i.e., A=B) or different from the cation of the starting material (e.g., a potassium IP salt is used as starting material and is treated with a sodium alkoxide to yield a sodium end product, See Example 13).

In some aspects, the ion exchange medium is an ion exchange chromatography, batch process or pH adjustment system. In some aspects, step (c) is conducted by distilling the IP solution at about 55° C. or less.

In some aspects, the alkoxide is a $C_1$-$C_4$ alkoxide. In some aspects, the $C_1$-$C_4$ alkoxide is $CH_3NaO$, $CH_3CH_2NaO$, $CH_3KO$ or $CH_3CH_2KO$. In some aspects, step (d) is conducted between about pH 4.0 and about pH 5.5. In some aspects, the process further comprises (e) spray drying the soluble IP salt of step (d). In some aspects, the soluble IP salt of step (a) has been previously recrystallized according to a recrystallization process disclosed herein. In some aspects, the soluble IP salt of step (e) is further recrystallized according to a recrystallization process disclosed herein.

In some aspects of the processes disclosed herein, the IP contains between 1 and 8 phosphate groups. In some aspects, the IP contains between 1 and 6 phosphate groups. In some aspects, the IP is inositol hexaphosphate. In some aspects, the inositol hexaphosphate is myo-inositol hexaphosphate. In some aspects, the IP salt contains at least one monovalent cation. In some aspects, the monovalent cation is (i) a Group 1 alkali metal element cation, (ii) ammonium or (iii) a combination thereof. In some aspects, the Group 1 alkali metal element is sodium, potassium or a combination thereof.

The present invention also provides a purified soluble IP salt obtained according to any of the processes disclosed herein. In some aspects, the purified soluble IP salt is a monovalent cationic salt of inositol monophosphate ($IP_1$), inositol biphosphate ($IP_2$), inositol triphosphate ($IP_3$), inositol tetrakisphosphate ($IP_4$), inositol pentaphosphate ($IP_5$), inositol hexaphosphate ($IP_6$) or a combination thereof. In some aspects, the purified soluble IP salt is at least 70% (w/w), at least 75% (w/w), at least 80% (w/w), at least 85% (w/w), at least 90% (w/w) or at least 95% (w/w) pure.

In some aspects, the purified soluble IP salt is a monovalent cationic salt of $IP_6$ (e.g., $Na_5IP_6$, $Na_6IP_6$, $K_4IP_6$, $K_6IP_6$, $(NH_4)_6IP_6$). In some aspects, the purified soluble IP salt is $Na_6IP_6$. Accordingly, the present invention also provides an $IP_6$ salt, for example hexasodium salt, that is at least 70% (w/w) pure comprising (i) DL-Inositol 1,2,3,4,6-pentaphosphate≤2.0% (w/w), (ii) DL-Inositol 1,2,3,5,6-pentaphosphate≤4.0% (w/w), (iii) DL-Inositol 1,2,4,5,6-pentaphosphate≤5.0% (w/w), and, (iv) DL-Inositol 1,3,4,5,6-pentaphosphate≤3.0% (w/w). Also provided is a $Na_6IP_6$ salt that is at least 80% (w/w) pure comprising (i) DL-Inositol 1,2,3,4,6-pentaphosphate≤1.4% (w/w), (ii) DL-Inositol 1,2,3,5,6-pentaphosphate≤2.1% (w/w), (iii) DL-Inositol 1,2,4,5,6-pentaphosphate≤2.6% (w/w), and (iv) DL-Inositol 1,3,4,5,6-pentaphosphate≤0.52% (w/w).

The present invention also provides pharmaceutical compositions comprising IP salts prepared according to the methods disclosed herein, e.g., the $Na_6IP_6$ salt, and combinations thereof. In some aspects, the pharmaceutical composition is injectable. In some aspects, the pharmaceutical composition is administered parenterally. In some aspects, the parenteral administration is intravenous. In some aspects, the intravenous administration is via intravenous infusion. In some aspects, the pharmaceutical compositions comprising the IP salts prepared according to the methods disclosed herein are stable at room temperature (i.e., 25° C., 60% RH) for at least 6 months.

The present invention also provides combination treatments comprising a compound prepared according to the process of any one of claims, a purified soluble IP salt prepared according to the methods disclosed herein (e.g., $Na_6IP_6$, $K_6IP_6$, $(NH_4)_6IP_6$)) or a pharmaceutical composition disclosed herein in combination with one of more (e.g., a second or a third) therapeutic agent and/or treatment disclosed in Table 1.

Also provided is a kit or product of manufacture comprising (i) a compound prepared according to the process of any one of claims, a purified soluble IP salt prepared according to the methods disclosed herein (e.g., $Na_6IP_6$, $Na_5IP_6$, $K_4IP_6$, $K_6IP_6$, $(NH_4)_6IP_6$), a pharmaceutical composition disclosed herein or a combination treatment disclosed herein, and (ii) instructions for administration.

The present invention also provides methods for treating or preventing ectopic calcification or its consequences in a subject in need thereof which comprises administering a compound prepared according to the process of any one of claims, a soluble IP salt prepared according to the methods disclosed herein (e.g., $Na_6IP_6$), a pharmaceutical composition disclosed herein, a combination treatment disclosed herein or a kit disclosed herein to the subject. Alternatively, the present invention provides a compound prepared according to the process of any one of claims, a soluble IP salt prepared according to the methods disclosed herein (e.g., $Na_6IP_6$), a pharmaceutical composition disclosed herein, a combination treatment disclosed herein or a kit disclosed for use in the treatment or prevention of ectopic calcification or its consequences in a subject in need thereof. Alternatively, the present invention provides the use of a compound prepared according to the process of any one of claims, a soluble IP salt prepared according to the methods disclosed herein (e.g., $Na_6IP_6$), a pharmaceutical composition disclosed herein, a combination treatment disclosed herein or a kit disclosed herein in the preparation of a medicament for treating or preventing ectopic calcification or its consequences in a subject in need thereof. In some aspects, the subject is undergoing hemodialysis. In some aspects, the subject has end-stage renal disease.

DETAILED DESCRIPTION OF THE INVENTION

Figure 1:
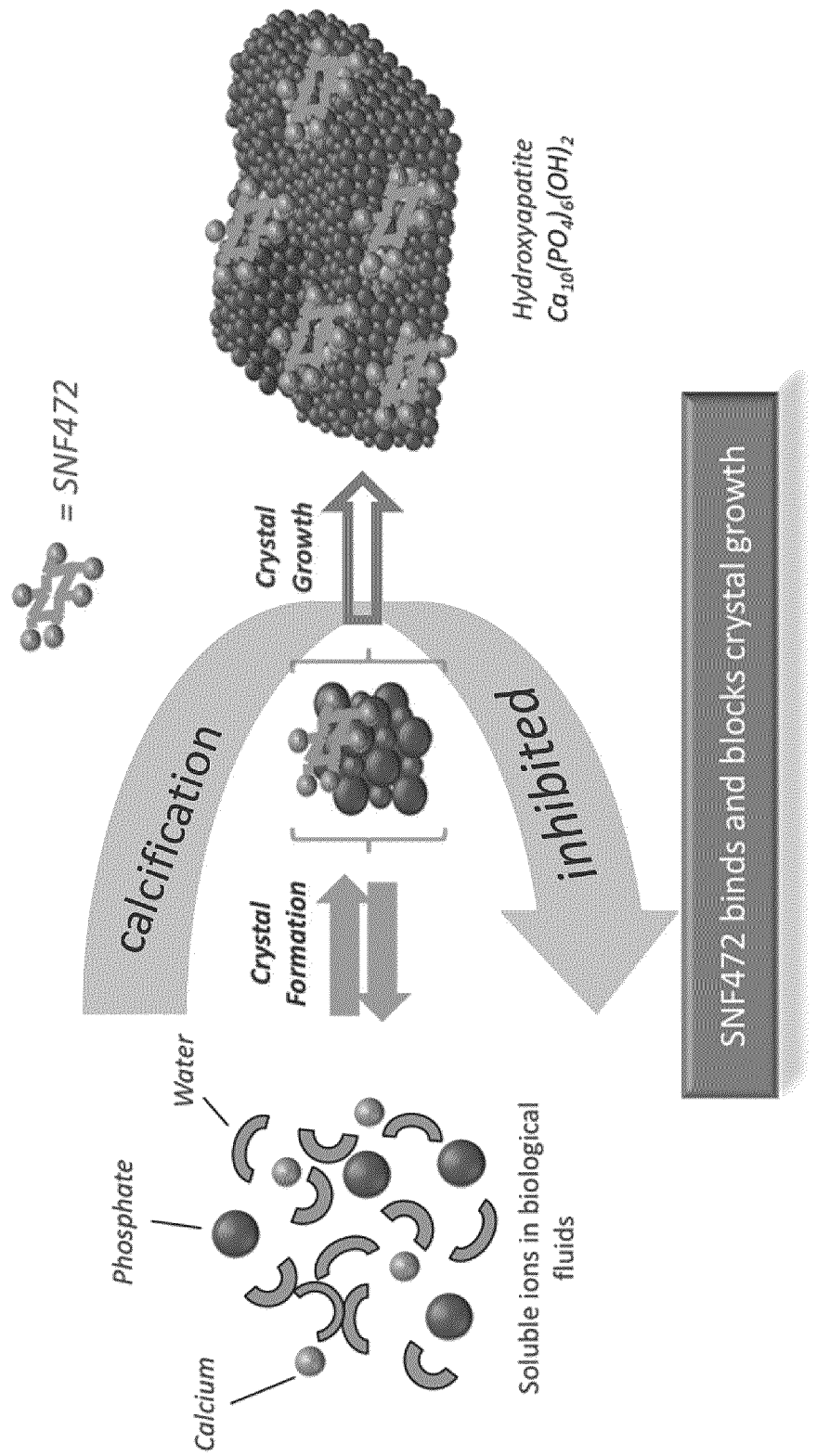
FIG. 1 shows a schematic representation of the proposed mechanism of action of $Na_6IP_6$ (SNF472) to prevent calcification by binding to nascent crystals and therefore preventing crystal growth.

The present invention relates to processes for preparing soluble salts of inositol phosphate characterized by a low level of impurities. In some aspects, the inositol phosphate salt contains at least one monovalent cation. In some aspects, the monovalent cation is (i) a Group 1 alkali metal element cation, (ii) ammonium or (iii) a combination thereof. In some aspects, the Group 1 alkali metal element is sodium, potassium or a combination thereof. In some further aspects, the preparation of several soluble salts of inositol hexaphosphate (e.g., $Na_6IP_6$, $Na_5IP_6$, $K_4IP_6$, $K_6IP_6$, $(NH_4)_6IP_6$)) are described. In some aspects, the invention provides processes for the preparation of the hexasodium salt of inositol hexaphosphate ($Na_6IP_6$) from its dodecasodium salt ($Na_{12}IP_6$), as well as processes for the preparation of the $Na_{12}IP_6$ intermediate (e.g., via recrystallization). The $Na_6IP_6$ compound can be used as drug substance in the SNF472 product. This product has undergone phase II clinical trials (See e.g., clinical trial NCT02790073) and is currently in phase III clinical trials.

The present invention also provides compositions, e.g., pharmaceutical compositions, comprising phytate salts (e.g., $Na_6IP_6$, $Na_5IP_6$, $K_4IP_6$, $K_6IP_6$, $(NH_4)_6IP_6$)) prepared according to the methods of the present invention. Also provided are formulations, articles of manufacture, and kits comprising phytate salts (e.g., $Na_6IP_6$, $Na_5IP_6$, $K_4IP_6$, $K_6IP_6$, $(NH_4)_6IP_6$)) prepared according to the methods of the present invention. Also provided are methods of treatment comprising the administration of phytate salts (e.g., $Na_6IP_6$, $Na_5IP_6$, $K_4IP_6$, $K_6IP_6$, $(NH_4)_6IP_6$)) prepared according to the methods of the present invention to a patient in need thereof, e.g., a subject suffering from a disease or condition disclosed herein such as calciphylaxis or cardiovascular calcification.

The invention also provides dosage forms comprising an amount of phytate salts (e.g., $Na_6IP_6$, $Na_5IP_6$, $K_4IP_6$, $K_6IP_6$, $(NH_4)_6IP_6$)) prepared according to the methods of the present invention.

The present application also discloses phytate salts (e.g., $Na_6IP_6$, $Na_5IP_6$, $K_4IP_6$, $K_6IP_6$, $(NH_4)_6IP_6$)) prepared according to the methods of the present invention for use as a medicament. Also provided are uses of the phytate salts (e.g., $Na_6IP_6$, $Na_5IP_6$, $K_4IP_6$, $K_6IP_6$, $(NH_4)_6IP_6$)) prepared according to the methods of the present invention for use in the treatment of a disease or condition disclosed herein, e.g., ectopic calcifications such as calciphylaxis or cardiovascular calcification. Also disclosed is the use of phytate salts (e.g., $Na_6IP_6$, $Na_5IP_6$, $K_4IP_6$, $K_6IP_6$, $(NH_4)_6IP_6$)) prepared according to the methods of the present invention in the manufacture of a medicament for the treatment of a disease or condition disclosed herein, e.g., calciphylaxis or cardiovascular calcification.

In order that the present invention can be more readily understood, certain terms are first defined below. As used in this application, except as otherwise expressly provided herein, each of the following terms shall have the meaning set forth below. Additional definitions are set forth throughout the application.

1. Definitions of General Terms and Expressions

The invention includes aspects in which exactly one member of the group is present in, employed in, or otherwise relevant to a given product or process. The invention includes aspects in which more than one, or all the group members are present in, employed in, or otherwise relevant to a given product or process.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd Ed. (CRC Press, Boca Raton, FL, USA, 2002); The Dictionary of Cell and Molecular Biology, 3rd Ed. (Academic Press, London, U K, 1999); and the Oxford Dictionary of Biochemistry and Molecular Biology, Revised, (Oxford University Press, Oxford, U K, 2000), provide one of skill with a general dictionary of many of the terms used in this invention.

Units, prefixes, and symbols are denoted in their Systeme International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention.

Where a value is explicitly recited, it is to be understood that values which are about the same quantity or amount as the recited value are also within the scope of the invention. Where a combination is disclosed, each sub-combination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

About: The term "about" as used herein to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 20%. Furthermore, particularly with respect to biological systems or processes, the terms can mean up to an order of magnitude or up to 5-fold of a value.

When particular values or compositions are provided in the application and claims, unless otherwise stated, the meaning of "about" should be assumed to be within an acceptable error range for that particular value or composition. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

And/or: "And/or" where used herein is to be taken as specific invention of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Approximately: As used herein, the term "approximately," as applied to one or more values of interest, refers to a value that is similar to a stated reference value. In certain aspects, the term "approximately" refers to a range of values that fall within 10%, 9%, 8%, 7%, 6%, 5%, 4%, 3%, 2%, 1% or less in either direction (greater than or less than) of the stated reference value unless otherwise stated or otherwise evident from the context (except where such number would exceed 100% of a possible value).

Comprising: It is understood that wherever aspects are described herein with the language "comprising," otherwise analogous aspects described in terms of "consisting of" and/or "consisting essentially of" are also provided.

Compound: As used herein, the term "compound," is meant to include all isomers and isotopes of the structures depicted. As used herein, the term "isomer" means any geometric isomer, tautomer, zwitterion, stereoisomer, enantiomer or diastereomer of a compound. Compounds can include one or more chiral centers and/or double bonds and can thus exist as stereoisomers, such as double-bond isomers (i.e., geometric E/Z isomers) or diastereomers (e.g., enantiomers (i.e., (+) or (−)) or cis/trans isomers). The present invention encompasses any and all isomers of the compounds described herein, including stereomerically pure forms (e.g., geometrically pure, enantiomerically pure or diastereomerically pure) and enantiomeric and stereoisomeric mixtures, e.g., racemates. Enantiomeric and stereomeric mixtures of compounds and means of resolving them into their component enantiomers or stereoisomers are well-known. A compound, salt or complex of the present invention can be prepared in combination with solvent or water molecules to form solvates and hydrates by routine methods. In some aspects, the term compound is used to refer to a salt of inositol hexaphosphate (e.g., $Na_6IP_6$ or $Na_{12}IP_6$) of the present invention.

Inositol phosphate: As used herein, the term "inositol phosphate" (and grammatical variants thereof) refers to a compound with an inositol ring and one, two, three, four, five or six phosphate groups (i.e., $IP_1$, $IP_2$, $IP_3$, $IP_4$, $IP_5$, $IP_6$) or a combination thereof. The inositol phosphate may also include 7 or 8 phosphate groups (e.g., by attaching an additional phosphate group to a phosphate group already linked to the inositol ring). Myo-inositol hexaphosphate is an exemplary inositol hexaphosphate ($IP_6$) of the present invention. In some aspects, the inositol phosphate is pure (e.g., over 99% of the inositol phosphate species are the same species, for example, $IP_6$) or substantially pure (e.g., at least 90%, 91%, 92%, 93%, 94%, 95%, 96%, 97%, 98% or 99% of the inositol phosphate species are the same species, for example, $IP_6$). In some aspects, the inositol phosphate is a mixture, e.g., comprising variable amounts of $IP_1$, $IP_2$, $IP_3$, $IP_4$, $IP_5$, $IP_6$, $IP_7$, and IPs. In some aspects, the inositol phosphate is a racemic mixture.

Inositol phosphate analog: A used herein, the term "inositol phosphate analog" (and grammatical variants thereof) refers to a compound that has a ring with different number of carbons with respect to an inositol ring (i.e., 5 or 7 carbons), and/or has at least one sulfate or thiophosphate group. For example, a compound comprising a ring with 5, 6 or 7 carbons and at least one phosphate, sulfate or thiophosphate group would be considered an inositol phosphate analog.

Inositol phosphate derivative: As used herein, the term "inositol phosphate derivative" (and grammatical variants thereof) refers to an "inositol phosphate" or "inositol phosphate analog" which has been derivatized with a heterologous moiety (i.e., a group that is not a phosphate, a sulfate or a thiophosphate). For example, an inositol pentasulfate comprising a heterologous moiety (e.g., PEG) would be considered inositol phosphate derivative.

Heterologous moiety: A used herein, the term "heterologous moiety" (and grammatical variants thereof) refers to a group or substituent in an inositol phosphate derivative which is not a phosphate, a sulfate or a thiophosphate, and confers a desirable property to such compound. For example, a heterologous moiety (e.g., a polyglycerol or a polyethyleneglycol) can increase the solubility of the compound. In some aspects, a heterologous moiety can confer multiple desirable properties, e.g., polyglycerol and polyethyleneglycol can both increase the solubility of a compound and reduce the clearance rate of the compound.

In some aspects, the inositol phosphate is an inositol phosphate, variant or derivative thereof disclosed in PCT/IB2018/057904, which describes compounds encompassed by formula I below.

$Na_6IP_6$: The term "$Na_6IP_6$" refers to the hexasodium salt of inositol hexaphosphate. In some aspects, $Na_6IP_6$ is a hexasodium salt of myo-inositol hexaphosphate.

$Na_{12}IP_6$: The term "$Na_{12}IP_6$" as used herein refers to the dodecasodium salt of inositol hexaphosphate. In some aspects, $Na_{12}IP_6$ is a dodecasodium salt of myo-inositol hexaphosphate.

Ph. Eur. 2.2.3.: The term "Ph. Eur. 2.2.3." as used herein, refers to the "Potentiometric Determination of pH" measurement protocol [European Pharmacopeia 10.0, December 2020].

Ranges: As described herein, any concentration range, percentage range, ratio range or integer range is to be understood to include the value of any integer within the recited range and, when appropriate, fractions thereof (such as one tenth and one hundredth of an integer), unless otherwise indicated.

Salt of inositol hexaphosphate: The terms "salt of inositol hexaphosphate disclosed herein" and "salt of inositol hexaphosphate of the present invention," and grammatical variants thereof refers to a salt of inositol hexaphosphate (e.g., $Na_6IP_6$ or $Na_{12}IP_6$ or a combination thereof), prepared according to the methods disclosed herein. In some aspects, the salt is a sodium salt. In other aspects, the salt is a potassium salt (e.g., $K_6IP_6$ or $K_{12}IP_6$ or a combination thereof), prepared according to the methods disclosed herein. In other aspects, the salt is an ammonium salt (e.g., $(NH_4)_6IP_6$ or $(NH_4)_{12}IP_6$ or a combination thereof), prepared according to the methods disclosed herein. In some aspects, the salt of inositol hexaphosphate disclosed herein is $Na_6IP_6$ or $Na_{12}IP_6$ prepared according to the methods disclosed herein.

SNF472: As used herein, the term "SNF472" refers to an intravenous myo-inositol hexaphosphate formulation, e.g., a salt of inositol hexaphosphate (e.g., $Na_6IP_6$) disclosed herein. SNF472 is prepared at three different strengths: (i) 20 mg/mL in 5 mL single-use vials, (ii) 30 mg/mL in 5 mL and 10 mL single-use vials, and (iii) 90 mg/mL in 5 mL and 10 mL single-use vials. The product is formulated in a saline solution having a pH of about 5.6 to about 6.4.

Soluble: As used herein, the terms "soluble" and "solubility" refers to the degree to which a salt of an inositol phosphate dissolves in water to make an aqueous solution. A salt of an inositol phosphate (e.g., $Na_6IP_6$, $Na_5IP_6$, $K_4IP_6$, $K_6IP_6$, $(NH_4)_6IP_6$)) is considered soluble in water provided that 1 g of the substance is dissolved in 10 to 30 mL of water or less at 15-25° C. See United States Pharmacopoeia (USP) and European Pharmacopoeia (EP) solubility criteria (e.g., USP, General Notices, 5.30 Description and Solubility (May 1, 2019) as measured according to USP <1236>(Dec. 1, 2019)).

Subject: By "subject" or "individual" or "animal" or "patient" or "mammal," is meant any subject, particularly a mammalian subject, for whom diagnosis, prognosis or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain aspects, the mammal is a human subject. In other aspects, a subject is a human patient. In a particular aspect, a subject is a human patient with a pathological calcification or at risk of having pathological calcifications. In some aspects, the subject is a human patient with a pathological calcification, for example an ectopic calcification such as a calciphylaxis calcification in need of treatment. In some aspects, the subject is a human patient with a cardiovascular calcification in need of treatment.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutic agent: As used herein, the term "therapeutic agent" is used in a broad sense to include a composition comprising an inositol phosphate of the present invention, e.g., a salt of inositol hexaphosphate (e.g., $Na_6IP_6$ or $Na_{12}IP_6$) disclosed herein, that can provide a significant therapeutic benefit to a subject in need thereof, in particular, a subject suffering from or at risk of developing ectopic calcifications. Thus, a therapeutic agent according to the present invention can be, for example, (i) any salt of inositol hexaphosphate (e.g., $Na_6IP_6$, $Na_5IP_6$, $K_4IP_6$, $K_6IP_6$, $(NH_4)_6IP_6$)) disclosed herein or a combination thereof or (ii) any dosage form, pharmaceutical composition or formulation disclose herein comprising a salt of inositol hexaphosphate (e.g., $Na_6IP_6$, $Na_5IP_6$, $K_4IP_6$, $K_6IP_6$, $(NH_4)_6IP_6$)) disclosed herein or a combination thereof or (iii) a combination of a salt of inositol hexaphosphate (e.g., $Na_6IP_6$, $Na_5IP_6$, $K_4IP_6$, $K_6IP_6$, $(NH_4)_6IP_6$)) disclosed herein or a combination thereof with one or more additional therapeutic agents, that is administered in an amount sufficient to effect beneficial or desired results.

The term therapeutic agent also encompasses prophylactic, diagnostic or imaging agents comprising a salt of inositol hexaphosphate (e.g., $Na_6IP_6$, $Na_5IP_6$, $K_4IP_6$, $K_6IP_6$, $NH_4)_6IP_6$)) disclosed herein, wherein the therapeutic agent is administered, e.g., parenterally or topically. Therapeutic agents of the present invention include not only agents that treat ectopic calcifications or cardiovascular calcifications, but also agents that can ameliorate and/or prevent any symptom associated with the presence of a pathological calcification. Thus, as defined herein, the term therapeutic agent would include, for example, agents that can reduce or suppress inflammation, agent that increase the patient's mobility, and agents that reduce pain.

Treating, treatment, therapy: As used herein, the terms "treating" or "treatment" or "therapy" refer to partially or completely alleviating, ameliorating, improving, relieving, delaying the onset of, inhibiting the progression of, reducing the severity of, reducing the incidence of one or more symptoms or features of disease or any combination thereof. For example, "treating" calciphylaxis can refer, e.g., to inhibiting calcification, reducing the size of calcification, increasing survival, increasing mobility, reducing pain or any combination thereof.

A treatment comprising a salt of inositol hexaphosphate (e.g., $Na_6IP_6$, $Na_5IP_6$, $K_4IP_6$, $K_6IP_6$, $(NH_4)_6IP_6$)) disclosed herein can be administered to a subject who does not exhibit signs of a disease, disorder, and/or condition, and/or to a subject who exhibits only early signs of a disease, disorder, and/or condition for the purpose of, e.g., (i) decreasing the risk of developing a pathology associated with the disease, disorder, and/or condition, (ii) delaying the onset of the disease, disorder, and/or condition or a pathology associated with said disease, disorder, and/or condition or (iii) mitigating the symptoms and/or sequels of the disease, disorder, and/or condition or a pathology associated with said disease, disorder, and/or condition.

Thus, in general, the term "treatment" refers to countering the effects caused as a result of the disease or pathological condition of interest in a subject including (i) inhibiting the disease or pathological condition, in other words, slowing or stopping the development or progression thereof; (ii) relieving the disease or pathological condition, in other words, causing said disease or pathological condition or the symptoms thereof, to regress; (iii) stabilizing the disease or pathological condition, and (iv) any combination thereof. 2. Manufacturing processes The present invention provides processes for preparing soluble salts of inositol phosphates (IP) characterized by the formation of low levels of impurities during their execution. These processes improve the operability, scalability, reproducibility, and safety features of previously described processes for the preparation of $Na_6IP_6$. As a result, the processes of the invention yield an IP drug substance (e.g., $Na_6IP_6$) of high purity. The suitability of the IP drug substance so obtained for its use in human health and, particularly, for the treatment of various pathologies related to calcium crystallization is thus enhanced.

Recrystallization process: A key aspect of the methods to produce $Na_6IP_6$ disclosed herein is to use $Na_{12}IP_6$ purified via recrystallization as starting material in the $Na_6IP_6$ production process. Accordingly, the present invention provides a process for purifying an inositol phosphate (IP) salt, e.g., an unpurified soluble IP salt, the process comprising the steps of:

(i) dissolving the IP salt in water to obtain an IP solution,
(ii) converting the IP solution to an IP suspension,
(iii) washing the IP suspension with an alcohol solution to obtain an IP solid, and
(iv) drying the IP solid to obtain a purified IP salt.

As used herein, the terms "IP solution," "$Na_6IP_6$ solution," and "$Na_{12}IP_6$ solution" refers to a composition comprising IP, $Na_6IP_6$ or $Na_{12}IP_6$ dissolved in a solvent, e.g., an aqueous solvent such as water. In general, the term "solution" means a liquid preparation that contains one or more soluble active ingredients (e.g., an IP of the present invention) dissolved in a solvent.

As used herein, the terms "IP suspension," "$Na_6IP_6$ suspension," and "$Na_{12}IP_6$ suspension" refers to a composition comprising IP, $Na_6IP_6$ or $Na_{12}IP_6$ particles or crystals that are the result of the IP, $Na_6IP_6$ or $Na_{12}IP_6$ having fallen out of solution in the solvent, e.g., an aqueous solvent such as water. Accordingly, in the suspension the IP, $Na_6IP_6$ or $Na_{12}IP_6$ particles or crystals are suspended in the solvent. In general, the term "suspension" means a finely divided, undissolved active ingredient (e.g., an IP of the present invention) suspended, i.e., not dissolved, in a solvent.

As used herein, the terms "IP solid," "Na$_6$IP$_6$ solid," or "Na$_{12}$IP$_6$ solid" refer to a mass, pellet or cake of IP, Na$_6$IP$_6$ or Na$_{12}$IP$_6$ resulting from the partial separation of the IP, Na$_6$IP$_6$ or Na$_{12}$IP$_6$ particles or crystals from the solvent, e.g., via centrifugation or via filtration.

As used herein, the terms "recrystallized IP salt," "recrystallized Na$_6$IP$_6$," or "recrystallized Na$_{12}$IP$_6$" refers to the purified product obtained after water has been removed from an IP solid, Na$_6$IP$_6$ solid or Na$_{12}$IP$_6$ solid, e.g., by drying.

In some aspects, the IP salt is of plant origin. Sources of IP salts (e.g., phytin) include, but are not limited to, species of the Cucurbitaceae, Fabaceae, Juglandaceae, Poaceae, Rosaceae, Rubiaceae, and Solanaceae families or combinations thereof. Examples of species belonging to the Cucurbitaceae family include, but are not limited to, varieties of the (a) *Citrullus* genus such as citron melon (C. caffer) and watermelon (C. lanutus), (b) *Cucumis* genus such as cucumber (C. sativus) (c) *Cucurbita* genus such as zucchini (C. pepo) and (d) Lagenaria genus such as calabash (L. siceraria). Examples of species belonging to the Fabaceae family include, but are not limited to, varieties of the (a) *Arachis* genus such as peanut (A. hypogaea) and pinto peanut (A. pintoi), (b) *Ceratonia* genus such as carob (C. siliqua), (c) *Glycine* genus such as soybean (G. max), (d) *Glycyrrhiza* genus such as liquorice (G. glabra) and American licorice (G. lepidota), (e) Lens genus such as lentil (L. culinaris), (f) *Medicago* genus such as alfalfa (M. sativa), (g) *Phaseolus* genus such as chickpeas (C. arietinum), white, pinto and black beans (P. vulgaris), and (h) *Pisum* genus such as pea (P. sativum). Examples of species belonging to the Juglandaceae family include, but are not limited to, varieties of the *Juglans* genus such as walnut (J. regia). Examples of species belonging to the Poaceae family include, but are not limited to, varieties of the (a) *Avena* genus such as oat (A. sativa) and (b) Oriza genus such as rice (O. sativa). Examples of species belonging to the Rosaceae and Rubiaceae families include, but are not limited to, varieties of the *Prunus* genus such as almonds (P. dulcis) and varieties of the *Coffea* genus such as coffee (C. arabica), respectively. Examples of species belonging to the Solanaceae family include, but are not limited to, varieties of the *Solanum* genus such as potato (S. tuberosum) and tomato (S. lycopersicum). In some aspects, the IP salt is obtained or derived from plant varieties modified genetically for (a) increasing the production of the IP salt, (b) increasing the purity of the IP salt, (c) facilitating the separation or extraction of the IP salt from the vegetable material or (d) reducing or silencing the expression of other compounds that may hinder the production or extraction of the IP salt from the vegetable material.

In some aspects, the IP salt is synthesized chemically or is obtained by processes that combine chemical and biological steps.

In some aspects, the Na$_{12}$IP$_6$ used in the Na$_6$IP$_6$ (FIG. 2) preparation processes of the invention is recrystallized prior to its use. The purified Na$_{12}$IP$_6$ can be obtained by:
  (i) dissolving the Na$_{12}$IP$_6$ starting material in water to obtain a first Na$_{12}$IP$_6$ suspension;
  (ii) heating the first Na$_{12}$IP$_6$ suspension to obtain a Na$_{12}$IP$_6$ solution;
  (iii) seeding the Na$_{12}$IP$_6$ solution with Na$_{12}$IP$_6$ crystals and stirring to obtain a second Na$_{12}$IP$_6$ suspension;
  (iv) washing and filtering the second Na$_{12}$IP$_6$ suspension with ethanol to obtain a solid; and,
  (v) drying the solid to obtain the purified Na$_{12}$IP$_6$.

In some aspects, the Na$_{12}$IP$_6$ used in the Na$_6$IP$_6$ (FIG. 2) preparation processes of the invention is recrystallized prior to its use. The purified Na$_{12}$IP$_6$ can be obtained by:
  (i) dissolving the Na$_{12}$IP$_6$ starting material in water to obtain a first Na$_{12}$IP$_6$ suspension;
  (ii) heating the first Na$_{12}$IP$_6$ suspension to obtain a Na$_{12}$IP$_6$ solution;
  (iii) seeding the Na$_{12}$IP$_6$ solution with Na$_{12}$IP$_6$ crystals and stirring to obtain a second Na$_{12}$IP$_6$ suspension;
  (iv) washing the second Na$_{12}$IP$_6$ suspension with ethanol to obtain a solid and centrifuging it; and,
  (v) drying the solid to obtain the purified Na$_{12}$IP$_6$.

In some aspects of the recrystallization processes disclosed herein, the IP salt and water of step (i) are mixed in about a 1:1 to about 1:30 weight ratio. In some aspects of the recrystallization processes disclosed herein, the IP salt and water of step (i) are mixed in a 1:2 weight ratio. In some aspects, the IP salt and water of step (i) are mixed in a 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9 or 1:3 weight/weight (w/w) ratio.

In some aspects of the recrystallization processes disclosed herein, the IP solution of step (i) is heated. In some aspects, the IP solution is heated at a temperature between about 40° C. and 50° C. In some aspects, the IP solution is heated at a temperature between about 41° C. and 49° C. In some aspects, the IP solution is heated at a temperature between about 42° C. and 48° C. In some aspects, the IP solution is heated at a temperature between about 43° C. and 47° C. In some aspects, the IP solution is heated at a temperature between about 44° C. and 46° C. In some aspects, the IP solution is heated at a temperature of about 38° C., about 39° C., about 40° C., about 41° C., about 42° C., about 43° C., about 44° C., about 45° C., about 46° C., about 47° C., about 48° C., about 49° C. or about 50° C.

In some aspects of the recrystallization processes disclosed herein, the IP solution is heated for about 4 hours or less. In some aspects, the IP solution is heated for about 2 hours or less. In some aspects, the IP solution is heated for about 0.2 hours, about 0.3 hours, about 0.4 hours, about 0.5 hours, about 0.6 hours, about 0.7 hours, about 0.8 hours, about 0.9 hours, about 1 hour, about 1.1 hours, about 1.2 hours, about 1.3 hours, about 1.4 hours, about 1.5 hours, about 1.6 hours, about 1.7 hours, about 1.8 hours, about 1.9 hours, about 2 hours, about 2.1 hours, about 2.2 hours, about 2.3 hours, about 2.4 hours, about 2.5 hours, about 2.6 hours, about 2.7 hours, about 2.8 hours, about 2.9 hours, about 3 hours, about 3.1 hours, about 3.2 hours, about 3.3 hours, about 3.4 hours, about 3.5 hours, about 3.6 hours, about 3.7 hours, about 3.8 hours, about 3.9 hours or about 4 hours. In some aspects, the IP solution is heated for between about 0.5 hours and about 1 hour, between about 1 hour and about 1.5 hours, between about 1.5 hours and about 2 hours, between about 2 hours and about 2.5 hours, between about 2.5 hours and about 3 hours, between about 3 hours and about 3.5 hours or between about 3.5 hours and about 4 hours.

In some aspects of the recrystallization processes disclosed herein, the IP solution is filtered, e.g., to remove insoluble impurities.

In some aspects of the recrystallization processes disclosed herein, the IP solution is seeded with crystals of the IP salt previously recrystallized. In some aspects, the IP solution is seeded with crystals representing about 0.4% (w/w) or less of the IP salt of step (i). In some aspects, the IP solution is seeded with crystals of the IP salt previously recrystallized representing about 0.1% (w/w) or less of the IP salt of step (i). In some aspects, the amount of crystal of the IP salt used for seeding is about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19% or about 0.2%, about 0.21%, about 0.22%, about 0.23%, about 0.24%, about 0.25%, about 0.26%, about 0.27%, about 0.28%, about 0.29%, about 0.3%, about 0.31%, about 0.32%, about 0.33%, about 0.34%, about 0.35%, about 0.36%, about 0.37%, about 0.38%, about 0.39%, about 0.40% (w/w) or less of the IP salt of step (i).

In some aspects of the recrystallization processes disclosed herein, the IP solution is stirred. In some aspects of the recrystallization processes disclosed herein, the alcohol solution in step (iii) comprises, consists or consists essentially of a $C_1$-$C_4$ alcohol, e.g., methanol, ethanol, propanol, isopropanol, butanol or any combination thereof. In a specific aspect, the $C_1$-$C_4$ alcohol is ethanol.

In some aspects of the recrystallization processes disclosed herein, the drying of the solid of step (iv) is conducted at about 50° C. or less. In some aspects, the drying of the solid of step (iv) is conducted at about 45° C. or less. In some aspects, the drying of the solid of step (iv) is conducted at about 40° C. or less. In some aspects, the drying of the solid of step (iv) is conducted at about at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C. or about 40° C., about 41° C., about 42° C., about 43° C., about 44° C., about 45° C., about 46° C., about 47° C., about 48° C., about 49° C. or about 50° C.

In some aspects, drying is conducted during about 25 minutes, about 30 minutes, about 35 minutes, 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes or about 120 minutes.

In some aspects, drying is conducted under vacuum. In some aspects, drying is conducted under a pressure of about 1 mbar, about 0.9 mbar, about 0.8 mbar, about 0.7 mbar, about 0.6 mbar, about 0.5 mbar, about 0.4 mbar, about 0.3 mbar, about 0.2 mbar, about 0.1, about 0.09 mbar, about 0.08 mbar, about 0.07 mbar, about 0.06 mbar, about 0.05 mbar, about 0.04 mbar, about 0.03 mbar, about 0.02 mbar or about 0.01 mbar. In some aspects, drying is conducted under a pressure of below about 1 mbar, below about 0.9 mbar, below about 0.8 mbar, below about 0.7 mbar, below about 0.6 mbar, below about 0.5 mbar, below about 0.4 mbar, below about 0.3 mbar, below about 0.2 mbar, below about 0.1, below about 0.09 mbar, below about 0.08 mbar, below about 0.07 mbar, below about 0.06 mbar, below about 0.05 mbar, below about 0.04 mbar, below about 0.03 mbar, below about 0.02 mbar or below about 0.01 mbar. In a particular aspect, drying is conducted at approx. 40° C., at approx. 1 mbar, for about 60 minutes. In other particular aspects, drying is conducted at approx. 25° C., at approx. 0.01 mbar, for about 90 minutes.

The person skilled in the art knows that simultaneous changes to the temperature, duration, and pressure conditions of step (iv) could yield a product of similar characteristics (e.g., by reducing pressure and temperature while and increasing the duration of the drying step). For instance, the temperature and pressure in step (iv) could be set at 25° C. and 1 mbar, respectively, for 88 minutes, to obtain a level of impurities (0.52% w/w) which is also attained when this step is conducted at 40° C. and 0.01 mbar for 64 minutes. These combinations of temperature, duration and pressure are considered within the scope of the present invention and the common sense of the person skilled in the art.

In some aspects, the recrystallization process of the present invention can be used to produce a starting material or intermediate for the production of another form of the IP. For example, $Na_{12}IP_6$ recrystallized according to the processes disclosed herein can be used to produce $Na_6IP_6$. In other aspects, one or more iterations of the recrystallization processes disclosed herein can be used to increase the purity of an IP. Thus, for example, $Na_6IP_6$ produced according to the methods disclosed herein can be further purified by the application of one or more cycles of recrystallization disclosed herein to improve the purity of the final product.

The recrystallization processes disclosed herein are characterized by using an IP (e.g., $Na_{12}IP_6$, $Na_6IP_6$, $K_{12}IP_6$ or $K_6IP_6$) as the starting IP material and:

(1) dissolving the IP material in water at approx. a 1:2 ratio;
(2) dissolving the IP material at a temperature not to exceed 50° C. (suspension within 45-50° C. range);
(3) keeping the dissolved IP material at a temperature not to exceed 50° C. for less than 4 hours;
(4) adding a $C_1$-$C_4$ alcohol (e.g., ethanol) to separate the crystallized IP solid;
(5) concentrating the crystallized IP solid via filtration and/or centrifugation;
(6) drying the IP solid at the temperature not to exceed 40° C.; or,
(7) any combination thereof.

Soluble IP salt preparation processes: The present invention also provides processes for preparing a soluble salt of an inositol phosphate (IP), e.g., a sodium salt of $IP_6$ (phytate) such as $Na_6IP_6$.

In some aspects, the process for preparing a soluble IP salt comprises:

(a) dissolving an IP salt (e.g., non-recrystallized $Na_{12}IP_6$, recrystallized $Na_{12}IP_6$ or a crude or unpurified $Na_{12}IP_6$ or $Na_6IP_6$) in an aqueous solvent, e.g., water, to obtain an IP solution;
(b) contacting the IP solution with an ion exchange medium, e.g., an AMBERLITE® resin;
(c) concentrating the ion exchanged IP solution obtained from step (b) to obtain an IP syrup; and,
(d) separating the soluble IP salt from the IP syrup in the presence of an alkoxide.

Figure 4:
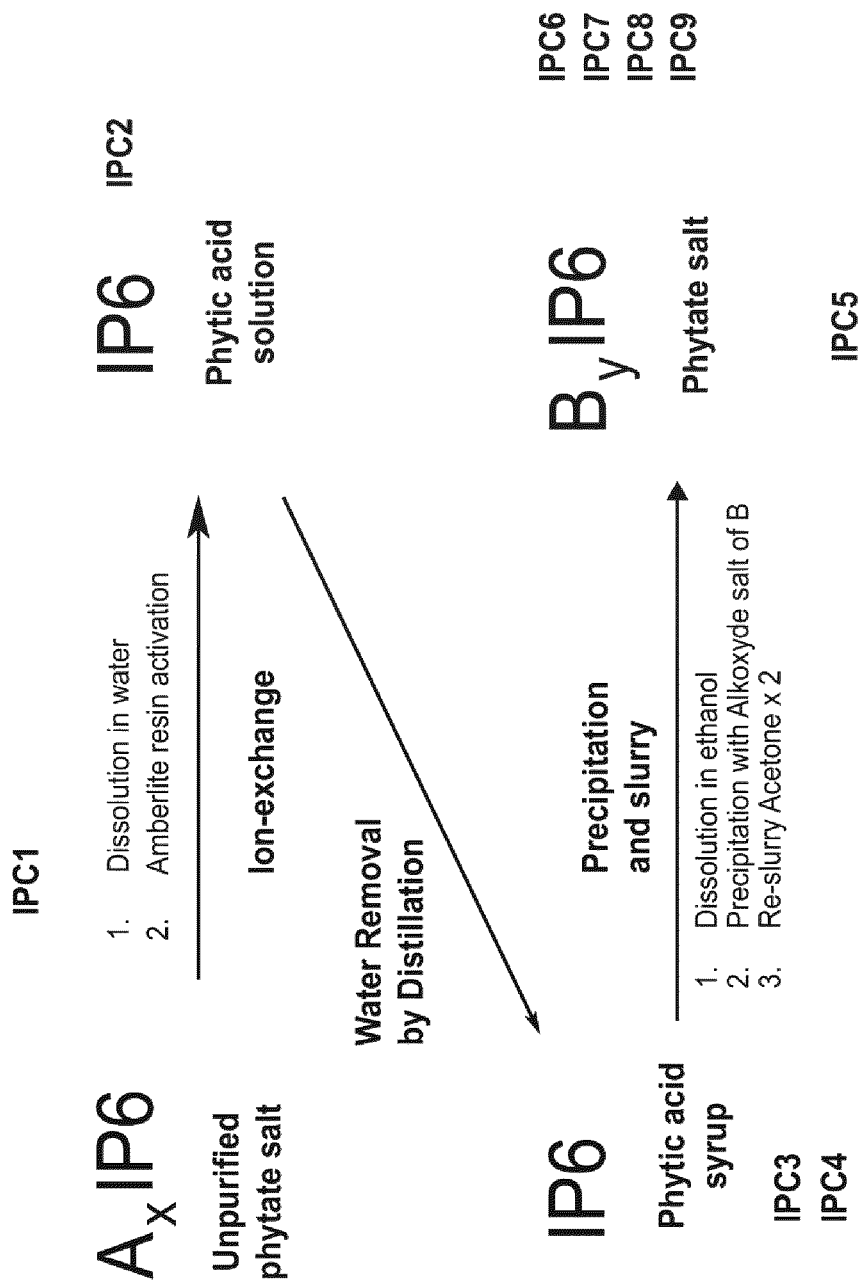
FIG. 4 shows a schematic representation of the steps used to produce an $IP_6$ salt in manufacturing processes (i.e., Process 1 and Process 2) not including the starting material recrystallization process, wherein A=B or is different, and x and y are an integer number from 1 to 12. In-process control tests (IPCs) are indicated.
Figure 5:
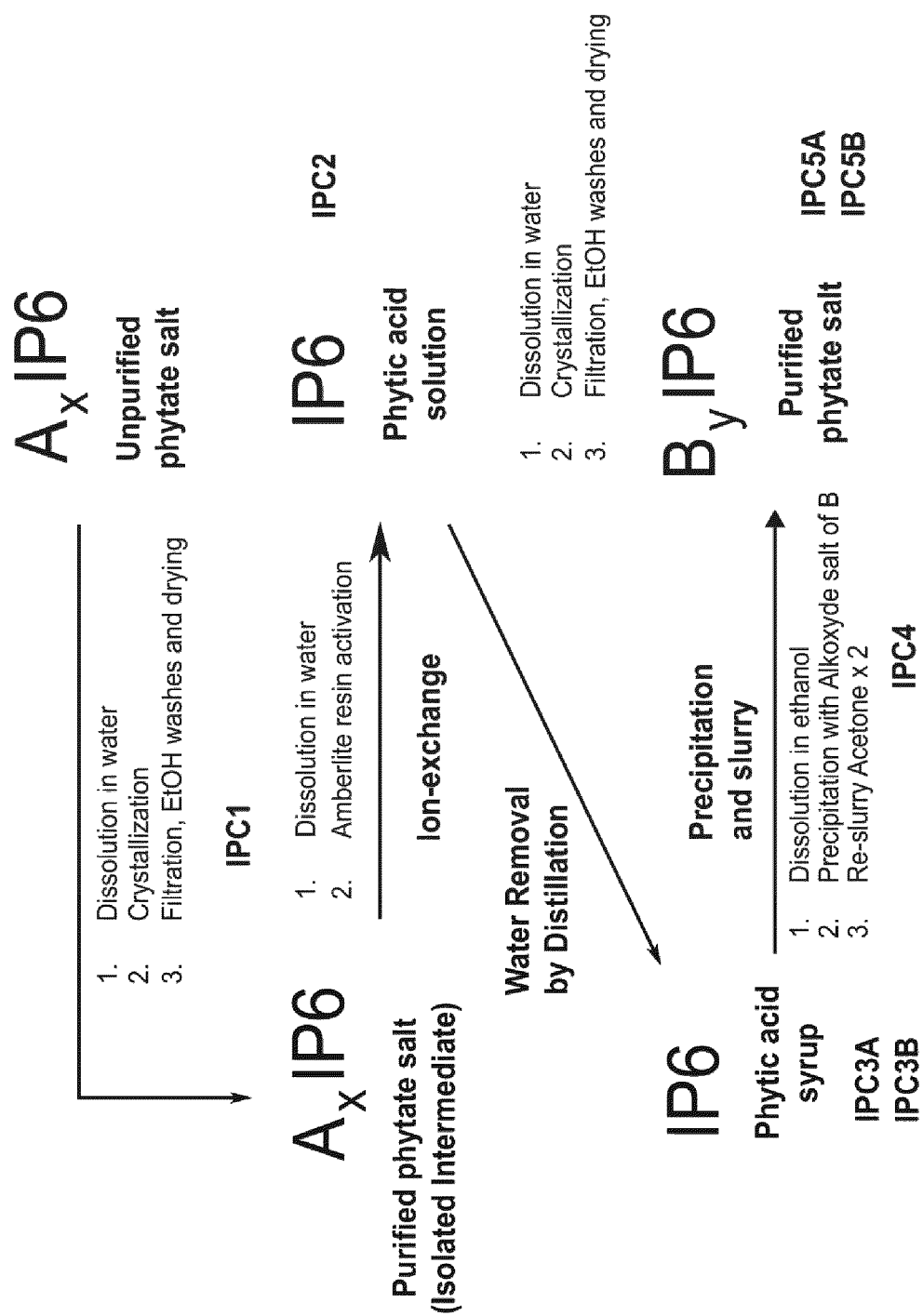
FIG. 5 shows a schematic representation of the steps used to produce an $IP_6$ salt in the current manufacturing process (i.e., Process 3) including the starting material purification process, wherein A=B or is different, and x and y are an integer number from 1 to 12. In-process control tests (IPCs) are indicated.
Figure 6:
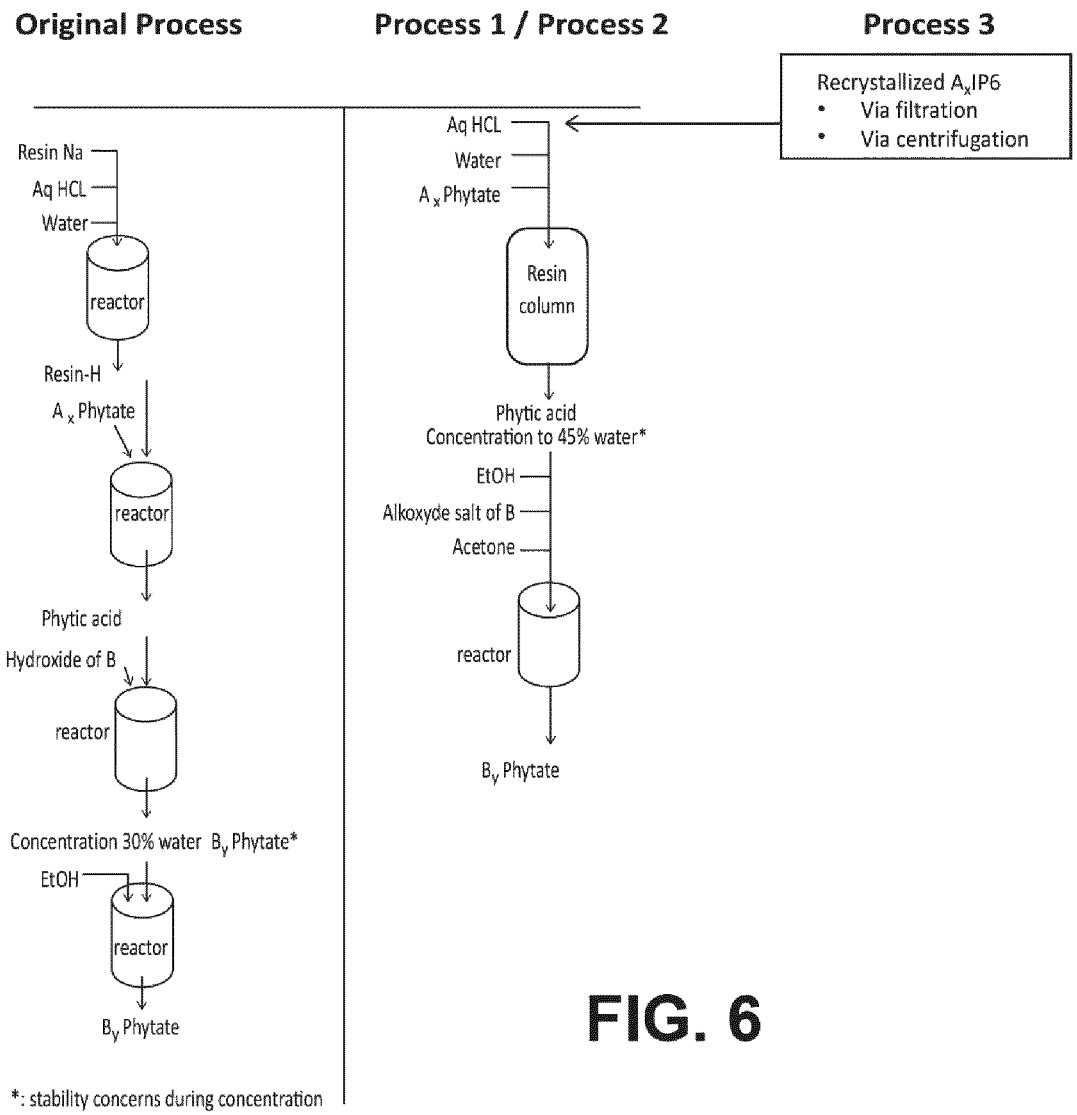
FIG. 6 shows the comparative manufacturing schemes of both, Process 1 (i.e., original process) and Process 2 (i.e., scaled-up process), so main differences between them can be easily observed. Process 3, which has been developed in order to significantly improve the quality of the drug substance with respect to its impurities content, introduces a new purification step of an $IP_6$ salt starting material, by recrystallization from a water solution to obtain a purified $IP_6$ salt as an isolated intermediate. A=B or is different, and x and y are an integer number from 1 to 12.

Schematic representations of the processes disclosed herein are provided in FIG. 4 (Processes 1 and 2) and FIG. 5 (Process 3).

Thus, the invention provides a soluble IP salt preparation process which comprises the removal of all cations (e.g., $Na^+$, $K^+$, $NH_4$) from the starting material or intermediate (e.g., $Na_{12}IP_6$, $Na_{10}IP_6$, $K_6IP_6$, $K_{12}IP_6$, $(NH_4)_{12}IP_6$)) by using an ion-exchange medium, the resulting acid form of the IP (e.g., phytic acid) is concentrated to yield a syrup, and the syrup is subsequently treated with an alkoxide (e.g., a methoxide such as sodium methoxide) under precise ratio and pH conditions. Cations from the alkoxide interact with the IP acid to yield a purified IP salt product with the desired cation: IP stoichiometry (e.g., $Na_6IP_6$, in which the sodium/phosphate ratio is 1:1).

Figure 3:
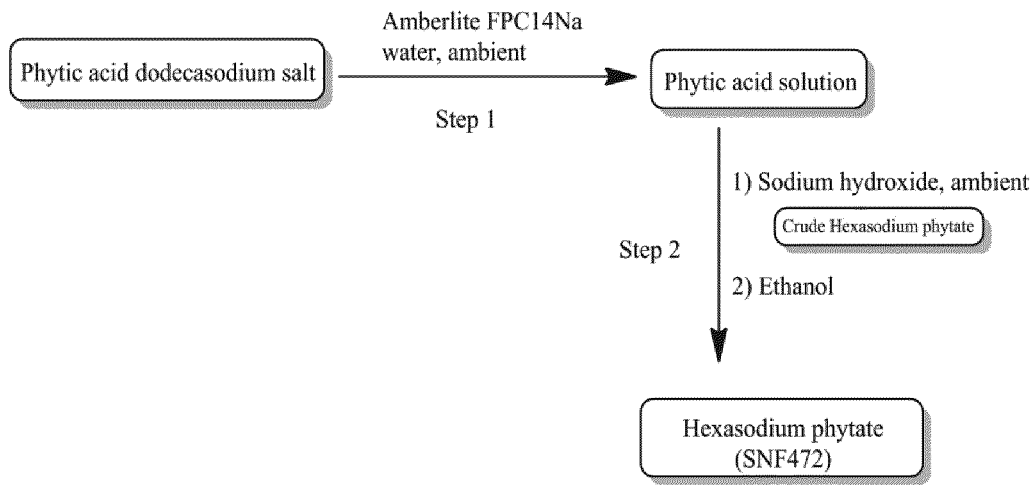
FIG. 3 shows the original synthesis process of $Na_6IP_6$. The process consisted of a two-step ion-salt exchange that included conversion of the starting material phytic acid dodecasodium salt to phytic acid by means of ion exchange chromatography (step 1) and the synthesis of hexasodium phytate by neutralization of the phytic acid with an exact amount of sodium hydroxide followed by ethanol-assisted precipitation (step 2) to isolate final drug substance.
Figure 3:
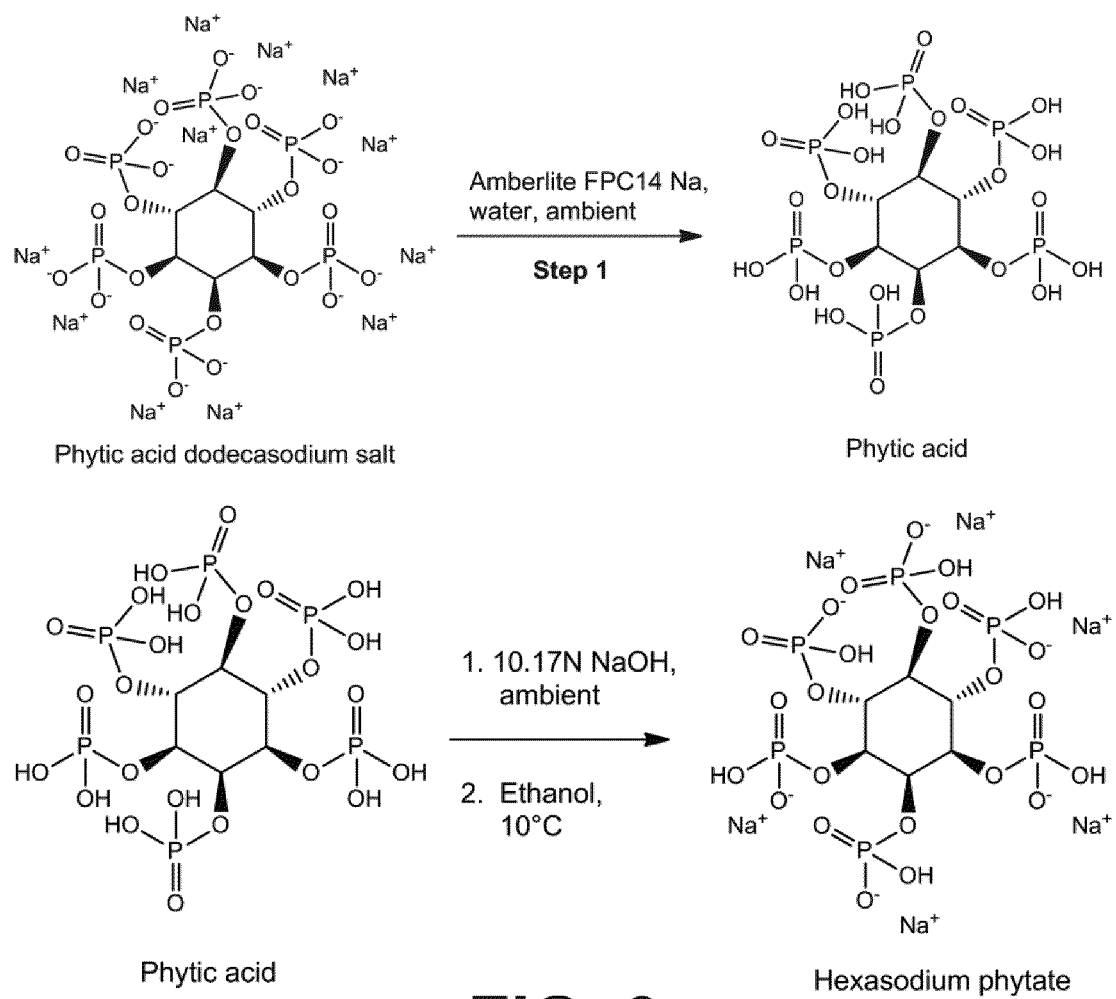

Whereas the original manufacturing process was a 2-step process (See FIG. 3), the current processes are 3 step processes comprising (1) a cation removal step (a) to (b), (2) a concentration step (b) to (c), and (3) a cation replacement step (c) to (d).

In some specific aspects of the invention, the soluble IP salt preparation process is directed to the preparation of $Na_6IP_6$. Accordingly, in some aspects, the present invention provides a soluble IP salt preparation process comprising:
(a) dissolving $Na_{12}IP_6$ (e.g., recrystallized $Na_{12}IP_6$) in water to obtain an $IP_6$ solution;
(b) passing the $IP_6$ solution through an ion exchange medium loaded, e.g., with AMBERLITE® resin;
(c) concentrating the ion exchanged $IP_6$ solution obtained from step
(b) via distillation (e.g., in a rotary evaporator) to obtain an $IP_6$ syrup; and, (d) adding sodium methoxide ($CH_3NaO$) to the IP syrup to obtain $Na_6IP_6$. See FIG. 4 and FIG. 5.

In some aspects, the ion exchange medium of step (b) is conducted in an ion exchange chromatography system (e.g., in a column), (ii) an ion exchange batch process or (iii) a pH adjustment system.

The term "ion exchange chromatography" or "IXC" as used herein, refers to process for separating molecules based on their differences in net surface charge. IXC takes advantage of the fact that the relationship between net surface charge and pH is unique for a specific molecule. In an IXC separation, reversible interactions between charged molecules and oppositely charged IXC media are controlled in order to favor binding or elution of specific molecules and achieve separation. An IXC medium comprises a matrix of spherical particles substituted with ionic groups that are negatively or positively charged. The matrix is usually porous to give a high internal surface area. The medium could be packed into a column to form a packed bed. The bed is then equilibrated with buffer which fills the pores of the matrix and the space in between the particles. See Ninfa A, et al., Fundamental Laboratory Approaches for Biochemistry and Biotechnology (John Wiley & Co, Hoboken, NJ, USA, 2010).

The terms "ion exchange batch process" or "batch process" as used herein, relates to an ion exchange separation technique wherein the separation occurs in a closed system (e.g., reactor). Thus, the inflow of additional analyte through the matrix, as in an ion exchange column, is not available. In this technique, the ion exchange matrix and the analyte solution are mixed in a batch vessel until they reach an equilibrium. Then, the matrix is filtered off from the solution, washed and regenerated in a special system to collect the molecule of interest.

The term "pH adjustment system" as used herein, refer to the use of changes in the pH of an analyte solution for modulating the strength with which a molecule of interest attaches to an ion exchange matrix. This manipulation could allow the identification and release at will of the molecule of interest.

In some aspects, the IP solution of steps (a) and (b) comprises, consists or consists essentially of a dodecasodium salt of IP (e.g., $Na_{12}IP_6$). In other aspects, the IP solution of steps (a) and (b) comprises, consists or consists essentially of a decasodium salt of IP (e.g., $Na_{10}IP_6$), hexapotassium salt of IP (e.g., $K_6IP_6$), dodecapotassium salt of IP (e.g., $K_{12}IP_6$) or a dodecammonium salt of IP (e.g., $(NH_4)_{12}IP_6$). In other aspects, the IP solution of steps (a) and (b) comprises, consists or consists essentially of a hexasodium salt of IP (e.g., $Na_6IP_6$). In other aspects, the IP solution of steps (a) and (b) comprises, consists or consists essentially of a tetrapotassium salt of IP (e.g., $K_4IP_6$), pentasodium salt of IP (e.g., $Na_5IP_6$), hexapotassium salt of IP (e.g., $K_6IP_6$) or a hexammonium salt of IP (e.g., $(NH_4)_6IP_6$).

In some aspects, the ion exchanged IP solution obtained from step (b) and the IP syrup of step (c) comprise, consist or consist essentially of a hexasodium salt of IP (e.g., $Na_6IP_6$). In other aspects, the ion exchanged IP solution obtained from step (b) and the IP syrup of step (c) comprise, consist or consist essentially of a tetrapotassium salt of IP (e.g., $K_4IP_6$), pentasodium salt of IP (e.g., $Na_5IP_6$), hexapotassium salt of IP (e.g., $K_6IP_6$) or a hexammonium salt of IP (e.g., $(NH_4)_6IP_6$).

In some aspects, the concentration of step (c) is conducted by distilling the IP solution at about 55° C. or less. In some additional aspects, step (c) is conducted by distilling the IP solution at about 25° C. to about 55° C. In some further aspects, step (c) is conducted by distilling the IP solution at about 40° C. to about 45° C. In some further aspects, step (c) is conducted by distilling the IP solution at about 40° C.

In some aspects, the concentration of step (c) is conducted by distilling the IP solution at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C. or about 40° C., about 41° C., about 42° C., about 43° C., about 44° C., about 45° C., about 46° C., about 47° C., about 48° C., about 49° C. or about 50° C., about 51° C., about 52° C., about 53° C., about 54° C. or about 55° C. In some aspects, the concentration of step (c) is conducted by distilling the IP solution at a temperature below about 40° C., below about 39° C., below about 38° C., below about 37° C., below about 36° C., below about 35° C., below about 34° C., below about 33° C., below about 32° C., below about 31° C., below about 30° C., below about 29° C., below about 28° C., below about 27° C., below about 26° C. or below or about 25° C. In some aspects, the concentration of step (c) is conducted by distilling the IP solution at a temperature between about 20° C. and about 25° C., between about 25° C. and about 30° C., between about 30° C. and about 35° C., between about 35° C. and about 40° C., between about 40° C. and about 45° C., between about 45° C. and about 50° C. or between about 50° C. and about 55° C.

In some aspects, the concentration of step (c) is conducted by distilling the IP solution for about 16 hours or less. In some aspects, the concentration of step (c) is conducted by distilling the IP solution for about 1 hour to about 16 hours. In some aspects, the concentration of step (c) is conducted by distilling the IP solution for about 12 hours to about 14 hours. In some aspects, the concentration of step (c) is conducted by distilling the IP solution for about 16 hours, for about 15 hours, for about 14 hours, about 13 hours, about 12 hours, about 11 hours, about 10 hours, about 9 hours, about 8 hours, about 7 hours, about 6 hours, about 5 hours, about 4 hours, about 3 hours, about 2 hours or about 1 hour. In some aspects, the concentration of step (c) is conducted by distilling the IP solution for about 1 hour to about 2 hours, about 2 hours to about 3 hours, about 3 hours to about 4 hours, about 4 hours to about 5 hours, about 5 hours to about 6 hours, about 6 hours to about 7 hours, about 7 hours to about 8 hours, about 8 hours to about 9 hours, about 9 hours to about 10 hours, about 10 hours to about 11 hours, about 11 hours to about 12 hours, about 12 hours to about 13 hours, about 13 hours to about 14 hours, about 14 hours to about 15 hours or about 15 hours to about 16 hours.

In some aspects, the concentration of step (c) is conducted by distilling the IP solution under vacuum. In some aspects, the concentration of step (c) is conducted by distilling the IP solution under vacuum at a pressure of about 1 mbar, about 0.9 mbar, about 0.8 mbar, about 0.7 mbar, about 0.6 mbar, about 0.5 mbar, about 0.4 mbar, about 0.3 mbar, about 0.2 mbar, about 0.1, about 0.09 mbar, about 0.08 mbar, about 0.07 mbar, about 0.06 mbar, about 0.05 mbar, about 0.04 mbar, about 0.03 mbar, about 0.02 mbar or about 0.01 mbar. In some aspects, the concentration of step (c) is conducted by distilling the IP solution under vacuum at a pressure below about 1 mbar, below about 0.9 mbar, below about 0.8 mbar, below about 0.7 mbar, below about 0.6 mbar, below about 0.5 mbar, below about 0.4 mbar, below about 0.3 mbar, below about 0.2 mbar, below about 0.1, below about 0.09 mbar, below about 0.08 mbar, below about 0.07 mbar, below about 0.06 mbar, below about 0.05 mbar, below about 0.04 mbar, below about 0.03 mbar, below about 0.02 mbar or below about 0.01 mbar.

In some aspects, the water content of the IP syrup is between about 30% and 60% (w/w). In some aspects, the water content of the IP syrup is between about 40% and about 45% (w/w). As used herein, the term "syrup" refers to a concentrated solution of an IP salt of the present invention (e.g., $Na_6IP_6$). In some aspects, the water content of the IP syrup is at least about 40% (w/w), at least about 41% (w/w), at least about 42% (w/w), at least about 43% (w/w), at least about 44% (w/w), at least about 45% (w/w), at least about 46% (w/w), at least about 47% (w/w), at least about 48% (w/w), at least about 49% (w/w), at least about 50% (w/w), at least about 51% (w/w), at least about 52% (w/w), at least about 53% (w/w), at least about 54% (w/w), at least about 55% (w/w), at least about 56% (w/w), at least about 57% (w/w), at least about 58% (w/w), at least about 59% (w/w) or at least about 60% (w/w).

In some aspects, the water content of the IP syrup is about 40% (w/w), about 41% (w/w), about 42% (w/w), about 43% (w/w), about 44% (w/w), about 45% (w/w), about 46% (w/w), about 47% (w/w), about 48% (w/w), about 49% (w/w), about 50% (w/w), about 51% (w/w), about 52% (w/w), about 53% (w/w), about 54% (w/w), about 55% (w/w), about 56% (w/w), about 57% (w/w), about 58% (w/w), about 59% (w/w) or about 60% (w/w).

In some aspects, the water content of the IP syrup is between about 40% and about 45% (w/w). In some aspects, the water content of the IP syrup is between about 40% and about 42% (w/w), about 42% and about 44% (w/w), about 44% and about 46% (w/w), about 46% and about 48% (w/w), about 48% and about 50% (w/w), about 50% and about 52% (w/w), about 52% and about 54% (w/w), about 54% and about 56% (w/w), about 56% and about 58% (w/w) or about 58% and about 60% (w/w). In some aspects, the water content of the IP syrup is between about 45% and about 50% (w/w), about 50% and about 55% (w/w) or about 55% and about 60% (w/w).

In some aspects, the alkoxide is a $C_1$-$C_4$ alkoxide (e.g., methoxide, ethoxide, ter-butoxide, isoproxide or any combination thereof). In some aspects, the alkoxide is sodium methoxide, potassium methoxide, sodium ethoxide, potassium ethoxide, sodium ter-butoxide, potassium ter-butoxide, sodium isoproxide, potassium isoproxide or any combination thereof. In some aspects, the $C_1$-$C_4$ alkoxide is $CH_3NaO$, $CH_3CH_2NaO$, $CH_3KO$, $CH_3CH_2KO$ or any combination thereof.

In some aspects, step (d) is conducted at a pH between about pH 4.0 and about pH 5.5. In some aspects, step (d) is conducted at a pH of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4 or about 5.5. In some aspects, step (d) is conducted at a pH between about pH 4.1 and about pH 5.4, between about pH 4.2 and about pH 5.3, between about pH 4.3 and about pH 5.2, between about pH 4.4 and about pH 5.1, between about pH 4.5 and about pH 5.0, between about pH 4.6 and about pH 4.9, between about pH 4.7 and about pH 4.8. In some aspects, step (d) is conducted at a pH between about pH 4.0 and about pH 4.5, between about pH 4.5 and about pH 5.0, between about pH 5.0 and about pH 5.5, between about pH 4.4 and about pH 4.7, between about pH 4.3 and about pH 4.6, between about pH 4.4 and about pH 4.8 or between about pH 4.5 and about pH 4.9.

In some aspects, the ethanol is added to the IP syrup (e.g., $IP_6$ syrup) in step (d), followed by the addition of the alkoxide (e.g., sodium methoxide), which causes the precipitation of the soluble IP salt (e.g., $Na_6IP_6$). In some aspects, the precipitated soluble IP salt (e.g., $Na_6IP_6$) is re-slurried by the addition of acetone (e.g., 2 volumes of acetone).

In some aspects, the process for preparing a soluble salt of an inositol phosphate (IP) described above further comprises a step (e) wherein the soluble IP salt of step (d) is dried. In some aspects, the drying of step (e) comprises spray drying. In some aspects, the soluble IP salt of step (d) is purified.

In some aspects, the soluble IP salt of step (a) has been previously purified according to the recrystallization processed disclosed above. In some aspects, the soluble IP salt of steps (d) or (e) is further purified according to the recrystallization processes disclosed above.

In some aspects of the processes disclosed herein, the IP contains between 1 and 6 phosphate groups. In some aspects, the IP contains between 7 or 8 phosphate groups (e.g., a phosphate group is attached to another phosphate group already linked to the inositol phosphate scaffold). In some aspects, the IP consists or consists essentially of inositol hexaphosphate. In some aspects, the inositol hexaphosphate is myo-inositol hexaphosphate.

In some aspects, the IP salt (e.g., a salt of myo-inositol hexaphosphate) contains at least one monovalent cation. In some aspects, the IP salt contains at least one Group 1 alkali metal element cation (e.g., $Na^+$ or $K^+$). In some aspects, the IP salt contains at least one ammonium cation (i.e., $NH_4^+$). In some specific aspects, the Group 1 alkali metal element is sodium. In other aspects, the Group 1 alkali metal element is potassium. In some aspects, the Group 1 alkali metal element is a combination of sodium and potassium. In some aspects, the ratio of sodium to potassium, e.g., in a salt of myo-inositol hexaphosphate, is 1:5, 2:4, 3:3, 4:2 or 5:1 (sodium:potassium).

The present invention provides purified soluble IP salts obtained according to the processes described above. In some aspects, the purified soluble IP salt is a monovalent cationic salt of inositol hexaphosphate (e.g., $Na_6IP_6$, $Na_5IP_6$, $K_4IP_6$, $K_6IP_6$, $(NH_4)_6IP_6$). In a particular aspect, the purified soluble IP salt is $Na_6IP_6$.

The present invention provides also $IP_6$ salts with specific degrees of purity and specific impurity profiles which are characteristic of the $IP_6$ salts prepared according to the process disclosed herein. Accordingly, the present invention provides an $IP_6$ salt that is at least 70% (w/w) pure characterized for comprising:

(i) DL-Inositol 1,2,3,4,6-pentaphosphate≤2.0% (w/w),
(ii) DL-Inositol 1,2,3,5,6-pentaphosphate≤4.0% (w/w),
(iii) DL-Inositol 1,2,4,5,6-pentaphosphate≤5.0% (w/w), and,
(iv) DL-Inositol 1,3,4,5,6-pentaphosphate≤3.0% (w/w).

Also provided is an $IP_6$ salt that is at least 80% (w/w) pure characterized for comprising:

(i) DL-Inositol 1,2,3,4,6-pentaphosphate≤1.4% (w/w),
(ii) DL-Inositol 1,2,3,5,6-pentaphosphate≤2.1% (w/w),
(iii) DL-Inositol 1,2,4,5,6-pentaphosphate≤2.6% (w/w), and, (iv) DL-Inositol 1,3,4,5,6-pentaphosphate≤0.52% (w/w).

In some aspects, the $IP_6$ salts above are sodium $IP_6$ salts. In some further aspects, the $IP_6$ salt is a hexasodium $IP_6$ salt.

In some aspects, the present invention provides a process to produce a purified IP soluble salt, wherein the process comprises:

(1) generating an IP syrup (e.g., an $IP_6$ syrup) with a water content >40% w/w, preferably between 40% and 50% or between 40% and 45%);

(2) distilling an IP syrup (e.g., an $IP_6$ syrup) at a temperature below 45° C., preferably about 40° C., for no longer than 12 hours to 14 hours;

(3) adding an alkoxide to the IP syrup (e.g., an $IP_6$ syrup) wherein the alkoxide is $CH_3NaO$ or $CH_3CH_2NaO$;

(4) adding the alkoxide (e.g., $CH_3NaO$) to the IP syrup (e.g., an $IP_6$ syrup) until pH 4.5 is attained, e.g., until pH is between pH 4.0 and pH 5.5, preferably until pH is between pH 4.5 and pH 5.3, and more preferably until pH is 4.5; or, (5) any combination thereof.

In-process control tests (IPCs) conducted during the manufacturing processes described herein are intended to provide a means of monitoring product purity, yield and integrity and have evolved along time as more experience and information have been gained from process development and optimization.

In some aspects, the present invention provides a process of preparing a soluble IP salt, e.g., $Na_6IP_6$, wherein the process comprises several internal process control points (IPC 1-9) wherein said tests are performed to optimize the output of the process. See FIG. 4 and the table below.

TABLE 2

In-Process Control and acceptance criteria for drug substance manufacturing in Process 2 ("Scaled-Up Process"); See FIG. 4.

| IPC | IPC test | Acceptance Criteria |
|---|---|---|
| IPC1 | Purity by IC | RRT 0.69 area ≤ 0.04 μS * min. |
| IPC2 | Phytic Acid Content by IC | Report result (mg/mL) |
| IPC3 | Water Content by KF | ≤45% w/w |
| IPC4 | Assay and Impurities by IC | Report Results (% w/w) |
| IPC5 | pH range | 4.3-5.3 |
| IPC6 | Water Content by KF | ≤8% w/w |
| IPC7 | Impurities by IC | Report result (Total Impurities % w/w oasfb) |
| IPC8 | Residual Solvents by GC | Methanol ≤ 5000 ppm Ethanol ≤ 20000 ppm Acetone ≤ 5000 ppm |
| IPC9 | Sodium Content by ICP-MS Oasfb | 15.4-19.5% w/w |

In some aspects, the present invention provides a process of preparing a purified soluble IP salt, e.g., $Na_6IP_6$, $Na_5IP_6$, $K_4IP_6$, $K_6IP_6$, $(NH_4)_6IP_6$, wherein the process comprises several internal process control points (IPC 1-5B) wherein said tests are performed to optimize the output of the process. See FIG. 5, and the table below.

TABLE 3

In-Process Control and acceptance criteria for drug substance manufacturing in Process3 ("Purified Process"); See FIG. 5.

| Process Step | IPC | IPC test | Acceptance Criteria |
|---|---|---|---|
| Hexasodium Phytate | IPC1 | Purity by IC | RRT 0.69 area ≤ 0.04 μS * min. |
| (SNF472) Obtention | IPC2 | Phytic Acid Content by IC | Report result (mg/mL) |
| | IPC3A | Water Content by KF | ≤45% w/w |
| | IPC3B | Assay and Impurities by IC | Report Results (% w/w) |
| | IPC4 | pH range | 4.3-5.3 |
| | IPC5A | Water Content by KF | ≤8% w/w |
| | IPC5B | Residual Solvents by GC | Methanol ≤ 5000 ppm Ethanol ≤ 20000 ppm Acetone ≤ 5000 ppm |

Accordingly, the present invention provides a process of preparing a purified soluble TP salt, e.g., $Na_6IP_6$, $Na_5IP_6$, $K_4IP_6$, $K_6IP_6$, $(NH_{14})_6IP_6$), such as any of the processes comprising steps (a)-(d) or (a)-(e) disclosed above, in some aspects further comprising a recrystallization process disclosed herein, wherein the process comprises the disclosed internal process control points (IPC) and acceptance criteria or any combination thereof.

The present invention also provides pharmaceutical compositions comprising an TP salt produced according to any of the processes disclosed herein, e.g., $Na_6IP_6$ salt prepared according to any one of the methods disclosed or a mixture of those salts. In some aspects, the pharmaceutical composition pharmaceutical composition is injectable. In some aspects, the pharmaceutical composition is administered parenterally. In some aspects, the parenteral administration is intravenous. In some aspects, the intravenous administration is by bolus injection. In some aspects, the intravenous administration is via intravenous infusion.

The present invention also provides combination treatments comprising (i) compositions comprising an IP salt produced according to any of the processes disclosed herein, e.g., $Na_6IP_6$ salt prepared according to any one of the methods disclosed or a mixture of those salts, and (ii) at least a second therapeutic agent or treatment.

The present invention also provides a kit or article of manufacture comprising (i) compositions comprising an IP salt produced according to any of the processes disclosed herein, e.g., $Na_6IP_6$ salt prepared according to any one of the methods disclosed or a mixture of those salts, and (ii) instructions for use, e.g., instruction for administration to a subject in need thereof.

The present invention also provides methods for treating or preventing ectopic calcification or its consequences in a subject in need thereof comprising administering a composition comprising a therapeutic or prophylactic agent comprising an IP salt (e.g., $Na_6IP_6$) prepared according to any of the processes disclosed herein or a mixture of those salts. In some aspects, the subject is undergoing hemodialysis. In some aspects, the subject has end-stage renal disease. 3. Inositol phosphates (IP)

In some aspects of the present invention, the processes disclosed herein and variants thereof can be used to obtain other inositol phosphate (IP) salts with a high degree of purity. For example, for an inositol phosphate $IP_1$ to $IP_6$ of formula $A_xIP_y$, wherein (i) A is a monovalent cation such as an alkali cation (e.g., $Na^+$ or $K^+$), ammonium (i.e., $NH_4$) or a combination thereof), (ii) y is an integer between 1 and 6, and (iii) x is an integer between 1 and 12, which can be used to generate an inositol phosphate of formula $B_zIP_y$, via a process where the compound of formula $A_xIP_y$ is recrystallized from a source material, and is processed to yield the compound of formula $B_zIP_y$, where z is an integer between 1 and 12. In some aspects, B can be the same as A (i.e., the starting material and the final product have the same monovalent cation) or not (i.e., the starting material and the final product have different monovalent cations).

In some aspects, the compound of formula $A_xIP_y$ can be a hexacyclic (inositol) ring, however, other ring sizes are contemplated (e.g., 5 or 7 carbon rings), as well as hexacyclic rings having more than 6 phosphate groups (e.g., $IP_7$, $IP_8$), as disclosed elsewhere. In some aspects, P in the formula above can be phosphate, sulfate, thiophosphate or any combination thereof.

Accordingly, in some aspects, the inositol phosphates of the present invention comprise pharmaceutically acceptable salts (e.g., sodium salts or potassium salts) of compounds of formula I, a thereof or a combination thereof, prepared according to the methods disclosed herein, e.g., $Na_6IP_6$:

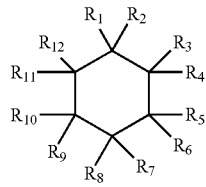

I wherein
(i) at least one of $R_1$, $R_3$, $R_5$, $R_7$, $R_9$ and $R_{11}$ independently represent OH, a compound of formula II or a compound of formula III or a compound for formula IV:

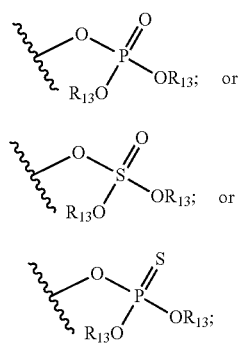

(ii) $R_2$, $R_4$, $R_6$, $R_8$, $R_{10}$, $R_{12}$ and $R_{13}$ represent H;
(iii) at least one of $R_1$, $R_3$, $R_5$, $R_7$, $R_9$ and $R_{11}$ represents a compound of formula II, formula III or formula IV, and
(iv) zero, one or two of $R_1$, $R_3$, $R_5$, $R_7$, $R_9$ and $R_{11}$ represent a heterologous moiety.

The formulas disclosed herein are meant to encompass any diastereomer.

In some aspects, at least one of $R_1$, $R_3$, $R_5$, $R_7$, $R_9$ and $R_{11}$ independently represents H, —X, —OX, —NHX, $NX_2$, —SX, —$OSO_3HX$, —$OSO_3X_2$ or a compound of formula II, formula III or formula IV, where each X independently represents H, $C_1$-30 alkyl, $C_2$-30 alkenyl, $C_2$-30 alkynyl or $Cy_1$, where $C_1$-30 alkyl, $C_2$-30 alkenyl and $C_{2-30}$ alkynyl are independently optionally substituted with one or more $R_{14}$ and where $Cy_1$ is optionally substituted by one or more $R_{15}$; $Cy_1$ represents a carbocyclic or heterocyclic three- to 10-membered ring, which can be saturated, partially unsaturated or aromatic, where said heterocycle has between one and four heteroatoms selected from amongst O, S and N, where said ring can be bound to the rest of the molecule via any available C atom and where $Cy_1$ is optionally fused to between one and four five- or six-membered rings, each saturated, partially unsaturated or aromatic, carbocyclic or heterocyclic, and where said fused heterocycle can contain one or two heteroatoms selected from amongst O, N and S; each $R_{13}$ independently represents H, $C_1$-30 alkyl, $NH_2$, —$NHC_{1-30}alkyl$ or $N(C_{1-30}alkyl)_2$, where each $C_1$-30 alkyl is independently optionally substituted with one or more halogen, OH, CN and $NO_2$ groups; and each $R_{14}$ and $R_{15}$ independently represents OH, $C_{1-30}$ alkoxy, $C_{1-30}$ alkyithionyl, $C_{1-30}$ acyloxy, phosphate, halogen, trihalo $C_{1-30}$ alkyl, nitrile azide.

In some aspects, each X independently represents H, $C_{1-30}$ alkyl or $Cy_1$, where $C_{1-30}$ alkyl is optionally substituted by one or more $R_{14}$ and where $Cy_1$ is optionally substituted by one or more $R_{15}$; and each $R_{14}$ and $R_{15}$ independently represents OH, $C_{1-30}$ alkoxy, $C_{1-30}$ alkyithionyl, $C_{1-30}$ acyloxy, phosphate, halogen, trihalo$C_{1-30}$alkyl, nitrile or azide. In some aspects, each X represents H, $C_{1-30}$alkyl or $Cy_1$. In some aspects, each X represents H.

In some aspects, at least one of radicals $R_1$, $R_3$, $R_5$, $R_7$, $R_9$ and $R_{11}$ independently represents a compound of formula II, formula III or formula IV, each $R_{13}$ independently represents H, $C_{1-30}$ alkyl, —$NH_2$, $NHC_{1-30}$ alkyl or $N(C_1-30$ alkyl$)_2$, where each $C_{1-30}$ alkyl is independently optionally substituted by one or more halogen, OH, CN and $NO_2$groups; and $R_2$, $R_4$, $R_6$, $R_8$, $R_{10}$ and $R_{12}$ independently represent H.

In another aspect, $R_1$, $R_3$, $R_5$, $R_7$, $R_9$ and $R_{11}$ independently represent a compound of formula II, formula III or formula IV, each $R_{13}$ independently represents H or $C_{1-30}$alkyl, where each $C_{1-30}$alkyl is independently optionally substituted by one or more halogen, OH, CN and $NO_2$ groups; and $R_2$, $R_4$, $R_6$, $R_8$, $R_{10}$ and $R_{12}$ independently represent H.

In another aspect, $R_1$, $R_3$, $R_5$, $R_7$, $R_9$ and $R_{11}$ independently represent a compound of formula II, formula III or formula IV, each $R_{13}$ independently represents H or $C_{1-30}$alkyl; and $R_2$, $R_4$, $R_6$, $R_8$, $R_{10}$ and $R_{12}$ independently represent H.

In another aspect, $R_1$, $R_3$, $R_5$, $R_7$, $R_9$ and $R_{11}$ independently represent a compound of formula II, formula III or formula IV, each $R_3$ independently represents H; and $R_2$, $R_4$, $R_6$, $R_8$, $R_{10}$ and $R_{12}$ independently represent H.

In a particular aspect, the compound is inositol hexaphosphate ($IP_6$). In some aspects, compound comprises an $IP_4$ or $IP_5$. Inositol is assumed to mean any isomeric form of the molecule.

All compounds of formula I contain C—O—P or C—O—S bonds, which provide the compounds with an affinity for calcium-containing crystals and a sufficiently labile bond to be hydrolyzed in vivo, thereby preventing irreversible binding to calcium-containing crystals such as the hydroxyapatite (HAP) in bone, which would have a negative impact on bone remodeling, as is the case with bisphosphonates when administered long term as said compounds contain P—C—P bonds that cannot be hydrolyzed by the body. At the other extreme are phosphorylated compounds that do not contain said C—O—P bonds, such as pyrophosphates, the P—O—P bonds of which mean that they are too readily hydrolyzed in the intestine, thus meaning that only parenteral administration is feasible.

The compounds of the present invention, with C—O—P bonds, C—O S bonds, and combinations thereof represent an adequate midpoint due to the efficacy thereof and the fact that the body presents mechanisms for eliminating said compounds, thus reducing the risk of side effects (e.g., compounds with P—C—P bonds can present half-lives of several months which in vivo, thereby affecting, e.g., bone remodeling).

The term "alkyl" or "alkyl group" in the context of the present invention refers to a saturated hydrocarbon moiety, which can be linear, branched, cyclic or cyclic with linear or branched side chains. The term alkyl includes partially unsaturated hydrocarbons such as propenyl. Examples are methyl, ethyl, n- or isobutyl, n- or cyclohexyl. The term alkyl can extend to alkyl groups linked or bridged by hetero atoms. Hetero atoms in the context of the present invention are nitrogen (N), sulfur (S) and oxygen (O).

An "amine function" or "amine group" is a function NR'R", with R' and R" selected independently from hydrogen and $C_1$-$C_5$ alkyl. In some embodiments, R' and R" are selected from hydrogen and $C_1$-$C_3$ alkyl. A "hydroxy function" or "hydroxy group" is OH. A "thiol function" or "thiol group" is SH. A "carboxylic acid function" or "carboxylic acid group" is COOH or its anion, COO$^-$. A "carboxylic amide" is CONR'R", with R' and R" independently having the meanings indicated above. A "sulfonic acid" is $SO_3H$. A "sulfonic acid amide" is $SO_2NR'R"$, with R' and R" independently having the meanings indicated above.

A "$C_1$-$C_3$ alkyl" in the context of the present invention refers to a saturated linear or branched hydrocarbon having 1, 2 or 3 carbon atoms, wherein one carbon-carbon bond can be unsaturated and one $CH_2$ moiety can be exchanged for oxygen (ether bridge). Non-limiting examples for a $C_1$-$C_3$ alkyl are methyl, ethyl, propyl, prop-2-enyl and prop-2-inyl.

A "$C_1$-$C_5$ alkyl" in the context of the present invention refers to a saturated linear or branched hydrocarbon having 1, 2, 3, 4 or 5 carbon atoms, wherein one or two carbon-carbon bond can be unsaturated and one $CH_2$ moiety can be exchanged for oxygen (ether bridge). Non-limiting examples for a $C_1$-$C_5$ alkyl include the examples given for $C_1$-$C_3$ alkyl above, and additionally n-butyl, 2-methylpropyl, tert-butyl, 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, but-3-enyl, but-3-inyl and pent-4-inyl.

A "$C_3$-$C_{10}$ alkyl" in the context of the present invention refers to a saturated linear or branched hydrocarbon having 3, 4, 5, 6, 7, 8, 9 or 10 carbon atoms, wherein 1, 2 or 3 carbon-carbon bonds can be unsaturated and one $CH_2$ moiety can be exchanged for oxygen (ether bridge).

The term "$C_1$-30 alkyl," as a group or part of a group, refers to a linear or branched chain alkyl group containing between 1 and 30 carbon atoms including, amongst others, methyl, ethyl, propyl, isopropyl, butyl, isobutyl, sec-butyl, tert-butyl, pentyl, hexyl, decyl and dodecyl groups.

The term "$C_{2-30}$ alkenyl" refers to a linear or branched alkyl chain containing between 2 and 30 carbon atoms and also contains one or more double bonds. Examples include, amongst others, ethenyl, 1-propenyl, 2-propenyl, isopropenyl 1-butenyl, 2-butenyl, 3-butenyl and 1,3-butadienyl.

The term "$C_{2-30}$ alkynyl" refers to a linear or branched alkyl chain containing between 2 and 30 carbon atoms and also contains one or more triple bonds. Examples include, amongst others, ethynyl, 1-propynyl, 2-propynyl, 1-butynyl, 2-butynyl, 3-butynyl and 1,3-butadiynyl.

A "$Cy_1$ group" refers to a three- to 10-membered carbocyclic or heterocyclic ring that can be saturated, partially unsaturated or aromatic and which is bound to the rest of the molecule via any available C atom. When heterocyclic, $Cy_1$ contains between one and four heteroatoms selected from amongst N, O and S. Moreover, $Cy_1$ can optionally be fused with up to four five- or six-membered carbocyclic or heterocyclic rings, which can be saturated, partially unsaturated or aromatic.

If the fused ring is a heterocycle, said ring contains one or two heteroatoms selected from amongst N, O and S. Examples of $Cy_1$ include, amongst others, phenyl, naphthyl, thienyl, furyl, pyrrolyl, thiazolyl, isothiazolyl, imidazolyl, pyrazolyl, 1,2,3-triazolyl, 1,2,4-triazolyl, tetrazolyl, 1,3,4-thiadiazolyl, 1,2,4-thiadiazolyl, pyridyl, pyrazinyl, pyrimidinyl, pyridazinyl, benzimidazolyl, benzofuranyl, isobenzofuranyl, indolyl, isoindolyl, benzothiophenyl, benzothiazolyl, cyclopropyl, cyclobutyl, cyclopentyl, cyclohexyl, cycloheptyl, azetidinyl and aziridinyl.

A "$C_{1-30}$ alkoxy group," as a group or part of a group, refers to a $OC_{1-30}$alkyl group, where the $C_{1-30}$alkyl part has the same meaning as above. Examples include methoxy, ethoxy, propoxy, isopropoxy, butoxy, isobutoxy, sec-butoxy, and tert-butoxy.

A "$C_{1-30}$ alkylthionyl group" as a group or part of a group refers to an $SOC_{1-30}$alkyl group, where the $C_{1-30}$alkyl part has the same meaning as above. Examples include methylthionyl, ethylthionyl, propyithionyl, isopropyithionyl, butylthionyl, isobutyithionyl, sec-butylthionyl, and tert-butylthionyl.

A "$C_{1-30}$ acyloxy group" as a group or part of a group refers to a $COC_{1-30}$alkyl group, where the $C_{1-30}$alkyl part has the same meaning as above. Examples include acetyl, ethanoyl, propanoyl and 2,2-diisopropylpentanoyl.

A "halogen radical" or the halo abbreviation thereof refers to fluorine, chlorine, bromine, and iodine.

A "trihalo $C_{1-30}$ alkyl group" refers to a group resulting from the substitution of three hydrogen atoms of a $C_{1-30}$alkyl group by three halogen radicals as defined above. Examples include, amongst others, trifluoromethyl, tribromomethyl, trichloromethyl, triiodomethyl, trifluoroethyl, tribromoethyl, trichloroethyl, triiodoethyl, tribromopropyl, trichloropropyl, and triiodopropyl.

An "—$NHC_{1-30}$ alkyl group" refers to a group resulting from the substitution of one hydrogen atom of an $NH_2$ group by a $C_{1-30}$alkyl group as defined above. Examples include, amongst others, methylamine, ethylamine, propylamine, butylamine, and pentylamine.

An "$N(C_{1-30}alkyl)_2$ group" refers to a group resulting from the substitution of two hydrogen atoms of an $NH_2$ group by a $C_{1-30}$alkyl group as defined above. Examples include, amongst others, dimethylamine, diethylamine, diisopropylamine, dibutylamine, and diisobutylamine.

The expression "optionally substituted by one or more" signifies the possibility that a group can be substituted by one or more, e.g., by 1, 2, 3 or 4 substituents. In some aspects, a group can be substituted by 1, 2 or 3 substituents and even by 1 or 2 substituents provided that the group has sufficient positions that can be substituted available. If present, the substituents can be the same or different and can be located at any available position.

In some aspects, the inositol phosphates of the present invention used, e.g., in the methods of manufacture and compositions disclosed herein, comprise salts (e.g., sodium or potassium salts) of the compounds disclosed in WO2017098033 and WO2017098047, and U.S. Pat. No. 9,358,243.

In some aspects, the inositol phosphates, inositol phosphate analogs, and derivatives thereof used, e.g., in the methods and compositions disclosed herein, comprise compounds of formula (V), formula (VI) or formula (VII):

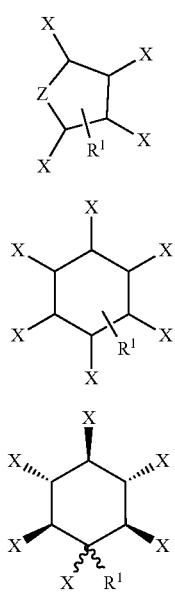

(V)

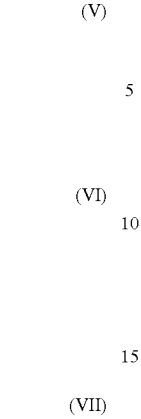

(VI)

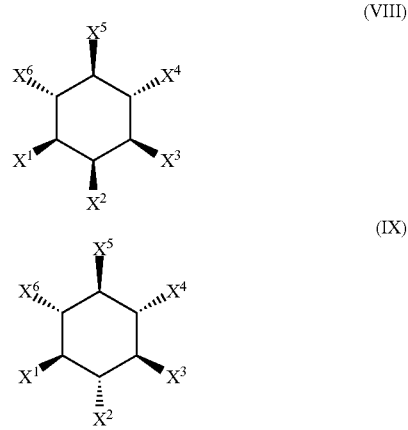

(VII)

(VIII)

(IX)

wherein each X independently is selected from $OPO_3^{2-}$, $OPSO_2^{2-}$ or $OSO_3$;

Z is an alkyl chain comprising 1 to 3 carbon and/or hetero atoms, optionally comprising a group X, wherein X is also selected from $OPO_3^{2-}$, $OPSO_2^{2-}$ or $OSO_3^-$; and, $R^1$ is an optional heterologous moiety. In some aspects, the molecule comprises more than one heterologous moiety, in which case the heterologous moieties can be the same or be different.

In some aspects, Z, as used in formula (V), is $CH_2$, CHX, $CHR^1$, $CXR^1$, $CH_2$—$CH_2$, $CH_2$—CHX, CHX—CHX, $CHR^1$—CHX, $CXR^1$—CHX, $CHR^1$—$CH_2$, $CXR^1$—$CH_2$, $CHR^1CHOH$, $CH_2$—$CH_2$—$CH_2$, $CH_2$—O—$CH_2$, CHOH—$CH_2$—$CH_2$, CHOH—CHOH—$CHR^1$, CHOH—$CHR^1CHOH$, CHX—$CH_2$—$CH_2$, $CH_2$—CHX—$CH_2$, CHX—CHX—$CH_2$, CHX—$CH_2$—CHX or CHX—$CHR^1$—CHX, wherein X independently is selected from $OPO_3^{2-}$, $OPSO_2^{2-}$, and $OSO_3^-$.

In some aspects, Z, as used in formula (V), is $(CHX)_p CHX(CHX)_q$; wherein p and q each independently from the other have a value from 0 to 2, with the proviso that (p+q) has a value of 0, 1 or 2; one or two or three X can be a heterologous moiety (e.g., PEG) and the remaining X are independently selected from $OPO_3^{2-}$, $OPSO_2^{2-}$, and $OSO_3^-$. In some aspects, not all X of Z are $OPO_3^{2-}$. In some aspects, not all X of Z are $SO_3^-$.

In some aspects, one, two or three of the X in compounds of formula (V), formula (VI) or formula (VII) can be heterologous moiety and the remaining X can independently be selected from $OPO_3^{2-}$ $OPSO_2^{2-}$ or $OSO_3^-$.

Formula (V) above describes a five-membered, six-membered or seven-membered alkyl ring, and the optional heterologous moiety or moieties is/are attached to one of the carbon atoms forming the ring.

In some aspects, the inositol phosphates, inositol phosphate analogs, and derivatives thereof used, e.g., in the methods of manufacture and compositions disclosed herein, comprise compounds of formula (VIII) or formula (IX):

wherein:
(a) $X^2$ is $OSO_3^-$, and $X^1$, $X^3$, $X^4$, $X^5$ and $X^6$ are independently selected from $PO_3^{2-}$, $OPSO_2^{2-}$ or $OSO_3^-$;
(b) $X^1$, $X^3$ and $X^5$ are $OPO_3^{2-}$ and $X^2$, $X^4$ and $X^6$ are $OSO_3^-$;
(c) $X^1$, $X^3$ and $X^5$ are $OSO_3^-$ and $X^2$, $X^4$ and $X^6$ are $OPO_3^{2-}$;
(d) $X^4$, $X^5$ and $X^6$ are $OSO_3^-$ and $X^1$, $X^2$ and $X^3$ are $OPO_3^{2-}$.
(e) $X^4$, $X^5$ and $X^6$ are $OPO_3^{2-}$ and $X^1$, $X^2$ and $X^3$ are $OSO_3^{2-}$;
(f) $X^2$ and $X^5$ are $OPO_3^{2-}$ and $X^1$, $X^3$, $X^4$, and $X^6$ are $OSO_3^-$;
(g) $X^2$ and $X^5$ are $OSO_3^{2-}$ and $X^1$, $X^3$, $X^4$, and $X^6$ are $OSO_3^{2-}$.
(h) $X^2$ and $X^3$ are $OPO_3^{2-}$ and $X^1$, $X^4$, $X^5$, and $X^6$ are $OSO_3^-$; or,
(i) $X^2$ and $X^3$ are $OSO_3^-$ and $X^1$, $X^4$, $X^5$, and $X^6$ are $OSO_3^{2-}$.

In some aspects, the inositol phosphates of the present invention (e.g., $Na_6IP_6$ prepared according to the methods disclosed herein) or metabolites thereof can be detected and/or quantified using the methods disclosed in U.S. Pat. No. 9,612,250. See also, U.S. Pat. Nos. 8,377,909, 8,778, 912, and US20070066574.

In some aspects, the inositol phosphates of the present invention (e.g., $Na_6IP_6$) are characterized for having a retention time of about 51.4 minutes for a phytic acid peak when an ion-exchange chromatography assay is performed.

The compounds disclosed herein (e.g., inositol phosphate salts prepared according to the methods disclosed herein) can be present in any form commonly used in pharmaceutical technology. Particular aspects include, but are not limited to, monovalent (e.g., sodium, potassium, ammonium) and divalent (e.g., magnesium) salts of inositol phosphate and the mixtures thereof. Other pharmaceutically acceptable salts are known to the person skilled in the art (Haynes D, et al., J. Pharmaceutical Sci. 2005; 94:2111-2120.

4. Pharmaceutical Compositions

The present invention also provides pharmaceutical compositions to treat diseases and conditions wherein, e.g., chelation of divalent ions is desirable. The pharmaceutical compositions provided herein can also be used, e.g., in the treatment or prevention of pathological calcifications, the treatment of diseases or conditions associated with pathological calcification (e.g., ectopic calcifications) or the treatment of sequelae, complications or symptoms of diseases or conditions wherein such sequelae, complications or symptoms are calcifications (e.g., calcification related to dialysis).

In some aspects, the pharmaceutical composition comprises at least one inositol phosphate of the present invention (e.g., $Na_6IP_6$ prepared according to the methods disclosed herein). In some aspects, the pharmaceutical composition comprises an inositol phosphate of the present invention (e.g., $Na_6IP_6$ prepared according to the methods disclosed herein) together with one or more pharmaceutically acceptable excipients or carriers.

The term "excipient" as used herein refers to a substance which helps absorption of the elements of the pharmaceutical composition, stabilizes said elements, activates or helps preparation of the composition. Thus, examples of excipients used in parenteral formulations include, but are not limited to, antimicrobial agents (e.g., benzalkonium chloride, metacresol, thimerosal), co-solvents (e.g., ethanol), buffers and pH adjusting factors (e.g., carbonate, citrate, phosphate solutions).

As is the case for the excipient, the "pharmaceutically acceptable vehicle" is a substance used in the composition to dilute any of the components contained therein to a determined volume or weight. The pharmaceutically acceptable vehicle is an inert substance or a substance with an analogous action to any of the elements comprising the pharmaceutical composition of the present invention. The role of said vehicle is to allow the incorporation of other elements, allow better dosing and administration or to provide consistency and shape to the composition.

Pharmaceutical compositions can comprise from approximately 0.001% to approximately 95% active ingredient (e.g., $Na_6IP_6$ prepared according to the methods disclosed herein, alone or in a combination formulation, e.g., with one or more therapeutic agents disclosed in Table 1). In some aspects, e.g., the pharmaceutical compositions of the present invention can comprise from approximately 20% to approximately 90% active ingredient (e.g., $Na_6IP_6$ prepared according to the methods disclosed herein, alone or in a combination formulation, e.g., with one or more therapeutic agents disclosed in Table 1).

In some aspects, the concentration of inositol phosphate of the present invention (e.g., $Na_6IP_6$, $K_6IP_6$, $(NH_4)_6IP_6$) in the aqueous pharmaceutical composition is between about 0.001 mg/mL and about 100 mg/mL. In one specific aspect, the concentration of inositol phosphate of the present invention (e.g., $Na_6IP_6$, $K_6IP_6$, $(NH_4)_6IP_6$) in the aqueous pharmaceutical composition is between about 20 mg/mL and about 90 mg/mL.

In one specific aspect, the concentration of inositol phosphate of the present invention (e.g., $Na_6IP_6$, $K_6IP_6$, $(NH_4)_6IP_6$) in the aqueous pharmaceutical composition is about 20 mg/mL. In another specific aspect, the concentration of inositol phosphate of the present invention (e.g., $Na_6IP_6$, $K_6IP_6$, $(NH_4)_6IP_6$) in the aqueous pharmaceutical composition is about 30 mg/mL. In yet another specific aspect, the concentration of inositol phosphate of the present invention (e.g., $Na_6IP_6$, $K_6IP_6$, $(NH_4)_6IP_6$) in the aqueous pharmaceutical composition is about 90 mg/mL.

In some aspects, the concentration of inositol phosphate of the present invention (e.g., $Na_6IP_6$, $K_6IP_6$, $(NH_4)_6IP_6$) in the aqueous pharmaceutical composition is about 10 mg/mL, about 20 mg/mL, about 30 mg/mL, about 40 mg/mL, about 50 mg/mL, about 60 mg/mL, about 70 mg/mL, about 80 mg/mL, about 90 or about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 20 mg/mL and about 100 mg/mL, between about 30 mg/mL and about 100 mg/mL, between about 40 mg/mL and about 100 mg/mL, between about 50 mg/mL and about 100 mg/mL, between about 60 mg/mL and about 100 mg/mL, between about 70 mg/mL and about 100 mg/mL, between about 80 mg/mL and about 100 mg/mL or between about 90 mg/mL and about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 20 mg/mL, between about 10 mg/mL and about 30 mg/mL, between about 10 mg/mL and about 40 mg/mL, between about 10 mg/mL and about 50 mg/mL, between about 10 mg/mL and about 60 mg/mL, between about 10 mg/mL and about 70 mg/mL, between about 10 mg/mL and about 80 mg/mL or between about 10 mg/mL and about 90 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 20 mg/mL, between about 20 mg/mL and about 30 mg/mL, between about 30 mg/mL and about 40 mg/mL, between about 40 mg/mL and about 50 mg/mL, between about 50 mg/mL and about 60 mg/mL, between about 60 mg/mL and about 70 mg/mL, between about 70 mg/mL and about 80 mg/mL, between about 80 mg/mL and about 90 mg/mL or between about 90 mg/mL and about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 30 mg/mL, between about 20 mg/mL and about 40 mg/mL, between about 30 mg/mL and about 50 mg/mL, between about 40 mg/mL and about 60 mg/mL, between about 50 mg/mL and about 70 mg/mL, between about 60 mg/mL and about 80 mg/mL, between about 70 mg/mL and about 90 mg/mL or between about 80 mg/mL and about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 40 mg/mL, between about 20 mg/mL and about 50 mg/mL, between about 30 mg/mL and about 60 mg/mL, between about 40 mg/mL and about 70 mg/mL, between about 50 mg/mL and about 80 mg/mL, between about 60 mg/mL and about 90 mg/mL or between about 70 mg/mL and about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 50 mg/mL, between about 20 mg/mL and about 60 mg/mL, between about 30 mg/mL and about 70 mg/mL, between about 40 mg/mL and about 80 mg/mL, between about 50 mg/mL and about 90 mg/mL or between about 60 mg/mL and about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 60 mg/mL, between about 20 mg/mL and about 70 mg/mL, between about 30 mg/mL and about 80 mg/mL, between about 40 mg/mL and about 90 mg/mL or between about 50 mg/mL and about 100 mg/mL of inositol phosphate of the present invention.

In some aspects, the concentration of inositol phosphate of the present invention (e.g., $Na_6IP_6$, $K_6IP_6$, $(NH_4)_6IP_6$) in the aqueous pharmaceutical composition is between about 10 mg/mL and about 55 mg/mL or between about 55 mg/mL and about 100 mg/mL of inositol phosphate of the present invention.

In some aspects, the pharmaceutical compositions of the present invention (e.g., containing $Na_6IP_6$) are characterized for having a retention time of about 51 minutes for a phytic acid peak when an ion-exchange chromatography assay is performed.

In some aspects, the present invention is directed to a pharmaceutical composition comprising: (a) about 10 mg/mL to about 100 mg/mL of $Na_6IP_6$, (b) about 0.001 mg/mL to 50 mg/mL of at least one tonicity agent, and (c) water. Said composition is characterized for being a stable solution (i.e., 25° C., 60% RH). In some aspects, the composition further comprises a pH buffer solution.

In some aspects, the $Na_6IP_6$ of the composition is characterized for being at least 70% (w/w) pure and comprising: (i) DL-Inositol 1,2,3,4,6-pentaphosphate≤2.0% (w/w), (ii) DL-Inositol 1,2,3,5,6-pentaphosphate≤4.0% (w/w), (iii) DL-Inositol 1,2,4,5,6-pentaphosphate≤5.0% (w/w), and (iv) DL-Inositol 1,3,4,5,6-pentaphosphate≤3.0% (w/w). In some aspects, the $Na_6IP_6$ of the composition is characterized for being at least 80% (w/w) pure and comprising: (i) DL-Inositol 1,2,3,4,6-pentaphosphate≤1.4% (w/w), (ii) DL-Inositol 1,2,3,5,6-pentaphosphate≤2.1% (w/w), (iii) DL-Inositol 1,2,4,5,6-pentaphosphate≤2.6% (w/w), and (iv) DL-Inositol 1,3,4,5,6-pentaphosphate≤0.52% (w/w). In some aspects, the $Na_6IP_6$ of the composition is obtained according to the methods disclosed herein.

In some aspects, the composition comprises about 20 mg/mL to about 90 mg/mL of $Na_6IP_6$. In some additional aspects, the composition comprises about 20 mg/mL, about 30 mg/mL or about 90 mg/mL of $Na_6IP_6$.

Examples of tonicity agents used in the pharmaceutical compositions of the invention include, but are not limited to dextrose, glycerin, and sodium chloride or a combination thereof. In some aspects, the agent is an aqueous solution about 0.01 mg/mL to about 10 mg/mL of sodium chloride. In some further aspects, the agent is an aqueous solution about 9 mg/mL of sodium chloride.

Examples of pH buffer solutions used in the pharmaceutical compositions of the invention include, but are not limited to citric acid, disodium phosphate dihydrate, sodium hydroxide, sodium dihydrogen phosphate dihydrate, and combinations thereof. In some aspects, the pH of the composition is of about 5.0 to about 7.0, at 25° C. as measured according to Ph. Eur. 2.2.3. In some aspects, the pH of the liquid composition is of about 5.5 to about 6.5, at 25° C. as measured according to Ph. Eur. 2.2.3. In some aspects, the pH buffer solution used in the composition is a sodium hydroxide solution having a pH of 5.0 to about 7.0, at 25° C. as measured according to Ph. Eur. 2.2.3. Formulations of a pharmaceutical composition suitable for parenteral administration comprise the active ingredient, e.g., an inositol phosphate of the present invention, combined with a pharmaceutically acceptable carrier, such as sterile water or sterile isotonic saline. Such formulations can be prepared, packaged or sold in a form suitable for bolus administration or for continuous administration. Injectable formulations can be prepared, packaged or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing or dispersing agents.

In some aspects, in a formulation for parenteral administration, the active ingredient, (e.g., $Na_6IP_6$ prepared according to the methods disclosed herein), is provided in dry (i.e., powder or granular) form for reconstitution with a suitable vehicle (e.g., water for injection) prior to parenteral administration of the reconstituted composition.

The pharmaceutical compositions can be prepared, packaged or sold in the form of a sterile injectable aqueous suspension or solution. This suspension or solution can be formulated according to the known art, and may comprise, in addition to the active ingredient (e.g., $Na_6IP_6$ prepared according to the methods disclosed herein, alone or in a combination formulation, e.g., with one or more therapeutic agents disclosed in Table 1), additional ingredients such as the dispersing agents, wetting agents or suspending agents described herein. Such sterile injectable formulations can be prepared using a non-toxic parenterally-acceptable diluent or solvent, such as water. Other acceptable diluents and solvents include, but are not limited to, Ringer's solution and isotonic sodium chloride solution.

Other parentally-administrable formulations which are useful include those which comprise the active ingredient in microcrystalline form, in a liposomal preparation or as a component of a biodegradable polymer system. Compositions for sustained release or implantation can comprise pharmaceutically acceptable polymeric or hydrophobic materials such as an emulsion, an ion exchange resin, a sparingly soluble polymer or a sparingly soluble salt.

Controlled- or sustained-release formulations of a pharmaceutical composition of the present invention (e.g., pharmaceutical composition comprising $Na_6IP_6$ prepared according to the methods disclosed herein, alone or in a combination formulation, e.g., with one or more therapeutic agents disclosed in Table 1) can be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes or microspheres or a combination thereof to provide the desired release profile in varying proportions.

Suitable controlled-release formulations known to those skilled in the art, including those described herein, can be readily selected for use with the pharmaceutical compositions of the invention. Thus, single unit dosage forms suitable for parenteral or topical administration, such as injectable solutions, gels, creams, and ointments, which are adapted for controlled-release are encompassed by the present invention.

Most controlled-release pharmaceutical products have a common goal of improving therapy over that achieved by their non-controlled counterparts. Ideally, the use of an optimally designed controlled-release preparation in medical treatment is characterized by a minimum of therapeutic agent being employed to cure or control the condition in a minimum amount of time. Advantages of controlled-release formulations include extended activity of the therapeutic agent, reduced dosage frequency, and increased patient compliance. In addition, controlled-release formulations can be used to affect the time of onset of action or other characteristics, such as blood level of the therapeutic agent, and thus can affect the occurrence of side effects.

Most controlled-release formulations are designed to initially release an amount of therapeutic agent that promptly produces the desired therapeutic effect, and gradually and continually release of other amounts of therapeutic agent to maintain this level of therapeutic effect over an extended period of time. In order to maintain this constant level of therapeutic agent in the body, the therapeutic agent must be released from the dosage form at a rate that will replace the amount of therapeutic agent being metabolized and excreted from the body.

Controlled-release of an active ingredient can be stimulated by various inducers, for example pH, temperature, enzymes, water or other physiological conditions or compounds. The term "controlled-release component" in the context of the present invention is defined herein as a compound or compounds, including, but not limited to, polymers, polymer matrices, gels, permeable membranes, liposomes or microspheres or a combination thereof that facilitates the controlled-release of the active ingredient.

In certain aspects, the formulations of the present invention can be, but are not limited to, short-term, rapid-offset, as well as controlled, for example, sustained release, delayed release and pulsatile release formulations.

The term sustained release is used in its conventional sense to refer to a therapeutic agent formulation (e.g., pharmaceutical composition comprising $Na_6IP_6$ prepared according to the methods disclosed herein, alone or in a combination formulation, e.g., with one or more therapeutic agents disclosed in Table 1) that provides for gradual release of a therapeutic agent over an extended period of time, and that can, although not necessarily, result in substantially constant blood levels of a therapeutic agent over an extended time period. The period of time can be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the present invention can be administered in the form of microparticles, for example, by injection or in the form of wafers or discs by implantation. In certain aspects, the compounds of the invention are administered to a patient, alone or in combination with another pharmaceutical agent, using a sustained release formulation.

The term delayed release is used herein in its conventional sense to refer to a therapeutic agent formulation that provides for an initial release of the therapeutic agent after some delay following therapeutic agent administration. The delay may be from about 10 minutes up to about 12 hours. The term pulsatile release is used herein in its conventional sense to refer to a therapeutic agent formulation that provides release of the therapeutic agent in such a way as to produce pulsed plasma profiles of the therapeutic agent after administration. The term immediate release is used in its conventional sense to refer to a therapeutic agent formulation that provides for release of the therapeutic agent immediately after administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes or about 10 minutes and any or all whole or partial increments thereof after therapeutic agent administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes or about 10 minutes, and any and all whole or partial increments thereof after therapeutic agent administration.

Additional formulations and dosage forms of the compositions of the present invention include dosage forms as described in U.S. Pat. Nos. 6,340,475, 6,488,962, 6,451,808, 5,972,389, 5,582,837, and 5,007,790. See also, U.S. Ser. No. 00/301,47952, US20030104062, US20030104053, US20030044466, US20030039688, and US20020051820; WO200335041, WO200335040, WO200335029, WO200335177, WO2003035039, WO2002096404, WO2002032416, WO2001097783, WO2001056544, WO2001032217, WO1998055107, WO1998011879, WO1997047285, WO1993018755, and WO1990011757.

Medicaments comprising inositol phosphates prepared according to the methods of the invention can be manufactured by methods known in the art, especially by conventional mixing, coating, granulating, dissolving or lyophilizing.

The present invention also provides a compound, combinations of compounds or pharmaceutical formulations according to any of the above aspects of the invention, in the broadest definition given or as specified in any of the aspects presented above, for use as a medicament.

The present invention also provides a compound, combination of compounds or pharmaceutical formulation according to any of the above aspects of the invention, in the broadest definition given or as specified in any of the aspects presented above, for use in the treatment and/or prevention of a disease or condition disclosed herein (e.g., pathological calcification).

The present invention also provides a compound or combination of compounds or pharmaceutical formulation according to any of the above aspects of the invention, in the broadest definition given or as specified in any of the aspects presented above, for the manufacture of a medicament for the prevention and/or treatment of a disease or condition disclosed herein.

In some aspects, the compositions disclosed herein can be used as nutraceuticals or as components of functional foods.

5. Combinations

The present invention also provides combination treatments comprising the administration of an inositol phosphate of the invention (e.g., $Na_6IP_6$ prepared according to the methods disclosed herein) and at least one additional therapeutic agent. Also provided are combined compositions comprising an inositol phosphate of the invention (e.g., $Na_6IP_6$ prepared according to the methods disclosed herein) and at least one additional therapeutic agent. Thus, a further aspect of the present invention relates to a composition comprising at least one inositol phosphate of the invention (e.g., $Na_6IP_6$ prepared according to the methods disclosed herein) and another therapeutic agent.

The "term "combination therapy" as used herein refers interchangeably to both combination treatments according to the methods and dosages disclosed herein, and to combined compositions. As used herein the term "combined composition" does not imply the components of the combined composition need to be present together. Consequently, the expression implies that the combination is not necessarily a true combination in light of the physical separation of the components thereof. For example, the components in a combined composition can be applied separately, sequentially or their application can overlap.

In some aspects, the additional therapeutic agent is selected, e.g., from the compositions presented in Table 1. In some aspects, a combination therapy can comprise an inositol phosphate of the invention (e.g., $Na_6IP_6$ prepared according to the methods disclosed herein) and a therapeutic agent from Table 1. In other aspects, a combination therapy can comprise an inositol phosphate of the invention (e.g., $Na_6IP_6$ prepared according to the methods disclosed herein) and more than one therapeutic agent from Table 1. When more than one therapeutic agent from Table 1 is present in a combination therapy, the therapeutic agents from Table 1 can belong to the same indication or to different indications. For example, a combination composition can comprise a treatment (e.g., OPG), a wound healing compound, and a pain management compound.

In some aspects, the combination composition comprises a vitamin selected from vitamin B, vitamin D, vitamin K or a combination thereof Although with a different mechanism of action, vitamin D has a similar effect. The vitamin D is preferably selected from the group consisting of calciferol, ergocalciferol (Vitamin D2), cholecalciferol (Vitamin D3), doxercalciferol, paricalcitol alfarol, alpha-calcidol calcidiol, calcitriol, derivatives or pharmaceutically acceptable salts thereof or any combinations thereof.

Phosphate binders act by sequestering phosphate thereby reducing the systemic concentration thereof in blood. The phosphate binder can contain a metal or be metal-free. Metal-free chelators include, e.g., sevelamer. Metal-containing chelators include, e.g., various calcium, iron, lanthanum,

TABLE 1

Exemplary therapeutic agents that can be combined with the inositol phosphates of the present invention (e.g., $Na_6IP_6$ prepared according to the methods disclosed herein)

| Indication | Therapeutic agent(s) to combine with IP salt(s) of the invention |
| --- | --- |
| Treatment | Osteoprotegerin (OPG)<br>Corticosteroids<br><br>Group A (hydrocortisone, hydrocortisone, methylprednisolone, prednisolone, prednisone, triamcinolone)<br>Group B (amcinonide, budesonide, desonide, fluocinolone acetonide, fluocinonide, halcinonide, triamcinolone acetonide)<br>Group C (beclometasone, betamethasone, dexamethasone, fluocortolone, halometasone, mometasone)<br>Group D1 (alclometasone dipropionate, betamethasone dipropionate, betamethasone valerate, clobetasol propionate, clobetasone butyrate, fluprednidene acetate, mometasone furoate)<br>Group D2 (ciclesonide, cortisone acetate, hydrocortisone aceponate, hydrocortisone acetate, hydrocortisone buteprate, hydrocortisone butyrate, hydrocortisone valerate, prednicarbate, tixocortol pivalate)<br>Fetuin-alpha<br>Vitamin (vitamin A, vitamin B, vitamin C, vitamin D, vitamin K)<br>Protein C<br>Protein S<br>Gla Protein Matrix (MGP)<br>Hyperbaric medicine<br>Calcimimetics (Cinacalcet CAS [226256-56-0], NPS R-467, NPS R-568, KAI-4169)<br>Phosphate binders (Sevelamer CAS [52757-95-6], lanthanum carbonate, sucroferric oxyhydroxide, calcium acetate, calcium acetate/magnesium carbonate, calcium carbonate)<br>Bisphosphonates (etidronate, pamidronate), sodium thiosulfate, other C-O-P compounds<br>Other ectopic calcification inhibitors |
| Wound healing | Gram positive antibiotics (gloxacillin, amoxicillin plus clavulanic acid, piperacillin-tazobactam, daptomycin)<br>Anaerobic germs antibiotics (metronidazole, clindamycin) |
| Pain management | Analgesics in general that are not easily dialyzed<br>Opioids (buprenorphine, fentanyl, methadone) |
| General analgesia | GBA analogs (gabapentin)<br>Central pain modulators (amitriptyline, duloxetine) |
| Pain management | Lidocaine<br>Morphine infusion gels |
| Topical analgesia | |

Several of the compounds described as additional therapeutic agents change the thermodynamics of the crystallization process by modifying the concentration of the ions present in the structure of the calcium-containing crystal that results in an ectopic calcification. This sub-group includes calcimimetics, phosphate chelators, thiosulfate or vitamin D.

Calcimimetics allow the calcium and phosphate concentration to be controlled by regulating blood PTH levels. Said compounds include, e.g., cinacalcet, NPS R-467, NPS R-568, and KAI-4169.

aluminum, and magnesium salts. Thiosulfate is a chelator that reduces the free calcium concentration in blood.

Other compounds (e.g., pyrophosphate, citrate, bisphosphonates, antihypertensives, anticholesteremic agents, vitamin B or vitamin K) that can be used in combination therapies act against the altered calcium and phosphate metabolism kinetically by attempting to stop the crystallization process or altering bone metabolism by increasing the amount of repressor factors (pyrophosphate, citrate, vitamin B, vitamin K, bisphosphonates) or by reducing the quantity of promoter factors (necrotic remains or organic matter in the case of antihypertensives or lipid deposits in the case of anticholesteremic agents).

In some aspects, the bisphosphonate can contain nitrogen or be nitrogen-free. In some aspects, the bisphosphonate can be selected from the group consisting of etidronate, alendronate, risedronate, zoledronate, tiludronate, pamidronate, monidronate, neridronate, pamidronate, olpadronate, clodronate, ibandronate, and combinations thereof.

In some aspects, the combination therapy can comprise an anticholesteremic agent selected from the group consisting of statins, fibrates, niacin, acid sequestrants, ezetimibe, lomitapide, phytosterols orlistat, and combinations thereof.

Compounds that can be also used for the treatment of ectopic calcifications also include those disclosed in U.S. Pat. No. 9,629,872, WO2017131127, U.S. Pat. Nos. 5,362,886, 4,024,175, and 3,159,581.

6. Articles of Manufacture and Kits

The present invention also provides articles of manufacture and kits comprising an inositol phosphate of the present invention (e.g., $Na_6IP_6$ prepared according to the methods disclosed herein). Such articles of manufacture and kits can comprise a container (e.g., a box) comprising one or more vials containing a formulation comprising one or more of the salts of inositol hexaphosphate (e.g., $Na_6IP_6$) disclosed herein and/or solvents for their administration according to the methods disclosed herein.

A kit or article of manufacture provided according to this invention can also comprise brochures or instructions describing the process of administration and dosages disclosed herein. In some aspects, kit or article of manufacture can comprise multiple vials, each one of them containing a single dose. In other aspects, kits or article of manufacture can comprise one or more vials, each one of them comprising more than one dose.

In some aspects, the article of manufacture is a bag or syringe containing a solution prepared by dissolving a salt of inositol hexaphosphate (e.g., $Na_6IP_6$) disclosed herein. In other aspects, the article of manufacture is a bottle (e.g., a glass bottle or a plastic bottle) containing a solution prepared by dissolving a salt of inositol hexaphosphate (e.g., $Na_6IP_6$) disclosed herein.

In some aspects, the article of manufacture is a bag containing a salt of inositol hexaphosphate (e.g., $Na_6IP_6$) disclosed herein in powder form for reconstitution in an appropriate solvent. In other aspects, the article of manufacture is a bottle (e.g., a glass bottle or a plastic bottle) containing a salt of inositol hexaphosphate (e.g., $Na_6IP_6$) disclosed herein in powder form for reconstitution in an appropriate solvent.

The kits and articles of manufacture can include instructions for carrying out one or more administrations of a salt of inositol hexaphosphate (e.g., $Na_6IP_6$) disclosed herein prepared according to the methods disclosed herein.

Instructions included in the kits and articles of manufacture can be affixed to packaging material or can be included as a package insert. While the instructions are typically written or printed, materials are not limited to such. Any medium capable of storing such instructions and communicating them to an end user is contemplated. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

7. Methods of Treatment and Uses

The present invention also provides methods for treating or preventing ectopic calcification or its consequences in a subject in need thereof which comprises administering a compound prepared according to the process of any one of claims, a soluble IP salt prepared according to the methods disclosed herein (e.g., $Na_6IP_6$), a pharmaceutical composition disclosed herein, a combination treatment disclosed herein or a kit disclosed herein to the subject. Alternatively, the present invention provides a compound prepared according to the process of any one of claims, a soluble IP salt prepared according to the methods disclosed herein (e.g., $Na_6IP_6$), a pharmaceutical composition disclosed herein, a combination treatment disclosed herein or a kit disclosed for use in the treatment or prevention of ectopic calcification or its consequences in a subject in need thereof. Alternatively, the present invention provides the use of a compound prepared according to the process of any one of claims, a soluble IP salt prepared according to the methods disclosed herein (e.g., $Na_6IP_6$), a pharmaceutical composition disclosed herein, a combination treatment disclosed herein or a kit disclosed herein in the preparation of a medicament for treating or preventing ectopic calcification or its consequences in a subject in need thereof. In some aspects, the subject is undergoing hemodialysis. In some aspects, the subject has end-stage renal disease. In some aspects, the soluble IP salt, pharmaceutical composition, combination treatment or kit disclosed herein comprises a salt of inositol hexaphosphate (e.g., $Na_6IP_6$) prepared according to the methods disclosed herein.

In some aspects, the salt of inositol hexaphosphate (e.g., $Na_6IP_6$) disclosed herein can be used to treat and/or present pathological calcifications, e.g., ectopic calcification such as calciphylaxis, and/or the consequences thereof in a subject. In some aspects, the salt of inositol hexaphosphate (e.g., $Na_6IP_6$) disclosed herein can be administered in at least one dose in a dosage of about 5 mg to 10 mg per kg per administration to the subject (e.g., a dosage of about 6 mg/kg to about 9 mg/kg, such as 6 mg/kg or 9 mg/kg), at least one per week (e.g., once, twice or three times per week), for a variable period of time (e.g., from about 1 week to about 12 weeks, about 24 weeks or about 52 weeks) or chronically wherein the administration of the dosage effectively treats and/or prevents the pathological calcification, e.g., ectopic calcification such as calciphylaxis, and/or the consequences thereof in the subject.

In some aspects, the inositol phosphates of the present invention can be administered by any appropriate method such as parenteral (e.g., subcutaneous, subcutaneous depot, intraperitoneal, intramuscular, intradermal, intrathecal, epidural, spinal, intravascular, intravenous, intravenous infusion), topical, (e.g., intranasal, inhalation, intravaginal, transdermal), enteral (e.g., oral, sublingual, rectal) or others known to a person skilled in the art. In some aspects, the inositol phosphates of the present invention can be administered by a method that provokes a non-bolus type release or effect in the subject.

In a particular aspect of the present invention, a myo-inositol hexaphosphate (or a formulation comprising a hexasodium salt of myo-inositol hexaphosphate such as SNF472) prepared according to the methods disclosed herein is administered intravenously via intravenous infusion. In another particular aspect of the present invention, a myo-inositol hexaphosphate prepared according to the methods disclosed herein (e.g., $Na_6IP_6$) is administered subcutaneously. In another particular aspect of the present invention, a myo-inositol hexaphosphate prepared according to the methods disclosed herein (e.g., $Na_6IP_6$) is administered topically.

In some aspect, when an inositol phosphate of the present invention (e.g., $Na_6IP_6$) is administered to a patient undergoing dialysis, such administration (e.g., intravenous administration via infusion) can occur during a dialysis treatment.

In some aspects, the administration of the dosage of inositol phosphate of the present invention (e.g., $Na_6IP_6$) to the subject inhibits the formation and/or growth of hydroxyapatite crystals, e.g., on teeth, and their deposition in ectopic calcifications, e.g., in calciphylaxis calcification. In some aspects, the ectopic calcification is, e.g., a calciphylaxis calcification, a metastatic calcification, a dystrophic calcification, an iatrogenic calcification, an idiopathic calcification or a subcutaneous ectopic ossification.

In some aspects, the consequence of the ectopic calcification is, e.g., (i) a functional complication, (ii) pain, (iii) a trophic complication, (iv) an infection or (v) a combination thereof. In some aspects, the function complication is, e.g., a limitation of range of motion and/or joint function. In some aspects, the trophic complication is, e.g., ischemia and/or a lesion. In some aspects, the lesion is, e.g., necrosis of the cutaneous and/or subcutaneous tissues.

The methods, compositions, pharmaceutical compositions and formulations, articles of manufacture and kits comprising inositol phosphates of the present invention disclosed herein, can be used to treat and/or prevent ectopic calcifications, and in particular cutaneous or subcutaneous calcification such as calciphylaxis calcifications, and/or the consequences thereof in a subject in need thereof.

Cutaneous and subcutaneous calcifications (in general referred to as ectopic calcifications) are related to the pathological crystallization of calcium and arise as complications in numerous diseases. Ectopic calcifications can be classified into dystrophic, metastatic, idiopathic or iatrogenic calcifications or into calciphylaxis.

Dystrophic calcifications result from local tissue abnormalities and grow in spite of normal plasma calcium and phosphorus levels. The main diseases that can develop due to these calcifications are: connective tissue diseases (e.g., scleroderma, CREST syndrome, juvenile dermatomyositis, lupus), cutaneous and subcutaneous infections (e.g., panniculitis), skin tumors (in particular pilomatricoma), certain congenital diseases (e.g., Elher-Danlos disease, Werner's syndrome, pseudo xanthoma elasticum (PXE)).

Metastatic calcifications are the result of a disorder of calcium and phosphate metabolism (hypercalcemia and/or hyperphosphatemia). All diseases that cause these disorders can therefore contribute to the development of calcifications.

Idiopathic calcifications occur without tissue lesions or disorders of calcium and phosphate metabolism. The main known diseases in this group are tumoral calcinosis, scrotal calcifications as well as sub-epidermal calcified nodules.

Iatrogenic calcifications can occur following the injection of calcium or para-aminosalycylic acid. They have also been described following the use of calcium chloride saturated electrodes.

Soft tissue calcifications (e.g., cutaneous or subcutaneous calcifications) can be associated with a disease or pathological condition selected from the group consisting of primary hyperparathyroidism, vitamin D intoxication, milk drinker's syndrome, hypercalcemia, secondary hyperparathyroidism, renal failure, hyperphosphatemia, in particular genetic hyperphosphatemia, scleroderma, dermatomyositis, in particular the juvenile form, mixed connective tissue diseases, lupus, CREST syndrome, Elhers-Danlos syndrome, PXE, Werner's syndrome, late cutaneous *porphyria*, pseudo hypoparathyroidism, pseudo pseudo-hypoparathyroidism, (primary or secondary) venous or arterial insufficiency, diabetes, scrotal calcinosis, ossifying myositis, post-traumatic ectopic ossifications and any other disease or pathological condition caused by calcium crystal deposit(s), in particular of hydroxyapatite or calcium pyrophosphate, e.g., calciphylaxis.

An important concept is that various disorders, including those listed in the previous paragraphs, can be treated by preventing, reducing, slowing or stopping the progression of calcification in the presence of uremia. The disease related to calcium disorders or the calcification induced by said disease, can already be present when administration commences, in order to reduce or stop progression of the disease or cannot yet be present, in order to prevent the appearance or onset of the disease.

Calciphylaxis corresponds to the calcification of small sized blood vessels and of the sub-cutaneous adipose tissue. Calciphylaxis can be treated concurrently with at least the following diseases: hypercalcemia, hyperphosphatemia, secondary and tertiary hyperparathyroidism, hypoparathyroidism or any combination thereof.

Further conditions that can benefit from a treatment with the inositol phosphates of the invention (e.g., $Na_6IP_6$ prepared according to the methods disclosed herein), peripheral arterial disease, critical limb ischemia, general arterial calcification of infancy, aortic valve stenosis, atherosclerosis, pseudo gout, primary hyperoxaluria, and pseudoxanthoma elasticum.

In the context of the present invention, "peripheral arterial disease" refers to a narrowing of the peripheral arteries to the legs (most commonly), stomach, arms, and head. Symptoms include intermittent claudication (leg pain when walking which resolves with rest), skin ulcers, bluish skin, cold skin or poor nail and hair growth.

In the context of the present invention, "critical limb ischemia" refers to a severe obstruction of the arteries which markedly reduces blood flow to the extremities and progresses to the point of severe pain and even skin ulcers, sores or gangrene. Critical limb ischemia is a very severe condition of peripheral artery disease.

In the context of the present invention, "pseudogout", also known as "Calcium pyrophosphate dihydrate (CPPD) crystal deposition disease" or "pyrophosphate arthropathy" refers to a rheumatologic disorder believed to be caused by calcium pyrophosphate crystal accumulation in connective tissues, particularly joints such as the knee joint.

In the context of the present invention, the term "general arterial calcification of infancy" (GACI) relates to a disorder affecting the circulatory system that becomes apparent before birth or within the first few months of life, and which is characterized by abnormal calcification of the arteries and thickening of the arterial walls. These changes lead to stenosis and stiffness of the arteries, resulting in heart failure in some affected individuals, with signs and symptoms including difficulty breathing, edema, cyanosis, hypertension, and cardiomegaly.

In some aspects, the administration of the dosage of inositol phosphate of the present invention (e.g., $Na_6IP_6$), can be used to treat a bacterial infection, e.g., a *Clostridium difficile* infection. In some aspects, the inositol phosphates of the present invention (e.g., $Na_6IP_6$) can be administered as nutraceuticals or functional foods.

In some aspects, an inositol phosphate of the present invention (e.g., $Na_6IP_6$ prepared according to the methods disclosed herein) can be used, e.g., as an antioxidant or as a medicament to reduce or inhibit atherosclerotic plaque formation, reduce inflammation, lower cholesterol and/or triglycerides, reduce arterial obstruction, reduce arterial inflammation, reduce heart disease, reduce or inhibit platelet aggregation or decrease insulin resistance in type II diabetes affected patients.

The following examples present improved synthesis processes for the synthesis of the active substance in SNF472 (hexasodium phytate), as well as intermediates (e.g., $Na_{12}IP_6$) and variants thereof (e.g., $K_{12}IP_6$ or $K_6IP_6$). The processes provided below are exceedingly efficient and result in a final product with a high degree of purity.

Example 1

Purification Process Development

Screening of solvent combinations for recrystallization: The first experiments focused on $Na_{12}IP_6$ crystallization methods with precipitation from water by addition of an antisolvent. The advantage of these methods was that no heating above room temperature was required. No solvent combination or precipitation mode recrystallized phytate. In all experiments oiling/formation of sticky material was observed. Furthermore, analytical data showed no significant purification effect. See Table 4.

TABLE 4

Screening of antisolvent combinations for recrystallization

| Anti-solvent | Temp. | Addition Mode | Seeding | Impurities IC | Yield | Variation |
|---|---|---|---|---|---|---|
| EtOH | RT | normal | no | Not measured | 90% | |
| Acetone | RT | normal | no | Not measured | 90% | |
| MeOH | RT | normal | no | 6.1% | 90% | |
| Acetone | RT | reversed | no | Not measured | 99% | |
| MeOH | RT | reversed | no | Not measured | 89% | |
| Acetone | RT | reversed | yes | 7.2% | 93% | |
| MeOH | RT | reversed | yes | 6.7% | 88% | |
| EtOH | RT | reversed | yes | 6.0% | 91% | |
| MeOH | RT | normal | no | Not measured | 30% | slow addition |

TABLE 4-continued

Screening of antisolvent combinations for recrystallization

| Anti-solvent | Temp. | Addition Mode | Seeding | Impurities IC | Yield | Variation |
|---|---|---|---|---|---|---|
| MeOH | 5° C. | normal | yes | 6.3% | 90% | |
| MeCN | 5° C. | normal | yes | Not measured | 92% | |
| 1,4-Dioxane | 5° C. | normal | yes | Not measured | 21% | |
| THF | 5° C. | normal | yes | Not measured | 27% | |
| 2-Propanol | 5° C. | normal | yes | 6.2% | 88% | |
| MeCN | 5° C. | normal | yes | 4.4% | 85% | less MeCN |
| MeOH | 5° C. | normal | yes | 6.3% | 84% | cold filtration |

Recrystallization from water: After the first unsuccessful recrystallization attempts with precipitation by addition of an antisolvent, an alternative method was required. Direct recrystallization from water was investigated. Initial stability tests in water at 50° C. for 3 days showed no significant decomposition by $^{31}$P-NMR. A significant purification effect was achieved with this recrystallization procedure. See Table 5.

TABLE 5

Screening for conditions for recrystallization from water

| Volumes | Stirring Time | Temp. | Seeding | Washing | Impurities IC | Yield | Variation |
|---|---|---|---|---|---|---|---|
| 2 V | 66 h | 22° C. | Yes | 1 × 0.25 V $H_2O$ | 0.69% | 83% | |
| 2 V | 4 h | 5° C. | Yes | 1 × 0.25 V $H_2O$ | 2.5% | 80% | |
| 2 V | 5 h | 10° C. | Yes | 1 × 0.17 V $H_2O$ | 2.0% | 71% | |
| 2 V | 5 h | 22° C. | Yes | 1 × 0.17 V $H_2O$ | n.d. | 46% | |
| 2.1 V | 75 h | 22° C. | No | 1 × 0.25 V NaOH | 1.5% | 79% | 1M NaOH |
| 2.1 V | 75 h | 22° C. | Yes | 1x0.25 V $H_2O$ 1 × 0.25 V EtOH | 0.47% | 62% | |
| 2.1 V | 75 h | 31° C. | Yes | | n.d. | 0% | |
| 2.1 V | 27 h | 21° C. | Yes | 1 × 0.25 V $H_2O$ 1 × 0.25 V EtOH | n.d | 59% | |
| 2.1 V | 75 h | 25° C. | Yes | 1 × 0.25 V $H_2O$ 2 × 0.25 V EtOH | 0.67% | 23% | |
| 2.1 V | 75 h | 15° C. | Yes | 1 × 0.25 V $H_2O$ 2 × 0.25 V EtOH | 0.93% | 66% | |
| 2.1 V | 48 h | 21° C. | Yes | 1 × 0.25 V $H_2O$ 2 × 0.25 V EtOH | 0.48% | 59% | |
| 4.2 V | 118 h | 21° C. | Yes | 1 × 0.25 V $H_2O$ 2 × 0.25 V EtOH | 0.35% | 47% | |
| 2.1 V | 74 h | 21° C. | Yes | 1 × 0.25 V $H_2O$ 2 × x0.25 V EtOH | 0.52% | 63% | |

Crystallization temperature: The experimental results summarized in Table 6 indicated that the crystallization temperature had a strong influence on the isolated yield. Furthermore, more impurities were precipitated at lower temperature. A significant improvement regarding impurity profile and yield was reached at 15-21° C.

TABLE 6

Effect of temperature on crystallization

| Crystallization Temperature | Impurities by IC | Yield |
|---|---|---|
| 5° C. | 2.5% | 80% |
| 10° C. | 2.0% | 71% |
| 15° C. | 0.93% | 66% |
| 21° C. | 0.52% | 63% |
| 25° C. | 0.67% | 23% |
| 31° C. | n.a. | 0% |

Crystallization time: It has been observed that the crystallization of the product was quite slow. Longer stirring times lead to more yield. Best crystallization time was at least 27 hours since increased impurities levels were observed after longer periods. See Table 7.

TABLE 7

Effect of time on crystallization

| Crystallization Time | Crystallization Temperature | Impurities by IC | Yield |
|---|---|---|---|
| 5 h | 22° C. | n.d. | 47% |
| 27 h | 21° C. | n.d. | 59% |
| 48 h | 21° C. | 0.48% | 59% |
| 74 h | 21° C. | 0.52% | 63% |
| 75 h | 22° C. | 0.47% | 62% |

Washing procedure: It was observed that the material isolated after recrystallization in water tended to clump during the drying process. Washing with ethanol before drying led to an improvement and isolation of a homogeneous, fine crystalline powder.

Drying conditions: Elevated drying temperature of 40° C. had a significant effect on drying times without impacting the impurity profile of the isolated product. Therefore, drying at 40° C. was selected. See Table 8.

TABLE 8

Effect of drying conditions

| Temperature | Pressure | Drying Time | Impurities IC | KF |
|---|---|---|---|---|
| 25° C. | 0.01 mbar | 88 | 0.53% | 7.8% |
| 40° C. | 0.01 mbar | 64 | 0.56% | 4.3% |
| 25° C. | 1 mbar | 88 | 0.47% | 11.3% |
| 40° C. | 1 mbar | 64 | 0.52% | 5.2% |

Example 2

$Na_{12}IP_6$ Recrystallization: Centrifugation

Based on the experience of Example 1, a process for recrystallizing $Na_{12}IP_6$ was devised comprising the recrystallization of the product from water and involving a centrifugation step. Ethanol was used to rinse the product before the drying step. The recrystallization was performed in a 1000 L reactor, while a centrifuge was used for isolation. The product was then dried on a tray dryer.

Manufacture process: The original phytate material was obtained from rice (*Oryza sativa*) hulls. A 400 L reactor was flushed with nitrogen and filled with 61.0 kg EP/USP water. A 200 L pressure filter was charged with 20.0 kg CELITE© 545, and the water was emptied from the 400 L reactor into a 1000 L reactor via the pressure filter with BECOPAD© $P_{170}$ depth filter medium until the CELITE© in the pressure filter began to get dry on the surface. The 400 L reactor was charged with a total of 181.8 kg water and 96.6 kg of the $Na_{12}IP_6$ starting material at 15.5-21.4° C. while stirring at 96 rpm. The white suspension was then heated over one hour until 50° C. have been reached and a light-yellow solution was obtained.

The warm solution was filtered over the heated (45° C.) pressure filter into the pre-heated 1000 L reactor. The filter residue was washed with 12.5 kg of pre-heated water. Afterwards, the solution was cooled down within 1 h 50 min from 48.5° C. to 20° C. 97 g of previously recrystallized $Na_{12}IP_6$ batch were added as seeding crystals, and the mixture was stirred during 62 h 15 min between 20° C. and 18.5° C. to form a white suspension. Alternatively, a non-seeded solution may be stirred for a longer time (e.g., around 75 h) to obtain similar results. See Table 5.

In a next step, the suspension was centrifuged washed one time with 24.5 kg water and two times with a total of 38.2 L ethanol. After unloading of the centrifuge 75.0 kg of wet material have been obtained. The product was then transferred to a tray dryer where it was dried for 14 h 10 min at 19.5-32° C. and 200-20 mbar (condensation phase) and later for 148 h 20 min at 32-36° C. and 2 mbar (final drying phase).

A loss on drying as in-process control was performed and showed a result of 5.39% (set value: <=10.0%). The tray dryer oven was unloaded into a 120 L high-density polyethylene (HDPE) drum with a double low-density polyethylene (LDPE) in-liner. The product was homogenized on a gym wheel mixer for 20 min at a speed level of 3.

47.4 kg of recrystallized $Na_{12}IP_6$ were obtained, representing a yield of 49.2%. QC samples we retained and also material to be used as seeding crystals for future batches.

Example 3

$Na_{12}IP_6$ Recrystallization: Filtration

An alternative to the Example 2 process for recrystallizing $Na_{12}IP_6$ was devised comprising a filtration step instead of a centrifugation step.

Manufacture process: A 400 L reactor was flushed with nitrogen and filled with 60 kg EP/USP water. A 200 L pressure filter was charged with 20 kg of CELITE© 545, and the water was emptied from the 400 L reactor in a 630 L reactor via the pressure filter. The 400 L reactor was charged with a total of 186.5 kg water and 100 kg of $Na_{12}IP_6$ starting material at 18.8-20.6° C. while stirring at 100 rpm. The white suspension was then heated over two hours until a temperature of 48.2° C. was reached and a light-yellow clear solution was obtained. The warm solution was filtered over the heated (50° C.) pressure filter into the heated 630 L reactor.

The filtered residue was washed with 13.5 kg of preheated water. Then, the solution was cooled down within 2 h 40 min from 46.8° C. to 20.2° C. 100 g of previously recrystallized $Na_{12}IP_6$ were added as seeding crystals. The mixture was stirred for approximately 60 h between 20.0° C. and 19.1° C. until a white suspension was formed. Alternatively, a non-seeded solution may be stirred for a longer time (e.g., around 75 h) to obtain similar results. See Table 5.

Afterwards, the suspension was filtered over a 200 L agitated filter dryer and was washed once with 25 kg of water. The suspension was then washed twice with 19.7 kg and 19.6 kg of an ethanol solution. The filter dryer was heated, and vacuum was applied at 3 mbar. The drying process was maintained at a temperature below 36° C. until a loss on drying <10% was reached or approximately 10 days.

The product was then unloaded and filled in one 120 L HDPE drum with a double LDPE in-liner.

51.6 kg of recrystallized $Na_{12}IP_6$ were obtained, representing a yield of 51.6% w/w over the starting material.

Example 4

$K_{12}IP_6$ Recrystallization: Filtration $K_{12}IP_6$ is used as starting material for recrystallization as an intermediate step in the production of $K_6IP_6$. A first reactor is flushed with nitrogen and filled with water. A pressure filter is charged, e.g., with CELITE© 545, and the water is emptied from the first reactor into a second reactor via the pressure filter. The first reactor is charged with water and 50 kg of $K_{12}IP_6$ starting material at 15-25° C. while stirring at 100 rpm. The suspension is then heated over two hours until a temperature of approx. 40-50° C. is reached and a clear solution is obtained. The warm solution is filtered over the heated (e.g., at 50° C.) pressure filter into the heated second reactor.

The filter residue is washed with pre-heated water. Then, the solution is cooled down within 2-3 h from 40-50° C. to 15-25° C. A seed amount of previously recrystallized $K_{12}IP_6$ is added as seeding crystals. The mixture is stirred for approximately 50-75 h at approximately 20.0° C. until a suspension was formed.

Afterwards, the suspension is filtered over an agitated filter dryer and is washed once with water. The suspension is then washed twice with a 1:1 water:ethanol solution. The filter dryer is heated, and vacuum is applied at 3 mbar. The drying process is maintained at a temperature below 40° C. until a loss on drying <10% is reached. The product is then unloaded and filled in a HDPE drum with a double LDPE in-liner.

24.5 kg of recrystallized $K_{12}IP_6$ were obtained, representing a yield of 49.0% w/w over the starting material.

In some aspects of this method, the suspension can be purified by centrifugation instead of filtration, as described in Example 2 for the recrystallization of $Na_{12}IP_6$.

Example 5

Preparation of $Na_6IP_6$ from non-recrystallized $Na_2IP_6$

Process 1

The manufacture of $Na_6IP_6$ using non-recrystallized $Na_{12}IP_6$ as starting material comprised the following steps (Process 1):

1. 3.36 L (4.8 volumes) of purified water were charged to a reactor with jacket temp 24° C.±3° C. Stirring was started at medium-high speed and 0.7 kg dodecasodium phytate were added lowly over 30 min. The reaction was slightly exothermic; therefore, speed of addition was controlled to keep temperature below 30° C. The mixture was stirred for further 60 minutes to ensure full dissolution was achieved.

2. The solution was filtered and transferred from the reactor to drum(s).

3. 1CV (column volume) of purified water was flowed through an activated AMBERLITE© ion-exchange column. The flowing of the phytate solution commenced immediately.

4. Fraction collection commenced once loading of sample started and pH measured throughout elution and subsequent wash. Fraction size was approx. 1/8 of the CV (approximately 10 L) but new containers were taken at specific pHs even if current fraction was not full.

5. Each container was changed once pH<1.5, again when pH<1.25 and finally when pH<1.0

6. The solution was chased with 1CV purified water and fraction collection restarted in new container until pH >1.0, changed again when pH >1.25 and again >1.5.

7. pH probe was rinsed well in purified water and retaken pH of fractions. 2 ml of appropriate fractions (pH >2) from each container were submitted for UV testing.

8. The previous steps were repeated, 0.7 kg of dodecasodium phytate at a time, until the entire batch had been processed.

9. Three volumes of ethanol were charged to reactor and chilled to 5° C.

10. Distillation was carried at 40° C. temperature. Maximum temperature did not exceed 45° C. until target distillate volume had been removed or maximum distillation time of 8 hours had been reached. Syrup should be colorless to very pale yellow.

11. The reactor was rinsed with water and the previous step was repeated until the entire batch had been processed.

12. Total weight of phytic acid added to the reactor and total volume ethanol used to discharge syrup were calculated and ethanol was added until a total of 10 volumes of ethanol had been charged to the reactor.

13. The reactor jacket was set to 15° C. and the solution was stirred until internal temperature reached 15° C.

14. Jacket temperature was reset to 10° C. and the solution was stirred at 130 RPM. Sodium methoxide was added portion wise at a rate of 2.5% per minute. pH was monitored throughout the addition of each portion. Addition of sodium methoxide was stopped if pH >5.0 at any point. Solution was allowed to equilibrate, and pH measured after 5 minutes. After addition of 85% of the total charge of sodium methoxide, equilibration time was increased to 15 minutes. If temperature increased above 20° C., addition of sodium methoxide was stopped until temperature decreased to 15+2° C.

15. Slurry was chilled to 5° C. with a jacket temperature of 0° C. Once internal temperature reached 5° C., jacket temperature was raised to 5° C. and stirred for 30 minutes. A 10 ml sample was taken, and if pH was between 4.3 and 5.3 the process continued. Otherwise, sodium methoxide was added in 1% increments until pH was within the pH 4.3-5.3 range.

16. Slurry was stirred at 5° C. for further 1.5 hours, then internal temperature was increased to 10° C., maximum jacket temperature was 15° C. 10 volumes of acetone were added. The mixture was stirred for 60 minutes and then jacket temperature was decreased to 0° C. The mixture was stirred until internal temperature reached 5° C. Jacket temperature was raised to 5° C. and mixture was stirred for 30 minutes.

17. Solid was isolated using centrifuge under nitrogen until a dry solid was obtained. Each cake was washed with 2 volumes of acetone.

18. Reactor was charged with 10 volumes of acetone. All portions of cake from previous step charged and slurry was stirred at 15° C. for 1.5 hours.

19. Jacket temperature was set to 0° C. and solution was chilled to 5° C. Once slurry reaches 5° C., jacket temperature was raised to 5° C. and slurry was stirred for 30 minutes.

20. Solid was isolated using centrifuge under nitrogen until a dry solid was obtained. Each cake was washed with 2 volumes acetone with respect to phytic acid weight.

21. Reactor was charged with 10 volumes of acetone. All portions of cake from the previous step were recharged and slurry was stirred at 15° C. for 1.5 hours.

22. Jacket temperature was set to 0° C. Solution was chilled solution to 5° C. Once slurry reached 5° C. jacket temperature was raised to 5° C. and stirred for 30 minutes.

23. Solid was isolated using centrifuge under nitrogen until a dry solid was obtained. Each cake was washed with 2 volumes of acetone with respect to phytic acid weight.

24. All material from previous steps was loaded into vacuum oven and dried without heat and with small nitrogen bleed. Cake was broken up and stirred every 6 hours. Drying continued until result returned or maximum 48 hours drying time reached. Trays were discharged from oven and stored at −20° C. under desiccant.

25. Material was discharged into liners, doubled with desiccant sachets between liners and deposited in curtec drum.

As a result of this process $Na_6IP_6$ salt 73.4% w/w pure containing the following impurities was obtained:
  (i) DL-Inositol 1,2,3,4,6-pentaphosphate—0.38% w/w
  (ii) DL-Inositol 1,2,3,5,6-pentaphosphate—2.3% w/w
  (iii) DL-Inositol 1,2,4,5,6-pentaphosphate—3.6% w/w
  (iv) DL-Inositol 1,3,4,5,6-pentaphosphate—0.99% w/w
  (v) Unspecified and unidentified impurities—7.8% w/w A comparison of the products obtained in Processes 1, 2, and 3 is presented in Table 9, See below.

Example 6

Preparation of $Na_6IP_6$ from non-recrystallized $Na_2IP_6$

Process 2

The manufacture of $Na_6IP_6$ using non-recrystallized $Na_{12}IP_6$ as starting material comprised the following steps in Process 2.

1. A column was flushed with 3 CV of purified water and emptied.
2. Resin equivalent to approximately 75% of column volume was added.
3. Purified water was added to top of the resin bed, center tube was replaced, and the remaining resin was added.
4. Purified water was added to just above top resin bed, the top of the column was screwed on, and attached to the diaphragm pump (in reverse) ensuring it was leak free.
5. At least 5 CV purified water were flowed through the resin in reverse flow (bottom to top).
6. Lines were switched so flow was top to bottom and flow was at least 5 CV.
7. 5 CV of 1M HCl were flowed through the column. If pH at end volume was <0.4 process continued to step 9. If pH was >0.4, process continued to step 8.
8. 1CV of 1M HCl was flowed through column 1. If pH at end volume <0.4 process continued to step 9. If pH >0.4, step 8 was repeated until pH<0.4.
9. 4 CV of 1M purified water were flowed through vessel. pH at end volume was >3.25.
10. 1 CV of 1M purified water was flowed through column 1 at. If pH at end volume was >3.25 process proceeded to step 11. If pH<3.25, step 10 was repeated until pH >3.25.
11. IPC1: Purity by IC of final purified water wash. Target: RRT 0.69 area <0.04 µS*min. Note if RRT 0.69 peak area was >0.04 µS*min, column was washed with 2 CV of purified water and IPC was repeat.
12. If column was to be stored for less than 1 week; column was flushed with 2 CV of either water or 1M HCl every 24 hours alternating daily.
13. If column was to be stored for >1 week the column was flushed with 2 CV 20% NaCl every 7 days. After storage in NaCl the column was flushed with 5 CV of water and the activation procedure (steps 7-9) was carried out ×4 prior a final activation (steps 7-10) prior to use.
14. If the activated column is not used within 4 h, steps 7-10 were repeated.
15. 3.36 L (4.8 volumes) of purified water were charged to a reactor with jacket temp 24±3° C. Stirring started at medium-high speed and 0.7 Kg dodecasodium phytate were added slowly over 30 minutes. The reaction was lightly exothermic, requiring control of the speed of addition to keep temperature below 30° C. Mixture was stirred for further 60 minutes, ensuring full dissolution was achieved.
16. The solution was transferred with filtration from the reactor into drum(s).
17. 1 CV of purified water was flowed through the column. Flowing of phytate solution from step 15 immediately commence through vessel with pump at same setting used in step 7-10. Note: Actual flow rate during sample addition was slightly reduced due to increased viscosity.
18. Fraction collection commenced once loading of sample started and pH was measured throughout elution and subsequent wash. Fraction size was approximately 1/8 of the CV (approximately 10 L) but new containers were taken at specific pH as stated even if current fraction was not full.
19. Container was changed once pH<1.5, again pH<1.25, and when pH <1.0.
20. The solution was chased with 1 CV purified water and fraction collection restarted in new container until pH >1.0, changed again when pH >1.25, and again when pH >1.5.
21. pH probe was rinsed in purified water and pH of fractions was retaken. Samples of the appropriate fractions (pH >2) from each container were submitted for UV testing.
22. Steps 7-10 were repeated to reactivate resin.
23. The appropriate fractions were combined into the reactor with jacket temperature 24+3° C. Stirring was started at medium-high speed. 0.7 Kg dodecasodium phytate were added slowly over 30 min. The reaction was slightly exothermic. Speed of addition was controlled to keep temperature below 30° C. Stirring continue for further 60 minutes, ensuring full dissolution was achieved.
24. Solutions were transferred with filtration from reactor to drum(s).
25. Steps 17-21 were repeated for exchange and collection of pass 2.
26. Steps 14-25 were repeated until the entire batch has been processed.
27. Steps 14-21 were repeated for exchange and collection if a third pass is required, which depended on the amount of starting material to be processed.
28. Appropriate fractions were combined. Weight was measured and a sample was taken for IPC2. IPC2: IC phytic acid content mg/ml, report result.
29. Three volumes of ethanol with respect to expected total phytic acid weight were loaded to the reactor and chilled to 5° C.
30. Based on IPC2 and volume of exchanged solution, an appropriate volume was charged to a reactor whose distillation rate would allow removal of target volume in <8 hours. Distillation took place at temperature 40° C. Maximum temperature did not exceed 45° C. until target distillate volume had been removed or maximum distillation time of 8 hours was reached. A sample was submitted for IPC3. IPC3: water content by KF, <45% w/w and IPC4: IC purity and assay, report result. Temperature was reduced to 0-5° C. while waiting on results. Note: Syrup should be colorless to very pale yellow.
31. If IPC3 passed, the process proceeded to step 32. If IPC3 failed, process was stopped. IC purity was used to determine how to proceed.
32. If required purified water was added to give 45% w/w, calculated by using IPC2 result and distillate weight. 3 volumes of ethanol with respect to total weight phytic acid in the portion were added at 20° C. until fully mixed. The mixture was discharge with filtration into the appropriate reactor with jacket at 5° C. The reactor was rinsed with 2 volumes of ethanol with respect to the phytic acid in the respective distillation portion and transferred with filtration into reactor containing chilled ethanol from step 29.

33. Prior to charging next portion, reactor was rinsed with 20 L of purified water. Rinse was kept as hold pool. 2 further washes with purified water were discarded.

34. Steps 30 and 33 were repeated until all product solution from step 28 had been processed.

35. Total weight of phytic acid added to the reactor and total volume ethanol used to discharge syrup were calculated. Ethanol was added. The amount of ethanol should be 2 volumes, so a total of 10 volumes were charged to the reactor.

36. Reactor jacket temperature was set to 15° C. The solution was stirred until internal temperature reached 15° C.

37. Jacket temperature was reset to 10° C. Solution was stirred at 130 RPM. Sodium methoxide was added portion wise at a rate of 2.5% per minute, e.g., a 25% charge should take 10 minutes to add. Charge was calculated from IPC2.
  (a) $1^{st}$—25% (500 ml, 26%, pH 0.75)
  (b) $2^{nd}$—25% (500 ml, 26%, pH 0.75)
  (c) $3^{rd}$—20% (400 ml, 21%, pH 0.8)
  (d) $4^{th}$—10% (200 mL, 10%, pH 0.9)
  (e) $5^{th}$—5% (200 mL, 10%, pH 1.1, 1.4 after 10 min)
  (f) $6^{th}$—2.5% (70 mL, 4%, pH 2.4, 4.1 after 10 min)
  (g) $7^{th}$—2.5% (N/A)
  (h) $8^{th}$—1% (20 mL, 1%, pH 4.3)
  (i) $9^{th}$—1% (N/A)
  (j) $10^{th}$—1% (10 mL, 0.5%, pH 4.3, 4.5 after 15 min)

pH was monitored throughout addition of portion. Addition was stopped if pH >5.0 at any point. Mixture was allowed to equilibrate, and pH retaken after 5 minutes. After addition of 85% of the total charge, equilibration time was set to 15 minutes. Sodium methoxide continued to be added in smaller portions until within pH 4.3-5.3 range. At that point addition of sodium methoxide (~97% of calculated amount of sodium methoxide) was terminated, and volume charged was recorded, and the process continued to step 38. If pH was below this range, sodium methoxide continued to be added in 1% portions with continued monitoring of pH until pH within range, target pH 4.8. The amount of sodium methoxide may be less that the amount calculated but should not be exceeded. Note: if temperature increased above 20° C., addition of sodium methoxide was paused until temperature decreased to 15+2° C.

38. Slurry was chilled to 5° C. with a jacket temperature of 0° C. Once internal temperature reached 5° C. jacket temperature was raised to 5° C. Stirring proceeded for 30 minutes. A sample was taken for TPC5. IPC5: test pH range 4.3-5.3 (target 4.8). If IPC5 passed, the process proceeded to step 39. If IPC5 failed, 1% portions of sodium methoxide were added, equilibrated for 30 minutes, and pH tested until pH remained within the pH 4.3-5.3 range. Addition stopped immediately if pH >4.8, in which case it was allowed to equilibrate, and pH retaken after 15 minutes. If pH within pH 4.3-5.3 range, addition of sodium methoxide was terminated, volume charged was recorded, and the process continued to step 39.

39. Slurry was stirred at 5° C. for further 1.5 hours, then internal temperature was increased to 10° C., with maximum jacket temperature at 15° C. 10 volumes of acetone were added. The mixture was stirred for 60 minutes and then the jacket temperature was decreased to 0° C. Stirring continued until internal temperature reached 5° C. At that point jacket temperature was raised to 5° C. and the mixture stirred for 30 minutes.

40. Solid was isolated using centrifuge under nitrogen until a dry solid was obtained. This was done portion wise with the cake being removed after each portion of solution was processed. Each cake was washed with 2 volumes of acetone with respect to the phytic acid weight from IPC2 prior to discharge.

41. Reactor was charged with 10 volumes of acetone. All portions of cake from step 40 were recharged. The slurry was stirred at 15° C. for 1.5 hours.

42. Jacket temperature was set to 0° C. and solution was chilled to 5° C. Once slurry reached 5° C. jacket temperature was raised to 5° C. and slurry was stirred for 30 minutes.

43. Solid was isolated using centrifuge under nitrogen until a dry solid was obtained. This was done portion wise with the cake being removed after half the solution if processed. Each cake was washed with 2 volumes of acetone with respect to phytic acid weight from IPC2 prior to discharge.

44. Reactor was charged with 10 volumes of acetone. All portions of cake from step 43 were recharged. Slurry was stirred at 15° C. for 1.5 hours.

45. Jacket temperature was set to 0° C. Solution was chilled to 5° C. Once slurry reached 5° C. jacket temperature was raised to 5° C. Slurry was stirred for 30 minutes.

46. Solid was isolated using centrifuge under nitrogen until a dry solid was obtained. Each cake was washed with 2 volumes of acetone with respect to the phytic acid weight from IPC2 prior to discharge.

47. All material from step 46 was charged to a vacuum oven and dried without heat and with small nitrogen bleed. Cake was broken/stirred up every 6 hours. After 24 hours a sample was taken for IPC6. IPC6: KF Stromboli <8% w/w. Drying continued until IPC6 result returned or maximum 48 hour drying time reached. If IPC6 passed, the process proceeded to step 48, if IPC6 failed, drying continued until 48 hours total time was reached and another sample was taken for IPC6. Trays were discharged from the oven and stored at −20° C. under desiccant whilst awaiting IPC6 results. If IPC6 $2^{nd}$ sample passed, the process proceeded to step 49. IPC6 $2^{nd}$ sample should be submitted for IPC7: IC purity report result w/w on an anhydrous basis. If IPC6 $2^{nd}$ sample failed, the process proceeded to step 48. Note: The sample to be analyzed was the same sample that was analyzed as IPC6 as water content was required for reporting result.

48. It was decided whether further drying was feasible or necessary.

49. The same sample that passed IPC6 was used for IPC8 and IPC9 as IPC9 was expressed on an anhydrous and solvent free basis.

50. IPC8: residual solvent by GC, ethanol <20000 ppm, methanol <5000 ppm, acetone <5000 ppm. Material was held at −20° C. under desiccant while waiting on IPC8 result. If IPC8 failed, the process was stopped. If IPC8 passed, the process proceeded to step 51. Note: The sample to be analyzed in IPC8 was the final sample that was analyzed as IPC6.

51. IPC9: Sodium content by ICP-MS, 15.4-19.5 on an anhydrous and solvent free basis. Material was held at −20° C. under desiccant while waiting on result. If IPC9 filed, process stopped. If IPC9 passed, process proceeded to step 52. Note: The sample to be analyzed as IPC9 was the final sample that was analyzed as IPC6 and IPC7.

52. Solid was discharged into liners, doubled with desiccant sachets between liners and in curtec drum.

During the crystallization, all equivalents and volumes were relative to crude hexasodium phytate input.

As a result of this process, $Na_6IP_6$ salt 73.4% w/w pure containing the following impurities was obtained:
(i) DL-Inositol 1,2,3,4,6-pentaphosphate—0.33% w/w
(ii) DL-Inositol 1,2,3,5,6-pentaphosphate—2.6% w/w
(iii) DL-Inositol 1,2,4,5,6-pentaphosphate—4.1% w/w
(iv) DL-Inositol 1,3,4,5,6-pentaphosphate—1.1% w/w
(v) Unspecified and unidentified impurities—8.4% w/w A comparison of the products obtained in Processes 1, 2, and 3 is presented in Table 9, See below.

Example 7

Preparation of $Na_6IP_6$ from recrystallized $Na_2IP_6$

Process 3

The manufacture of $Na_6IP_6$ from recrystallized $Na_{12}IP_6$ comprised the following steps in Process 3. This process was developed to improve the drug substance quality by significantly reducing its impurities content. The process introduces an additional purification step of the starting material, i.e., phytic acid dodecasodium salt hydrate, by recrystallization from a water solution. Further steps conducted with the purified phytic acid dodecasodium salt isolated intermediate up to the isolation of the purified drug substance consists essentially of the same three-step ion-salt exchanges previously described for Process 2. The flow-chart for SNF472 (hexasodium phytate) Process 3 is shown in FIG. 5.

(A) Recrystallized starting material: Dodecasodium salt was recrystallized as described in Examples 2 and 3.

(B) Hexasodium phytate preparation:

1. A column was flushed with 3 CV (column volumes) of purified water and emptied.

Approximately 0.25 CV of purified water were added to the column.

2. Resin equivalent to ~75% of CV was added, and purified water was added required to keep the level of water just above the surface of the resin.

3. Resin and water were added until the column was sufficiently packed. The top of the column was screwed and attached to a diaphragm pump (in reverse).

4. At least 5 CV of purified water were flowed through the resin in reverse flow (bottom to top). Lines were switched so flow was top to bottom and at least 5 CV were flowed through.

5. 5 CV 1M HCl were flowed through the column. If pH at end volume <0.4, process continued to step 7, if pH >0.4 it continued to step 6.

6. 1 CV 1M HCl was flowed through the column at 3250 mL/min 100 mL/min, if pH at end volume <0.4 the process continued to step 7, if >0.4 step 6 was repeated until <0.4.

7. 4 CV of purified water were flowed through column. If pH at end volume >3.25 process continue to step 9. If pH<3.25 process continued to step 8.

8. 1 CV of purified water was flowed through column. If pH at end volume >3.25 proceed continued to step 9.

9. Sample that passed pH check in steps 7/8 was used as IPC1. IPC1: Purity by IC of final purified water wash. Target: RRT 0.69 area <0.04μS*min. Note if RRT 0.69 peak area is >0.04 S*min column was washed with 2 CV of purified water and IPC was repeated.

10. Column was activated by repeating steps 5-8.

11. Reactor was charged with 4.8 volumes purified water (with respect to dodecasodium phytate volume). Reactor jacket temperature was set at 24° C.±3° C. Stirring was started at medium-high speed and 0.7 kg dodecasodium phytate were added slowly over 30 minutes. The reaction was slightly exothermic; therefore, speed of addition was controlled to keep temperature below 30° C. (target temperature was 24° C.). Stirring continued for further 60 minutes, ensuring that full dissolution was achieved.

12. Solution was kept under agitation at between 20-25° C. until column had been confirmed as activated and fit to use. Only then the solution was transferred, with filtration, from reactor into drum(s).

13. 1 CV purified water was flowed through the column. Flowing of the phytate solution from step 12 was initiated immediately through the column with pump at same setting used during activation.

14. Fraction collection commenced once loading of sample started and pH was measured throughout elution and subsequent wash. Fraction size was approximately 1/8 of the CV but new containers were taken at specific pHs as stated even if the current fraction was not full.

15. Containers were changed once pH<1.5, again when pH<1.25 and again when pH<1.0.

16. The solution was chased immediately with 1 CV purified water and fraction collection restarted in new container until pH >1.0, changed again when pH >1.25 and again when pH >1.5.

17. pH probe was rinsed well in purified water and pH of fractions was retaken. Samples from appropriate fractions (pH<2) from each container were submitted for UV testing. Fractions were stored at 2-8° C. until further processing.

18. The resin reactivation steps were repeated.

19. The appropriate fractions for Pass 1 were combined:
pH<1.00: all fractions with pH less than one should be combined.
1.00<pH<1.25: most fractions likely to be combined unless UV analysis indicates very weak concentration.
1.25<pH<1.50 unlikely to be included unless UV indicates a significant amount of product present.

20. The combined fractions from the previous step were transferred into the reactor with jacket temperature at 24° C.±3° C. and stirring at medium-high speed was started. Additional dodecasodium phytate was added slowly over 30 min. The reaction was slightly exothermic, so speed of addition was controlled to keep the temperature below 30° C. The solution was stirred for further 60 minutes, ensuring full dissolution was achieved.

21. Solution was maintained under agitation between 20-25° C. until the column had been confirmed as activated and fit to use. Only then the solution was transferred, with filtration, from the reactor into drum(s).

22. Steps 13-17 were repeated for ionic exchange and collection of pass 2.

23. The appropriate fractions for Pass 2 were combined according to the criteria below:
pH<1.00: all fraction pH less than one should be combined.
1.00<pH<1.25: may not be combined unless UV analysis indicated a significant amount of product present.
1.25<pH<1.50 should not be included for Pass 2 unless project chemist indicated otherwise.

24. Steps 10 through 23 were repeated until the entire batch was processed.

25. Appropriate Pass 2 fractions from all runs were combined, weight was measured, and a sample was taken for IPC2. IPC2: IC phytic acid content mg/mL. Determine density.

26. 2 volumes of ethanol with respect to expected total phytic acid weight determined from IPC2, solution weight and density, were loaded to reactor and chilled to 5° C.

27. Based on IPC2 appropriate volume was charged to a reactor whose distillation rate would allow removal of target volume in <10 h, maximum 12 h. The amount of water to be removed was calculated using IPC2 value, and volume to be charged based on an expected final syrup water content of 40%.

28. The solution was distilled with aim to keep internal temperature <40° C. Internal temperature must not exceed 45° C., no lower limit. Syrup should be colorless to very pale yellow.

29. Distillation rate was corrected over the first 2 hours if it was not sufficient to remove required amount of water within maximum allowed time.

30. Once target distillate volume had been removed, a sample was taken for IPC3. IPC3 A: water content by KF, <45% w/w. IPC3B: IC purity and assay, report result. If IPC3 A passed, the process proceeded to step 32. If IPC3A failed, distillation process continued as appropriate up to the maximum distillation time of 12 hours, and additional times was used if needed.

31. If maximum distillation time of 12 h was reached before IPC3A passed, a sample for IPC3 was submitted at this time point and the batch was cooled to 5-8° C. If IPC3A passed, the process proceeded to step 32.

32. If required, purified water was added to give 45% w/w. Value was calculated by using IPC2 result, density and weight solution charged, then 3 volumes of ethanol with respect to total weight phytic acid were added in the portion and agitated at 20° C. until fully mixed. The solution was discharged with filtration into the appropriate reactor with jacket at 5° C. The reactor was rinsed with 3 volumes of ethanol with respect to the phytic acid in the respective distillation portion and transferred with filtration into reactor containing chilled ethanol.

33. Prior to charging next portion, reactor was rinsed with 3 volumes (or appropriate volume for reactor size) of purified water and keep rinse as hold pool. Further washes were discarded.

34. Steps 27 and 31 were repeated until all product solution from step 21 had been processed.

35. Total weight of phytic acid added to the reactor was calculated and also the total volume of ethanol used to discharge syrup. Ethanol was added. The amount of ethanol was 10 volumes with respect to the total amount of phytic acid that had been charged to the reactor.

36. Reactor jacket was set to 15° C. and the solution was stirred until internal temperature reached 15° C.

37. Jacket temperature was reset to 10° C., solution was stirred at 130 RPM, and the sodium methoxide was added portion wise at a rate of 2.5% per minute, e.g., a 25% charge should take 10 minutes to add. Charge calculated from IPC2.
 a. $1^{st}$—25% (500 ml, 26%, pH 0.75).
 b. $2^{nd}$—25% (500 ml, 26%, pH 0.75).
 c. $3^{rd}$—20% (400 ml, 21%, pH 0.8).
 d. $4^{th}$—10% (200 ml, 10%, pH 0.9).
 e. $5^{th}$—5% (200 ml, 10%, pH 1.1, 1.4 after 10 min).
 f $6^{th}$—2.5% (70 ml, 4%, pH 2.4, 4.1 after 10 min).
 g. $7^{th}$—2.5% (N/A).
 h. $8^{th}$—1% (20 ml, 1%, pH 4.3).
 i. $9^{th}$—1% (N/A).
 j. $10^{th}$—1% (10 ml, 0.5%, pH 4.3, 4.5 after 15 min).

pH was monitored throughout the addition of portions. Addition was stopped if pH >5.0 at any point.

The amount of sodium methoxide may be less that the amount calculated but should not exceed 105% of theoretical calculated using IPC2.

38. Slurry was chilled to 5° C. with a jacket temperature of 0° C. Once internal temperature reached 5° C. jacket temperature was raised to 5° C. Slurry was stirred for 30 minutes, and a sample representative of the slurry mix taken for IPC4. IPC4: test pH range 4.3-5.3 (target 4.8). If IPC4 passed, the process proceeded to step 39. If it failed, 1% portions of sodium methoxide were added, equilibrated 30 minutes, and pH was tested until it remained within range 4.3-5.3. Addition was immediately stopped if pH >4.8. If pH was within pH range of 4.3-5.3, addition of sodium methoxide was terminated, volume charged was recorded, and a sample was taken for IPC4. IPC4: test pH range 4.3-5.3 (target 4.8). If samples passed, process proceeded to step 39. If it failed, then the failure loop was repeated.

39. Slurry was stirred at 5° C. for further 1.5 hours, and then internal temperature was increased to 10° C. Maximum jacket temperature was 15° C. 10 volumes of acetone were added. The mixture was stirred for 60 minutes, jacket temperature was decreased to 0° C., and stirring continued until internal temperature reached 5° C. Jacket temperature was raised to 5° C. and mixture stirred for 30 minutes.

40. The solid was isolated using filtration under nitrogen (solid is hygroscopic). Reactor was rinsed with 2×3 volumes of acetone with respect to phytic acid weight from IPC2. Rinse was used to wash cake prior to discharge.

41. Reactor was charged with 25 volumes of acetone. All wet cake from step 38 was recharged. The slurry was stirred at 15° C. for 1.5 hours.

42. Jacket temperature was set to 0° C., and the solution was chilled to 5° C. Once slurry reached 5° C., jacket temperature was raised to 5° C. and solution was stirred for 30 minutes.

43. Solid was isolated using filtration under nitrogen (solid is hygroscopic). Reactor was rinsed with 2×3 volumes of acetone with respect to phytic acid weight from IPC2. Rinse was used to wash cake prior to discharge.

44. Reactor was charged with 25 volumes of acetone. All wet cake from step 41 was recharged into the reactor, and the slurry was stirred at 15° C. for 1.5 hours.

45. Jacket temperature was set to 0° C., and slurry was chilled to 5° C. Once slurry reached 5° C. jacket temperature was raised to 5° C. and the slurry was stirred for 30 minutes.

46. Solid was isolated using filtration under nitrogen (solid is hygroscopic). Reactor was rinsed reactor with 2×3 volumes of acetone with respect to phytic acid weight from IPC2. Rinse was used to wash cake prior to discharge.

47. Cake was deposited on filter under nitrogen without heat. Cake was broken up/stirred every 6 hours. After 24 hours a sample was taken for IPC5A: KF Stromboli <8% w/w. Cake continue drying until IPC5A result returned or maximum 48 hours drying time reached. If IPC5A failed, drying continued, taking samples for IPC5A until 48 h total time was reached. If IPC5A passes, IPC5B was carried out: IPC5B: residual solvent by GC, ethanol <20000 ppm, methanol <5000 ppm, acetone <5000 ppm. The drying of the product on the filter continued whilst awaiting results unless max drying time was reached. When both IPC5A and IPC5B passed the process proceeded to step 50. If IPC5A or IPC5B did not pass and maximum drying time was reached, the process continued to step 48.

48. If max drying time was reached and results IPC5A/IPC5B had not been returned or failed, product was discharged from filter and store in double liners at −20° C. under desiccant whilst awaiting results. If both IPC5A and IPC5B passed, the process proceeded to step 50; if not it proceeded to step 49.

49. Assess whether further drying is necessary/advisable.

50. Discharge into liners, doubled with desiccant sachets between liners and in curtec drum.

Solvents used in the process were purified water (USP pharmaceutical), acetone (99%), sodium methoxide (25% w/w in methanol) and ethanol (99.4%).

As a result of this process, $Na_6IP_6$ salt 82.1% w/w pure containing the following impurities was obtained:
 (i) DL-Inositol 1,2,3,4,6-pentaphosphate—0.14% w/w
 (ii) DL-Inositol 1,2,3,5,6-pentaphosphate—0.26% w/w
 (iii) DL-Inositol 1,2,4,5,6-pentaphosphate—0.74% w/w
 (iv) DL-Inositol 1,3,4,5,6-pentaphosphate—0.17% w/w
 (v) Unspecified and unidentified impurities—1.3% w/w A comparison of the product obtained in Processes 1, 2, and 3 is presented in Table 9, See below.

Example 8

Preparation of $K_6IP_6$ from recrystallized $K_{12}IP_6$

The hexapotassium salt of $IP_6$ ($K_6IP_6$) is prepared using the process disclosed in Example 7 but using $K_{12}IP_6$ prepared according to the process described in Example 4 or $Na_{12}IP_6$ prepared according to the process described in Examples 2 or 3. The method also uses a potassium alkoxide, e.g., potassium methoxide, as a replacement for the sodium alkoxide used in Example 7.

Example 9

Preparation of $Na_6IP_6$ from recrystallized $Na_{12}IP_6$ using an ion exchange batch process Batch process The manufacture of $Na_6IP_6$ from recrystallized $Na_{12}IP_6$ using an ion exchange batch process comprised the following steps:

1. Charge 5.72 eq of an ion exchange AMBERLITE® FPCC14 Na resin (Rohm and Haas Co., Philadelphia,

TABLE 9

Comparison of Processes 1, 2 and 3

| Test | | Parameter | Process 1 | Process 2 | Process 3 |
|---|---|---|---|---|---|
| Appearance | | White or off-White Solid | White Solid | White Solid | White Solid |
| Identification | $^{31}$P-NMR | Concordant with structure | Verified | Verified | Verified |
| | $^1$H-NMR | Concordant with structure | Verified | Verified | Verified |
| | IC | Same retention time as reference standard | Verified | Verified | Verified |
| Assay | IC | Phytic acid on anhydrous solvent free basis % w/w | 73.4 | 73.4 | 82.1 |
| Chromatographic purity | IC | DL-Inositol 1,2,3,4,6-pentaphosphate % w/w | 0.38 | 0.33 | 0.14 |
| | | DL-Inositol 1,2,3,5,6-pentaphosphate % w/w | 2.3 | 2.6 | 0.26 |
| | | DL-Inositol 1,2,4,5,6-pentaphosphate % w/w | 3.6 | 4.1 | 0.74 |
| | | DL-Inositol 1,3,4,5,6-pentaphosphate % w/w | 0.99 | 1.1 | 0.17 |
| | | Any unspecified and unidentified impurity % w/w | | | |
| | | RT 2.5 | | 0.05 | 0.02 |
| | | RT 23.9 | | 0.02 | 0.02 |
| | | RT 25.1 | | 0.02 | 0.02 |
| | | RT 27.6 | 0.02 | | 0.02 |
| | | RT 31.0 | | 0.03 | 0.02 |
| | | RT 33.0 | | | 0.02 |
| | | RT 35.5 | 0.02 | | |
| | | RT 59.8 | | | |
| | | RT 61.0 | | | |
| | | RT 61.7 | 0.07 | | |
| | | RT 63.1 | 0.04 | | |
| | | RT 65.3 | | | |
| | | RT 66.3 | 0.07 | | |
| | | RT 68.6 | | | |
| | | Total impurities % w/w | 7.8 | 8.4 | 1.3 |
| Phosphate Content | IC | Report result (% w/w on the anhydrous basis) | 0.07 | 0.04 | 0.04 |
| Water content | KF titration (Stromboli oven) | Water % w/w | 6.5 | 8.5 | 8.1 |
| Residual solvents | GC | Methanol % w/w | 0.41 | 0.46 | 0.35 |
| | | Ethanol % w/w | 1.36 | 1.71 | 1.29 |
| | | Acetone % w/w | 0.04 | 0.03 | 0.01 |
| Sodium content | ICP-AES | Sodium % w/w anhydrous solvent free basis | 16.8 | 16.3 | 16.6 |

PA, US) to a clean, dry filter and wash with 1M hydrochloric acid (3.7 vols).
2. IPC 1: pH check by pH paper. Target: pH 1-2. Note: If pH >2 then wash the resin with 1M hydrochloric acid (3.7 vols).
3. Wash resin with 1M hydrochloric acid (3×3.7 vols).
4. Wash resin with purified water (7×3.7 vols).
5. IPC 2: pH check by pH meter of final purified water wash. Target: pH >3.5. Note: If pH<3.5 then wash the resin with purified water (2×3.7 vols).
6. IPC 3: Purity by IC of final purified water wash. Target: RRT 0.69 peak area <0.04 μS*min. Note: If RRT 0.69 peak area is >0.04 μS*min wash the resin with purified water (2×3.7 vols).
7. Store the resin in double liner into a drum until next use.
8. Charge purified water (7.0 vols) to a clean, dry mobile reactor at 25° C.
9. Charge phytic acid dodecasodium salt (1.0 eq) slowly to the mobile reactor at 27+3° C. maintaining the temperature below 35° C. and stir for 1+0.5 hour until dissolution occurs. Note: Solution is pH 11/12. Exotherm of 5° C. is typically observed. If dissolution does not occur, increase temperature to 30+3° C. to help aid dissolution.
10. Charge phytic acid dodecasodium salt solution in water via a polishing filter to a clean, dry reactor at 27+3° C.
11. Check that no particulates are present.
12. Charge the washed resin (5.72 eq) to the reaction mixture at 27 3° C. with gentle stirring (~100 rpm).
13. Adjust the temperature to 23+2° C. and stir the solution gently (~100 rpm) for a minimum of 12 hours. Note: Stirring at >100 rpm breaks up resin to a fine powder.
14. IPC 4: pH check by pH paper. Target: pH 1-2. Note: If reaction mixture is >pH 2 increase agitation slightly to ensure sufficient agitation of the resin throughout the solution and take further IPC 4 samples every 1-2 hours until a pH of 1-2 is reached.
15. Filter off the resin and wash with purified water (2×2.5 vols) keeping the washes separate.
16. IPC 5: pH check by pH meter of wash. Target: pH1>1.85. Note: If pH<1.85 wash the resin with purified water (2.5 vols).
17. Charge a fresh portion of the ion exchange resin (2.0 eq) to a clean, dry filter and wash with 1M hydrochloric acid (1.3 vols).
18. IPC 6: pH check by pH paper. Target: pH 1-2. Note: If pH >2 then wash the resin with 1M hydrochloric acid (1.3 vols).
19. Wash the resin with 1M hydrochloric acid (3×1.3 vols).
20. Wash the resin with purified water (7×1.3 vols).
21. IPC 7: pH check by pH meter of final purified water wash. Target: pH >3.5. Note: If pH<3.5 then wash the resin with purified water (2×1.3 vols).
22. IPC 8: Purity by IC of final purified water wash. Target: RRT 0.69 peak area <0.04 μS*min. Note: If RRT 0.69 peak area is >0.04 μS*min wash the resin with purified water (2×1.3 vols).
23. Elute the colorless filtrate through the washed resin collecting in ~5L fractions.
24. Elute the washes followed by purified water through the resin in ~2.5L portions and collect the fractions. Note: Elute purified water through the resin until IPC 9 pH rises to >1.85. Typically, ~1.5 vols water is eluted through the resin.
25. IPC 9: pH check by pH meter. Target: pH of last fraction >1.85. Check pH of the fractions and combine those with a pH of <1.85.

Store phytic acid solution at <10° C.

Example 10

Preparation of $Na_6IP_6$ by Using Sodium Ethoxide (Process 3)

The hexasodium salt of $IP_6$ ($Na_6IP_6$) is prepared using the process disclosed in Example 7 (Process 3) but using sodium ethoxide ($CH_3CH_2NaO$) as a replacement for sodium methoxide alkoxide ($CH_3NaO$).

Example 11

Spray Drying of $Na_6IP_6$

Step 1—Aqueous solution: A 14% (w/v) $Na_6IP_6$ solution was prepared by dissolving $Na_6IP_6$ obtained according to the protocol described in Example 7 (Process 3) in water. The solution was divided in three 20 mL batches and one large 100 mL batch.

Step 2—Spray drying: All batches were spray dried using a Buchi B-290 spray dryer (Buchi Labortechnik AG, Flawil, CH) fitted with a Buchi two-fluid spray nozzle. The spray dryer was fitted with a high-performance cyclone for the three 20 mL batches and a standard cyclone for the 100 mL batch. The spray drying conditions used were 3 g/min (liquid fed rate), 2 bar (atomization pressure), 68-122° C. (inlet temp), 50-90° C. (outlet temp). Outlet temperatures of 50, 70 and 90° C. were used for the three 20 mL batches. An outlet temperature of 90° C. was selected for the 100 mL. All four batches were spray dried successfully with yields ranging from 89.3% to 95.8%. See Table 10.

TABLE 10

| Spray Drying | | | | | | |
|---|---|---|---|---|---|---|
| Batch number | Batch size (mL) | Outlet temp (° C.) | Pressure (bar) | Cyclone | Feed rate (g/min) | Yield (%) |
| 1A | 20 | 50 | 2 | HP | 2.94 | 89.5 |
| 1B | 20 | 70 | 2 | HP | 2.94 | 89.3 |
| 1C | 20 | 90 | 2 | HP | 2.94 | 95.8 |
| 2 | 100 | 90 | 2 | Std | 2.93 | 94.5 |

Example 12

Recrystallization of $Na_6IP_6$ Prepared from Unpurified $Na_{12}IP_6$

Process 3

The manufacture of $Na_6IP_6$ using non-recrystallized $Na_{12}IP_6$ instead of recrystallized $Na_{12}IP_6$ as starting material was assayed according to the protocol described in Example 7 (Process 3):
(A) Starting material: Unpurified phytic acid dodecasodium salt (Sigma-Aldrich, Saint Louis, MO, US) was employed as starting material.
(B) Unpurified hexasodium phytate preparation: Unpurified hexasodium phytate was prepared using the Phase A starting material and following steps 1-49 of Example 7 (Process 3).

(C) Purified hexasodium phytate preparation: Purified hexasodium phytate was prepared by recrystallizing the Phase B intermediate product according to the protocols described in either Examples 2 or 3.

Example 13

Preparation of $Na_6IP_6$ from Non-Recrystallized $K_{12}IP_6$

Process 3

The manufacture of $Na_6IP_6$ using non-recrystallized $K_{12}IP_6$ as starting material was assayed according to the protocol described in Example 7 (Process 3):
(A) Starting material: Unpurified phytic acid dodecapotassium salt was employed as starting material.
(B) Unpurified hexasodium phytate preparation: Unpurified hexasodium phytate was prepared using the Phase A starting material and following steps 1-49 of Example 7 (Process 3).
(C) Purified hexasodium phytate preparation: Purified hexasodium phytate was prepared by recrystallizing the Phase B intermediate product according to the protocols described in either Examples 2 or 3.

Example 14

Preparation of $Na_5IP_6$ from non-recrystallized $Na_{10}IP_6$

Process 3

The manufacture of $Na_5IP_6$ using non-recrystallized $Na_{10}IP_6$ as starting material was assayed according to the protocol described in Example 7 (Process 3).
(A) Starting material: Unpurified phytic acid decasodium salt (Sigma-Aldrich, Saint Louis, MO, US) was employed as starting material.
(B) Unpurified pentasodium phytate preparation: Unpurified pentasodium phytate was prepared using the Phase A starting material and following steps 1-49 of Example 7 (Process 3).
(C) Purified pentasodium phytate preparation: Purified pentasodium phytate was prepared by recrystallizing the Phase B intermediate product according to the protocols described in either Examples 2 or 3.

Example 15

Characterization of $Na_6IP_6$ prepared using recrystallized $Na_2IP_6$ as starting material The $Na_6IP_6$ drug substance was fully characterized by a combination of spectroscopic techniques (mono and bidimensional nuclear magnetic resonance $^1$H-NMR, $^{31}$P-NMR, $^{13}$C-NMR ultraviolet-visible spectroscopy, infrared spectroscopy, and mass spectrometry), elemental analysis and chromatographic techniques (ion-exchange chromatography (IC)).

Nuclear magnetic resonance: The structure was confirmed by the nuclear magnetic resonance studies, according to the assignment of the signals shown in Table 11, and the identification was further confirmed by ion-exchange chromatography, according to the phytic acid reference standard retention time. Table 11 lists the chemical shifts, multiplicities and coupling constants obtained from a multi-nuclear and multi-dimensional study of $Na_6IP_6$ (hexasodium phytate). These data unequivocally established the structure of this molecule as that of structure proposed in hexasodium phytate shown in FIG. 2.

TABLE 11

$^{31}$P-NMR, $^1$H-NMR and $^{13}$C-NMR Chemical Shift Data for $Na_6IP_6$ (hexasodium phytate)

| Position of Phosphorus Atom | Phosphorus Chemical Shift [a] | Position of Proton | Proton Chemical Shift [b] | $^3$J-($^1$H-$^1$H) Coupling Constants [c] | Position of Carbon Atom | Carbon Chemical Shift [d] |
|---|---|---|---|---|---|---|
| $P_{1,3}$ | Singlet, 0.2 ppm | $H_{1,3}$ | Multiplet, 4.15-4.30 ppm | 1,3-diaxial ($H_1$-$H_6$) & ($H_3$-$H_4$) = ~10.0 Hz; Gauche ($H_1$-$H_2$) & ($H_3$-$H_2$) = ~2.3 Hz | $C_{1,3}$ | 76 ppm |
| $P_2$ | Singlet, −0.2 ppm | $H_2$ | Multiplet, 4.85-4.95 ppm | Gauche ($H_2$-$H_1$) & ($H_2$-$H_3$) = ~2.4 Hz | $C_2$ | 78 ppm |
| $P_{4,6}$ | Singlet, 0.8 ppm | $H_{4,6}$ | Quartet, 4.40-4.55 ppm | 1,3-diaxial ($H_4$-$H_3$) & ($H_6$-$H_1$) = ~10.1 Hz Similarly, 1,3-diaxial ($H_4$-$H_5$) & ($H_6$-$H_5$) = ~10.0 Hz | $C_{4,6}$ | 79 ppm |
| $P_5$ | Singlet, 1.4 ppm | $H_5$ | Multiplet, 4.15-4.30 ppm | 1,3-diaxial ($H_5$-$H_6$) & ($H_5$-$H_4$) = ~10.2 Hz | $C_5$ | 80 ppm |

Figure 7:
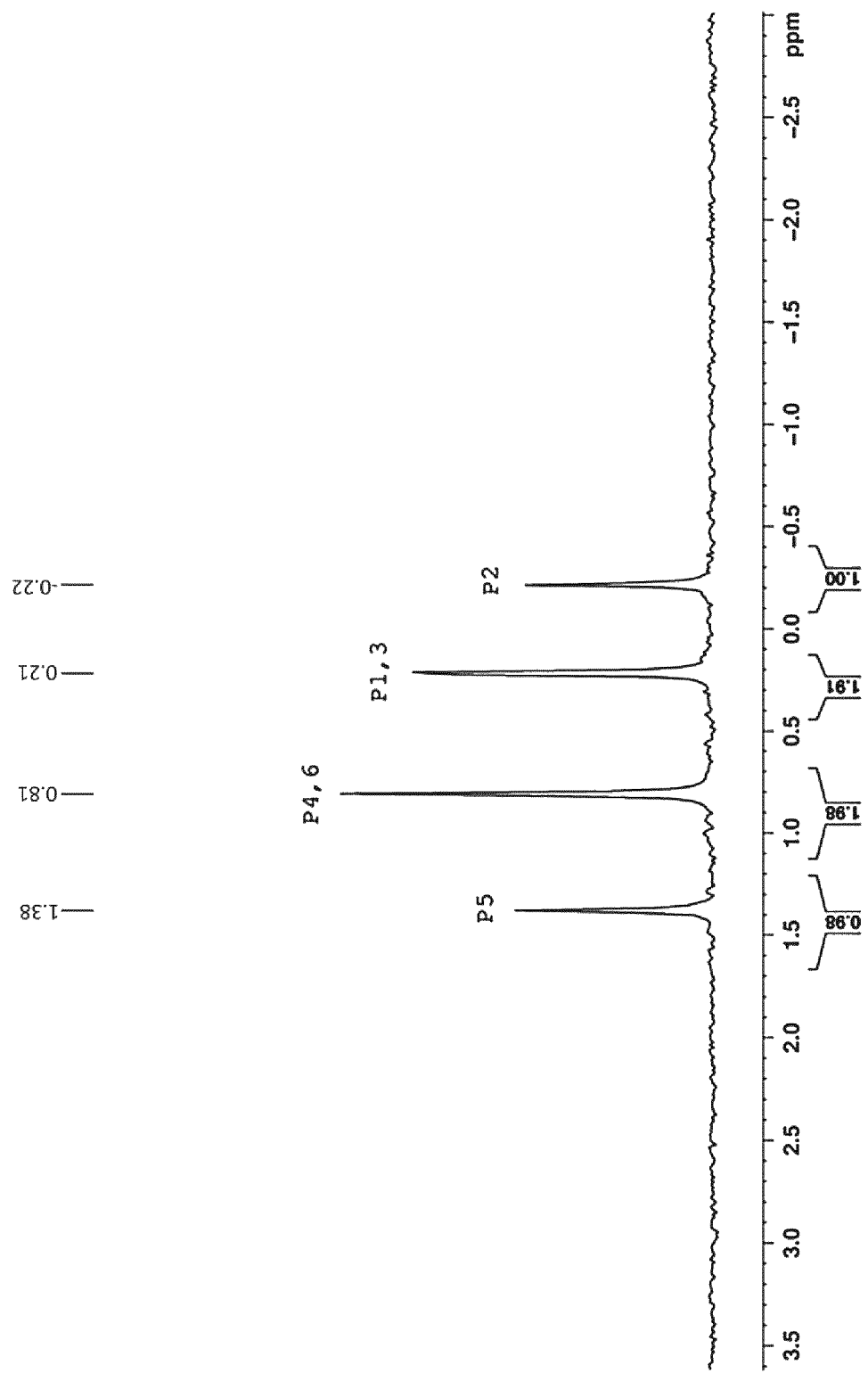
FIG. 7 shows an expanded Proton Decoupled $^{31}P$-NMR Spectrum of $Na_6IP_6$.

[a] Taken from FIG. 7; chemical shifts referenced to 85% (w/w) phosphoric acid. Assignments established from the $^1$H-$^{31}$P-HMBC experiment.

Figure 9:
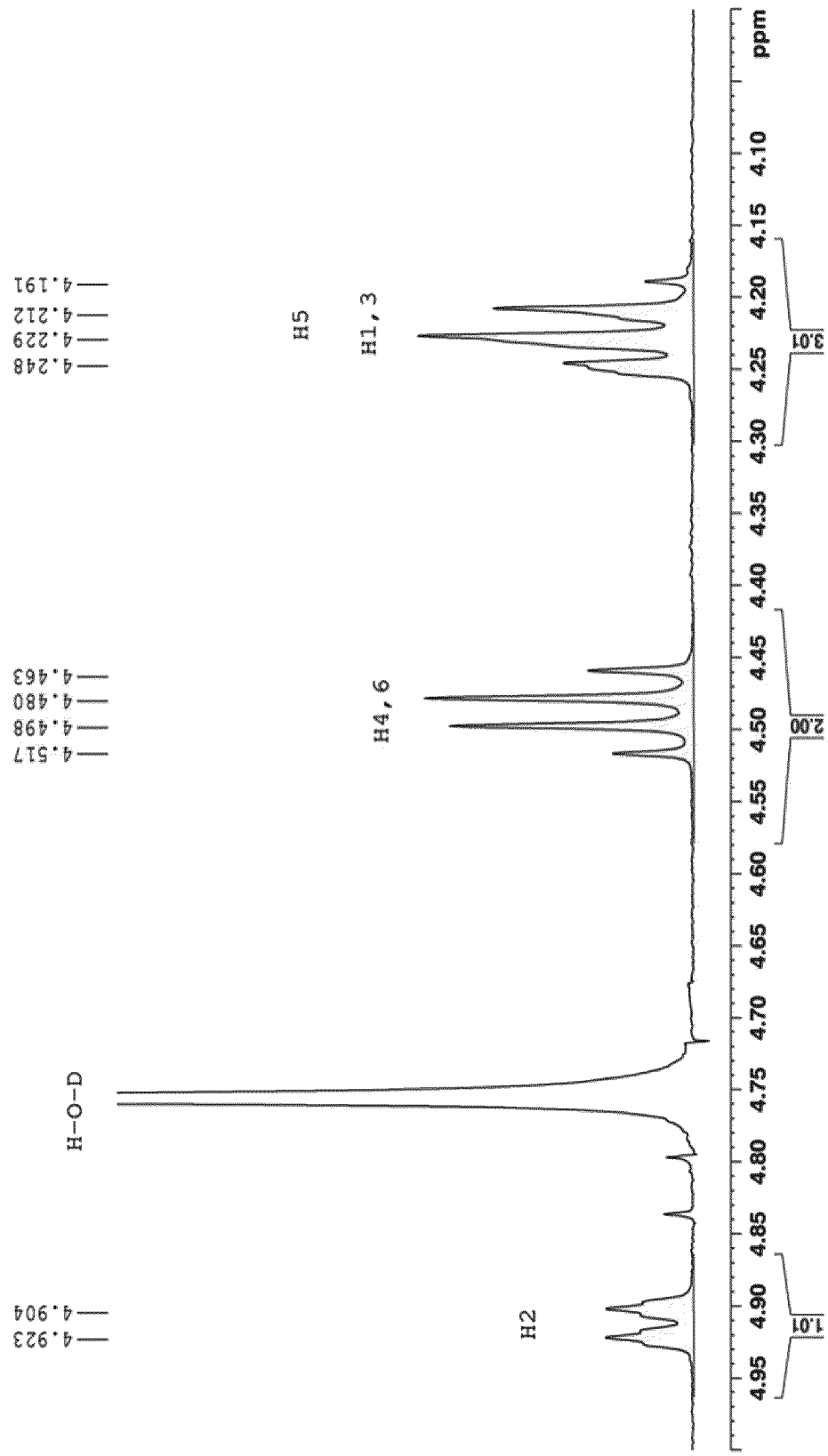
FIG. 9 shows an expanded $^1H$-NMR spectrum of $Na_6IP_6$.

[b] Taken from FIG. 9; chemical shifts referenced to 0.05% (w/w) Trimethylsilyl propionate-$d_4$ (TSP) as internal standard.

Figure 10:
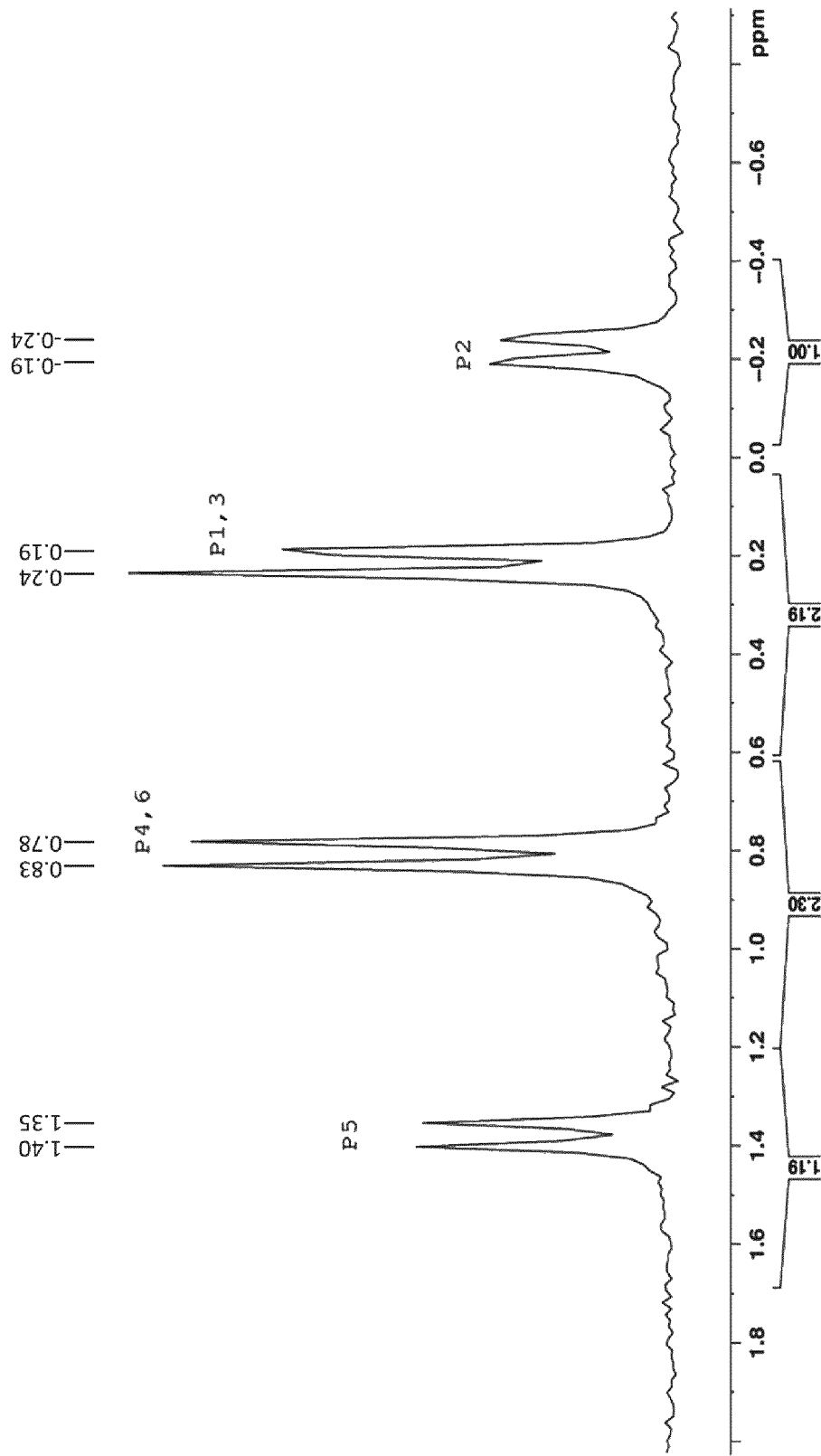
FIG. 10 shows an expanded non-decoupled $^{31}P$-NMR spectrum of $Na_6IP_6$.

[c] Taken from FIG. 9; note that each proton had an additional splitting of 10.0+0.3 Hz due to a $^3$J-($^1$H-$^{31}$P) coupling, which can be clearly seen in the non-decoupled $^{31}$P-NMR spectrum, FIG. 10.

Figure 11:
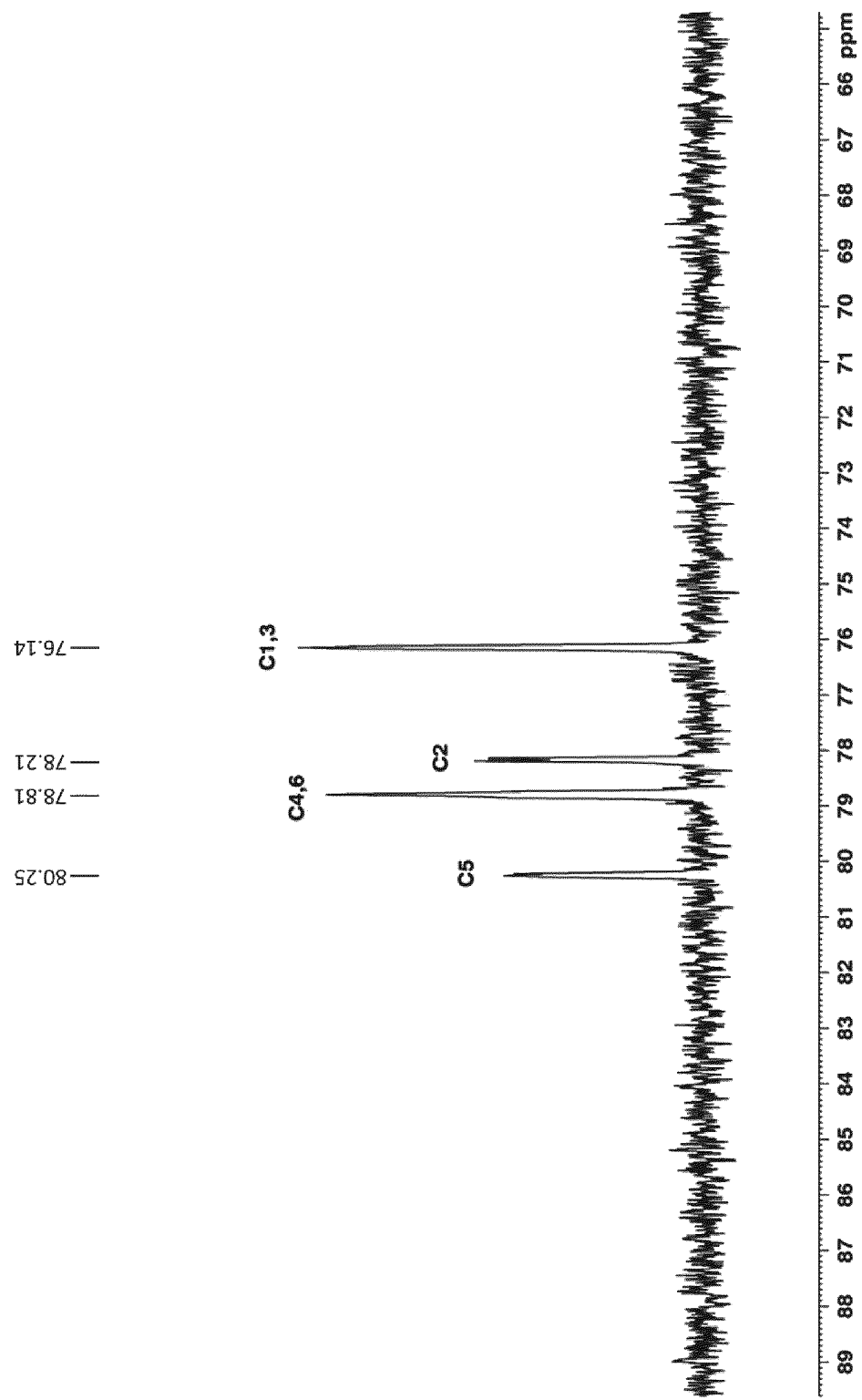
FIG. 11 shows an expanded $^{13}C$ NMR spectrum of $Na_6IP_6$.

[d] Taken from FIG. 11; chemical shifts referenced to 0.05% (w/w) Trimethylsilyl propionate-$d_4$ (TSP) as internal standard. Each $^{13}$C peak was further split by a small (<6 Hz)$^2$J-($^{13}$C-$^{31}$P) coupling which had the effect of "broadening" the peaks; hence, they were quoted to the nearest unit ppm. Chemical shift assignments were established from the $^1$H-$^{13}$C HSQC experiment, FIG. 12.

Figure 8:
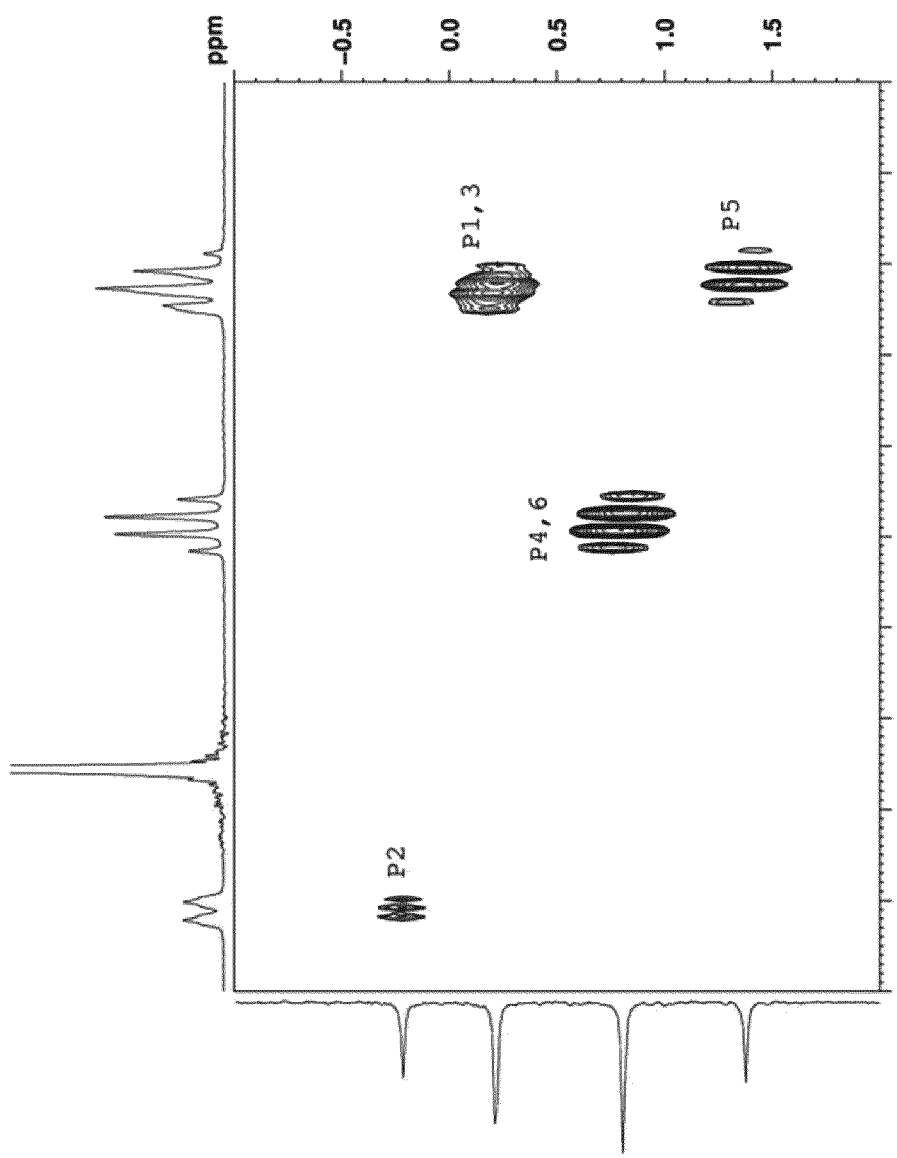
FIG. 8 shows a $^1H$-$^{31}P$ HMBC of $Na_6IP_6$.
Figure 12:
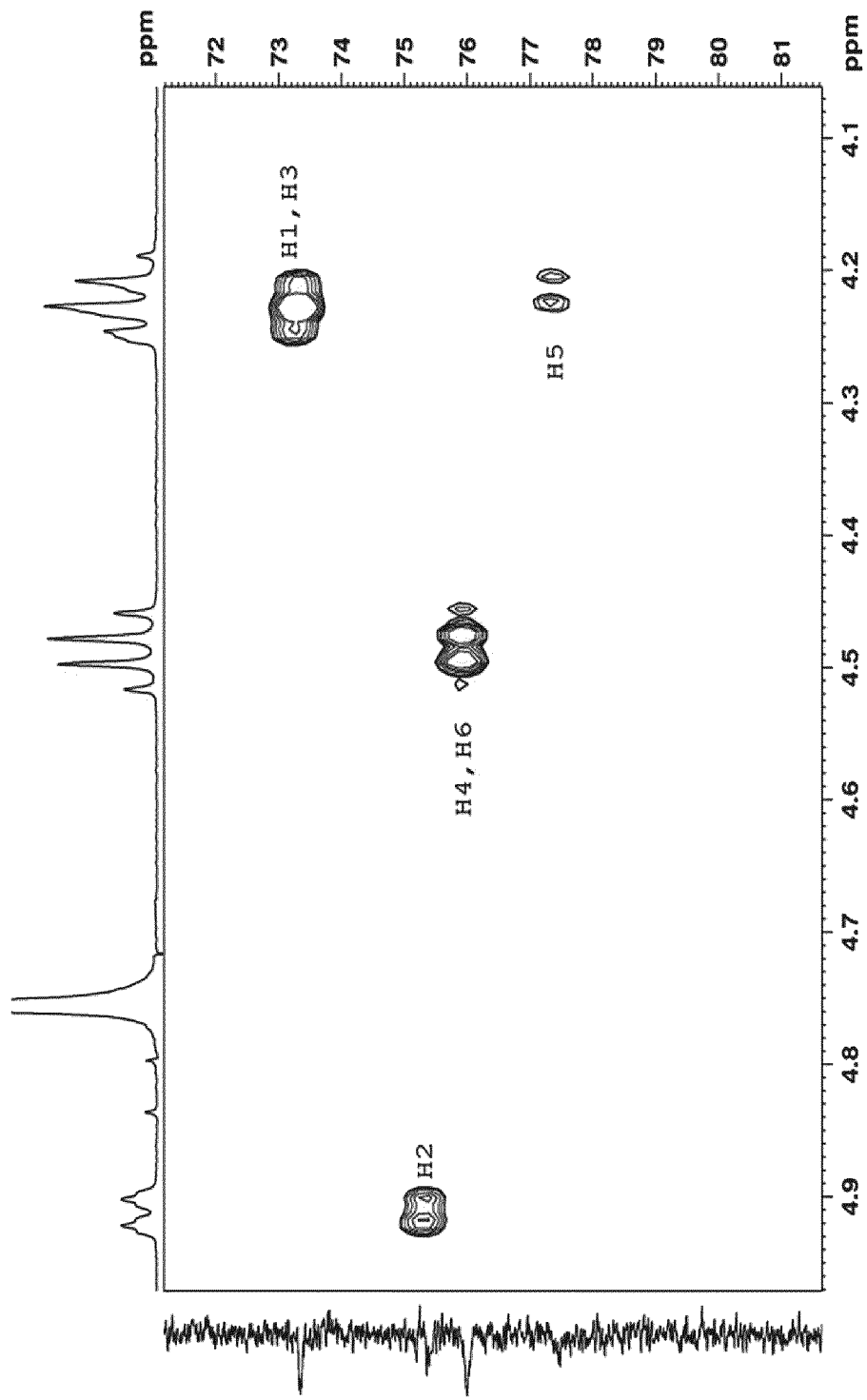
FIG. 12 shows a $^1H$-$^{13}C$ HSQC of $Na_6IP_6$.
Figure 13:
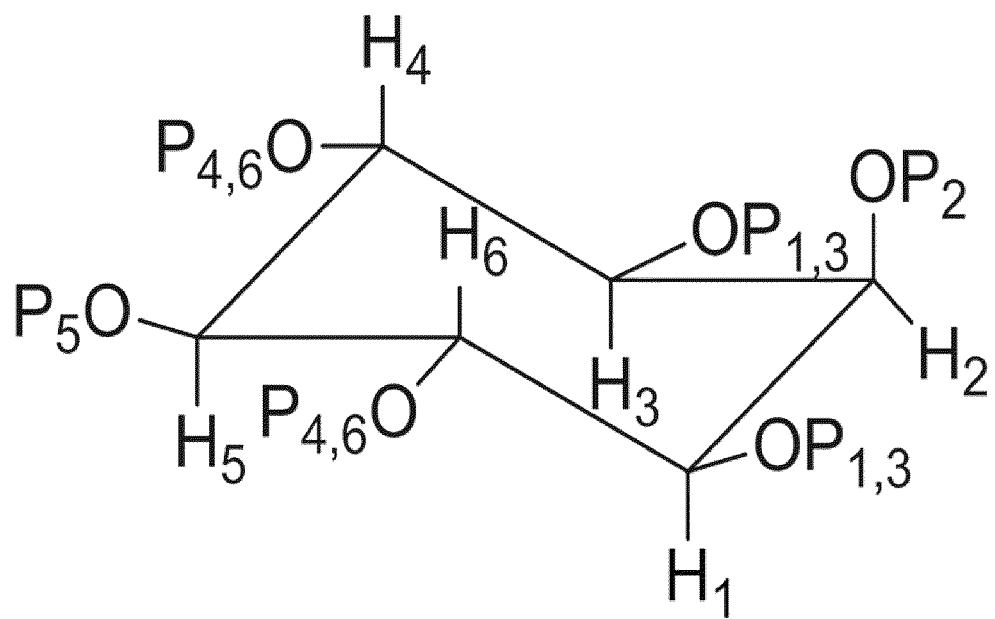
FIG. 13 is a diagram showing the chair conformation of myo-inositol hexaphosphate.

There were only four peaks in the $^{31}$P-NMR spectrum, with an integral ratio of 1:2:2:1 (FIG. 7), even though the molecule has six phosphorus atoms. This was because the molecule has an orthogonal plane of symmetry along the $C_2$-$C_5$ axis. There were only four signals in the $^{13}$C NMR spectrum as well (FIG. 11). Assignments of the $^{31}$P and $^{13}$C peaks could not be made on the basis of their chemical shifts (as the differences between them are so small), and so the assignments in Table 11 were made by 2D-correlation with the nearest proton; specifically, the $^{31}$P assignments came from the $^1$H-$^{31}$P HMBC spectrum (FIG. 8) and the $^{13}$C assignments from the $^1$H-$^{13}$C HSQC spectrum (FIG. 12). The proton assignments were made, unambiguously, by inspection of the $^1$H-NMR spectrum of hexasodium phytate (FIG. 9). Visualizing the dihedral angles (and hence assigning the proton-proton couplings) was made easier by drawing the molecule in the chair conformation, as shown below in FIG. 13.

Figure 14:
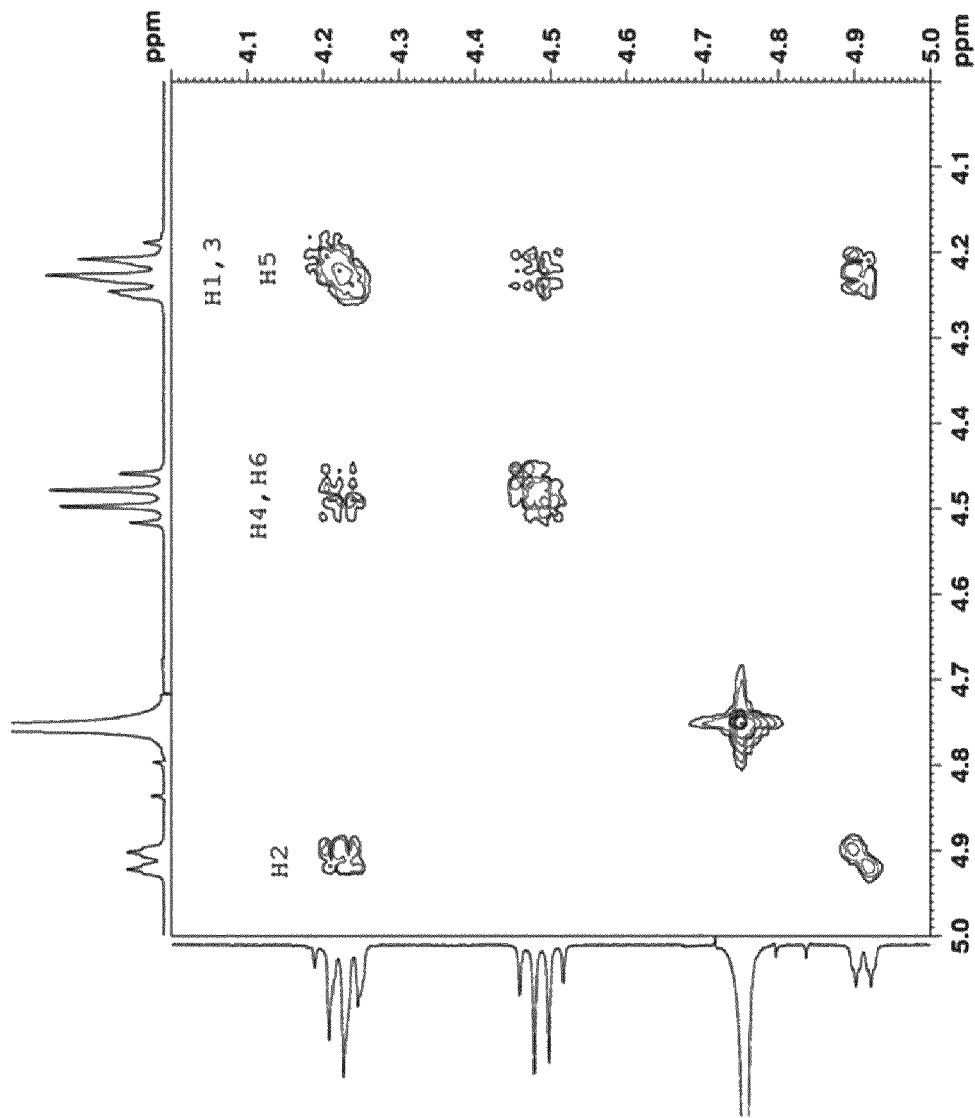
FIG. 14 shows a $^1H$-$^1H$ COSY of $Na_6IP_6$.

Assignments of protons are shown in Table 11. The easiest proton to assign in FIG. 9 was H2, as it was the only one that did not have a 1,3-diaxial coupling; this proton must therefore be the multiplet (doublet of triplets at 4.85-4.95 ppm). The simplicity of the quartet at 4.40-4.55 was unexpected as it should be a doublet of triplets. The 1,3-diaxial couplings of H4 and H6 were virtually identical to their $^3$J-($^1$H-$^{31}$P) coupling, giving rise to a virtually perfect binomial quartet. Finally, even though we could not directly observe H5, we could infer its presence in the 4.15-4.30 ppm region from the integral ratios of: 3: 2: 1. It could also be seen from its cross-peak in the $^1$H-$^1$H COSY (FIG. 14). The large peak at 4.75 ppm in FIG. 9 was the residual solvent peak (H—O-D), and the two small peaks in the region 4.79-4.85 ppm were its distorted spinning side bands.

Figure 2:
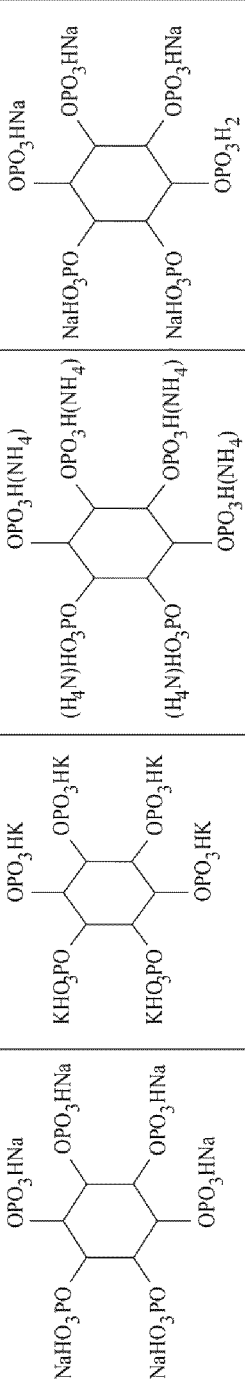
FIG. 2 shows non-limiting examples of the structure and some physicochemical properties of $Na_6IP_6$, $K_6IP_6$, $Na_5IP_6$, and $(NH_4)_6IP_6$.
Figure 15:
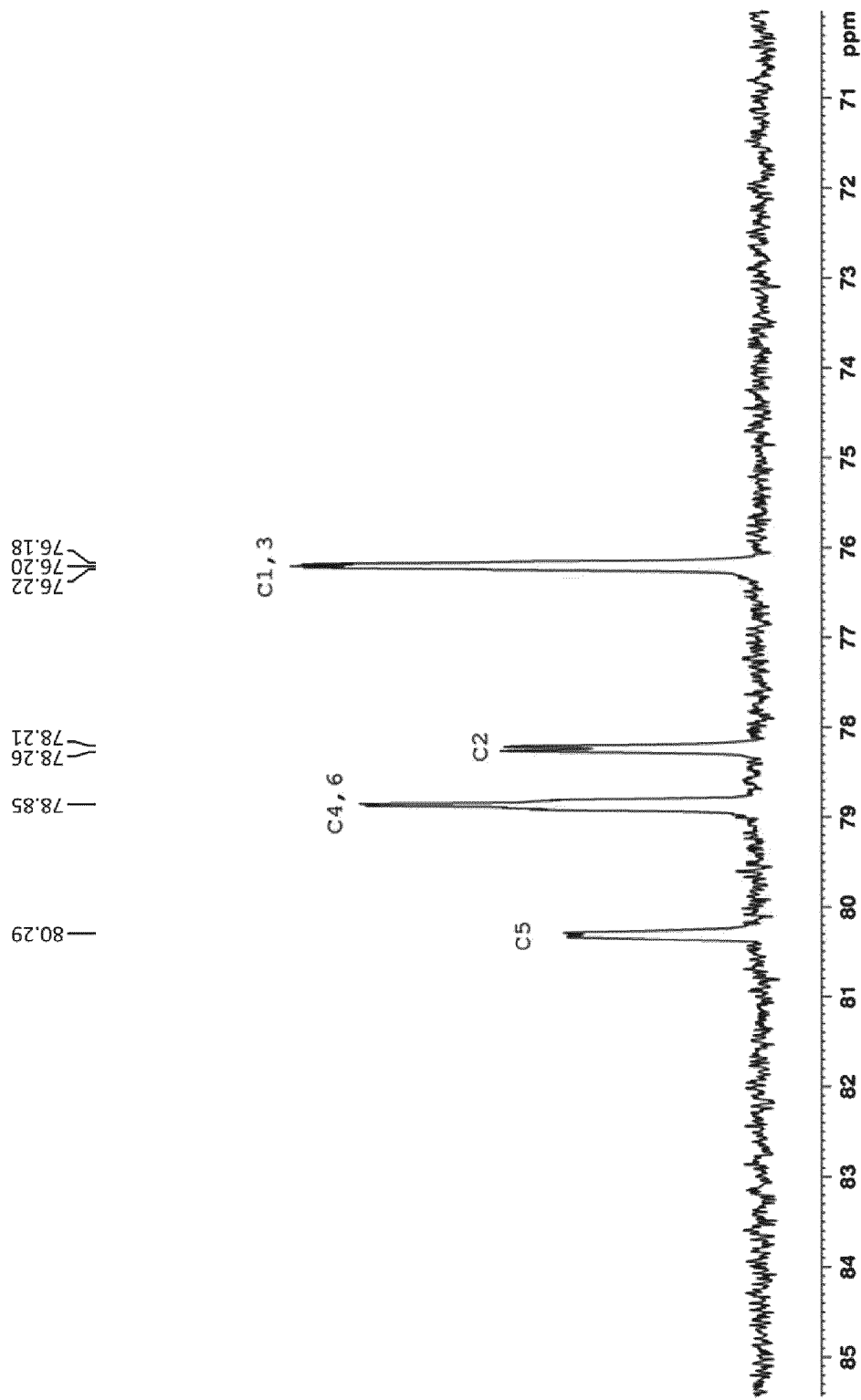
FIG. 15 shows an Expanded DEPT135NMR spectrum of $Na_6IP_6$.

The DEPT 135 spectrum of Na$_6$IP$_6$ is shown in FIG. 15, and confirmed that all the carbon atoms are methines, consistent with the proposed structure in FIG. 2. Finally, the non-decoupled $^{31}$P-NMR spectrum of Na$_6$IP$_6$ (FIG. 10) provided the $^3$J-($^1$H-$^{31}$P) coupling constants that were used to rationalize the assignments of Table 11.

Ultraviolet-Visible spectroscopy: Na$_6$IP$_6$ is a compound which has no characteristic absorption spectra in ultraviolet or visible region typical in the group of inositol phosphates.

Figure 16:
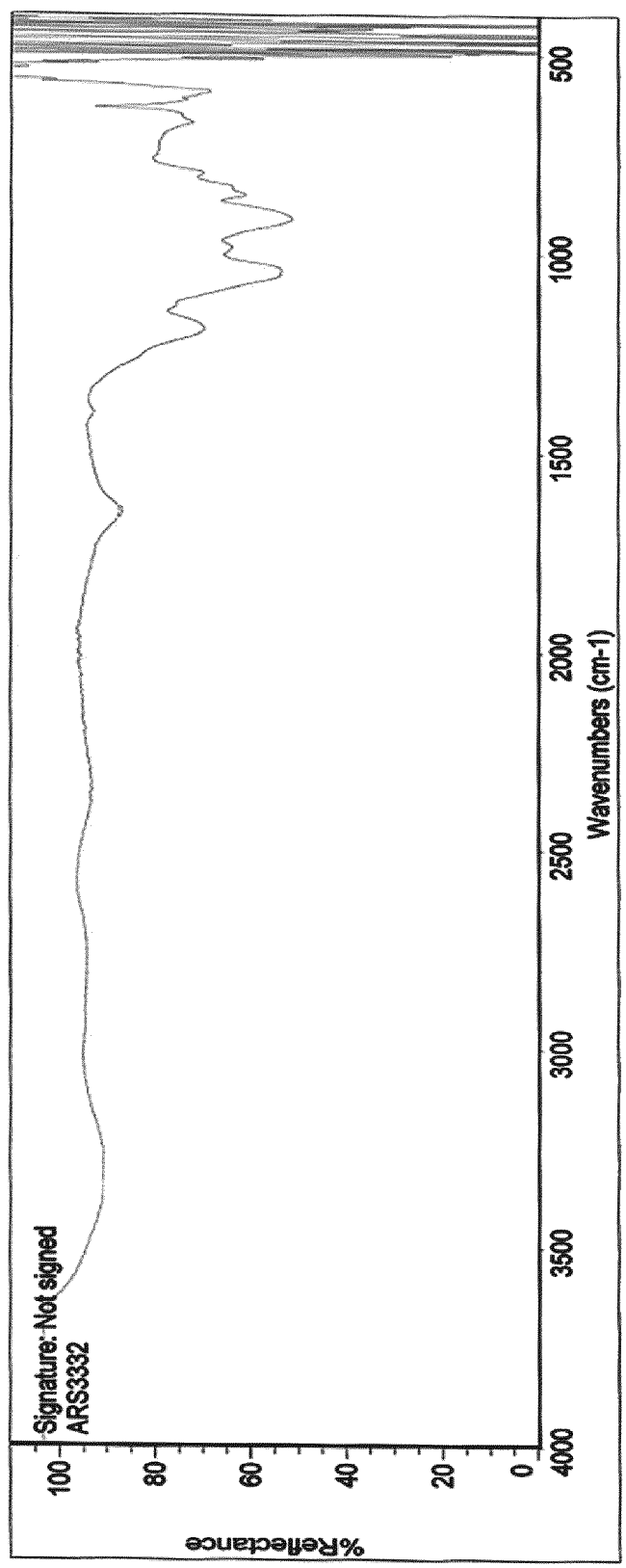
FIG. 16 shows an FT-IR spectrum of $Na_6IP_6$.

FT-Infrared spectroscopy: The FT-IR spectrum of Na$_6$IP$_6$ is shown in FIG. 16. It showed a weak absorption band around 1680 cm$^{-1}$ and a broad absorption band at 3400 cm$^{-1}$. These two bands did not disappear after drying samples. The observations demonstrated the existence of O—H bonds which could be due to crystalline water, metal hydroxide impurities, and unbounded P—O—H bonds. The characteristic IR spectrum was in the region from 1200 to 700 cm$^{-1}$. It showed a broad trailing band at 1106 cm$^{-1}$, triplet bands at 972, 937 and 913 cm$^{-1}$, and other triplet bands at 830, 776, and 746 cm$^{-1}$. Assuming that the broad band at 1106 cm$^{-1}$ represents three convoluted bands, the triplet characteristics implied three sets of C—O bonds which were in accordance with a 5-axial/1-equatorial distribution of phosphate moieties in Na$_6$IP$_6$. See FIG. 12. Based on the relative spectral band strength and the number of symmetric P atoms, the FT-IR bands of 746 and 913 cm$^{-1}$ were assigned to P$_2$. The FT-IR bands of 776 and 937 cm$^{-1}$ were assigned to P$_1$ and P$_3$, and 830 and 972 cm$^{-1}$ to P$_4$, P$_5$ and P$_6$. FT-IR did not distinguish between P$_4$/P$_6$ and P$_5$ indicating less impact of far distance P atoms (P$_2$ to P$_6$ or P$_4$ and P$_1$/P$_3$ to P$_5$) on P—O bond characteristics than on the nuclear magnetic resonance properties of P atoms. The FT-IR spectrum was in accordance with $^{31}$P-NMR spectrum.

Figure 17:
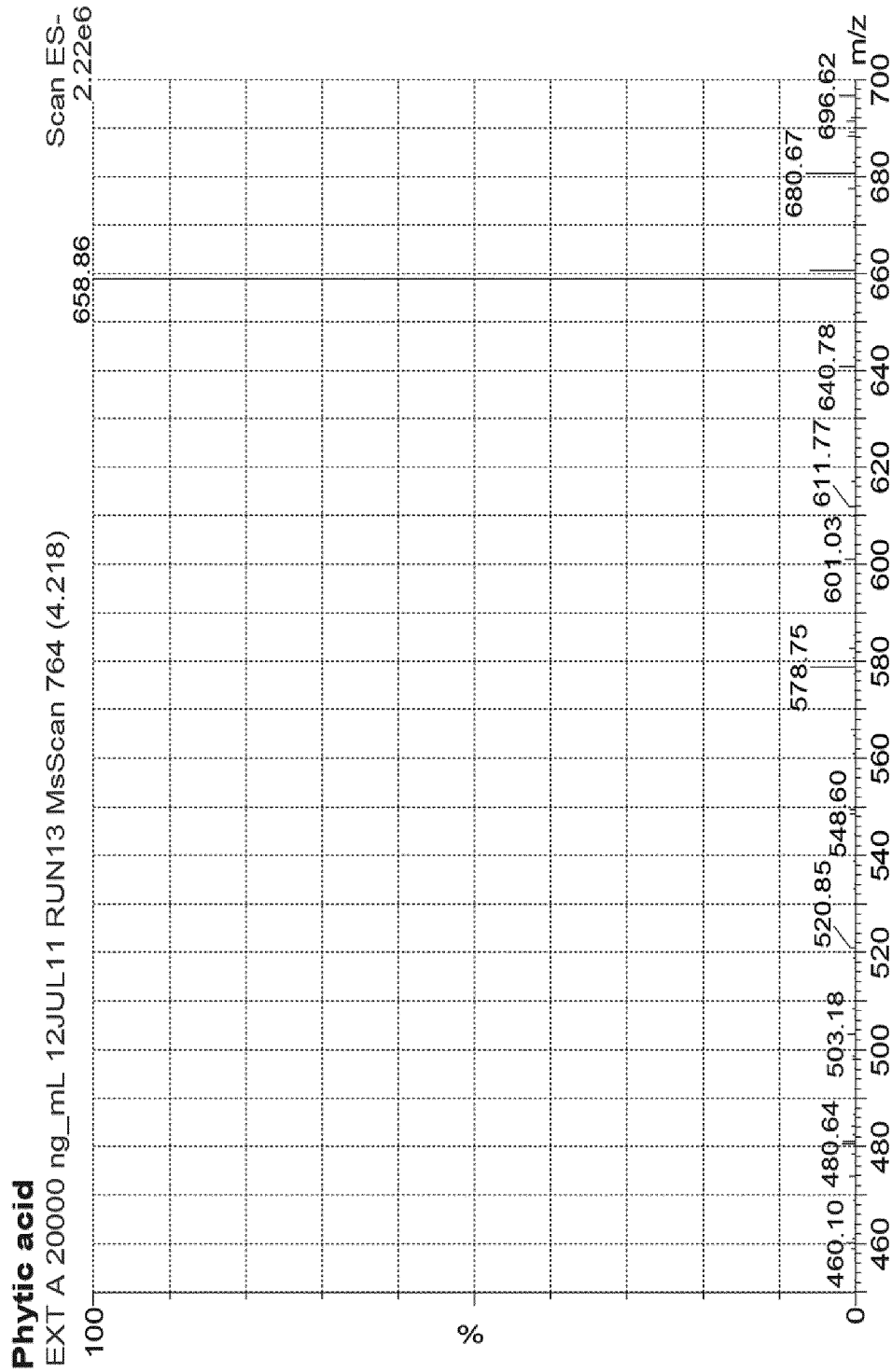
FIG. 17 shows a typical mass spectrum of $Na_6IP_6$.

Mass spectrometry: The molecular mass of Na$_6$IP$_6$ was confirmed by the peak corresponding to the molecular ion of m/z 659 ([M-H]$^-$) by tandem mass spectrometry in the selected ion monitoring (SIM) mode after negative electrospray ionization (ESI). The molecular ion of m/z 659 ([M-H]$^-$) corresponded to phytic acid molecule (m/z=660) that had lost a hydrogen atom during negative electrospray ionization. The compound was analyzed by gradient reversed-phase chromatography using TEAA 50 mM pH 9 and ACN as mobile phase injecting 20 µL into the UPLC©-MS. The mass spectrum of FIG. 17 shows the molecular ion of m/z 659 ([M-H]$^-$) after negative electrospray ionization (ESI). The instrument used was an API4000TM Mass Detector (2000 amu upper mass limit—triple quadrupole) with ESI interface (AB Sciex).

Elemental analysis, Sodium content (% Na) and Phosphorus content (% P): Elemental analysis of Na$_6$IP$_6$ was carried out and the results are included in Table 12. Characterizing the contribution of cations to the elemental composition of Na$_6$IP$_6$ (hexasodium salt) the Sodium content (%) in conjunction with total Phosphorous content (%) allowed to assess the stoichiometric ratio of the salt, which at the same time was an indication of purity. Sodium content found was close to the calculated theoretical value thus confirming that the stoichiometry of Na$_6$IP$_6$ conformed to the hexasodium salt (6 mol sodium per mol phytic acid).

TABLE 12

Elemental analysis of Na$_6$IP$_6$

| Elemental Analysis$^a$ | C[%] | H[%] | N[%] | P[%]$^{a,b}$ | Na[%]$^{a,b}$ |
|---|---|---|---|---|---|
| Calculated | 9.1 | 1.5 | 0.0 | 23.5 | 17.4 |
| Found | 8.3 | 2.4 | <0.3 | 22.3 | 16.2 |

$^a$Minor variation in calculated and found values is attributed to the content of water in the sample.
$^b$Phosphorus and sodium content measured by ICP-OES.

Figure 18:
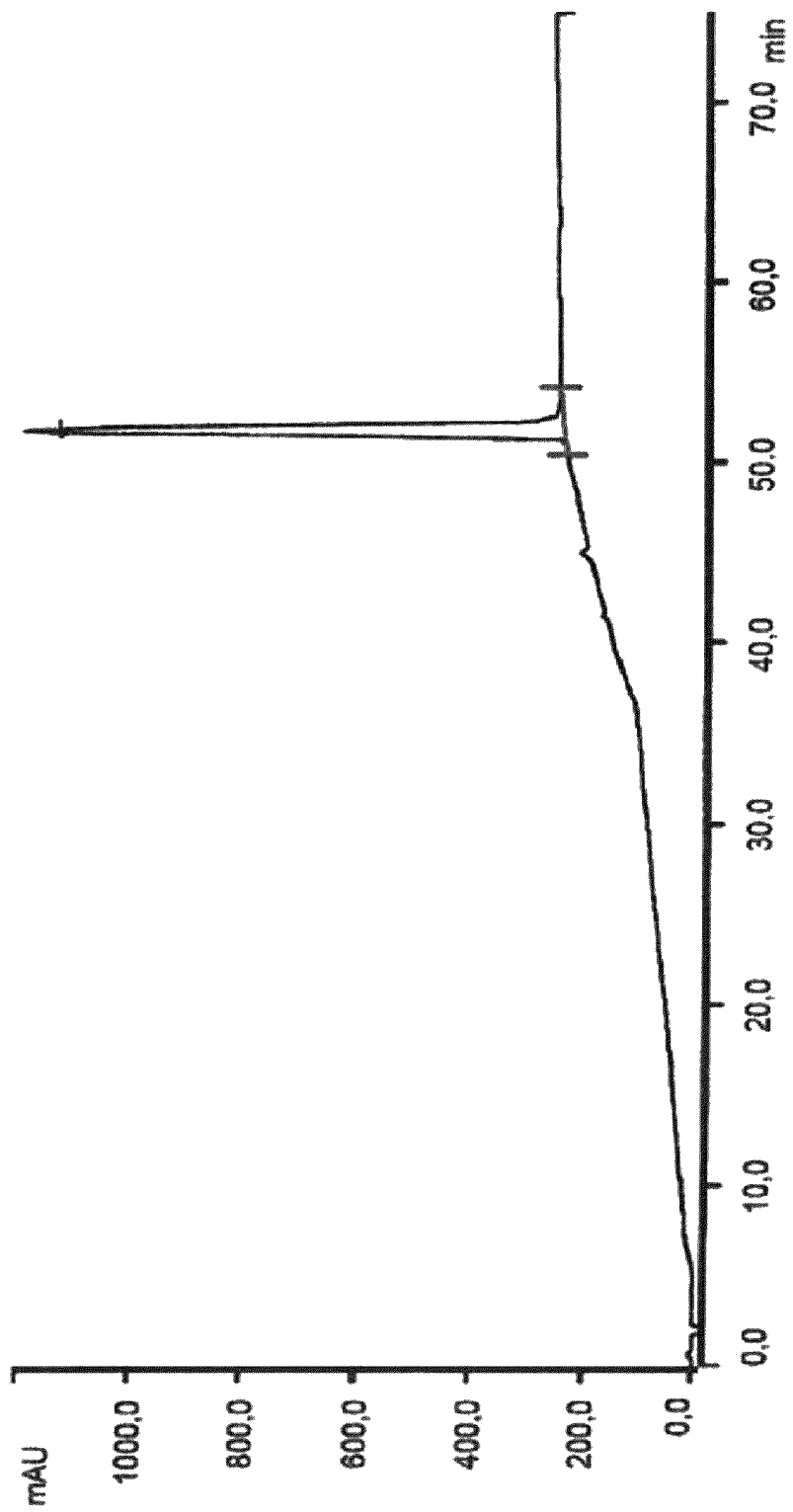
FIG. 18 shows an IC chromatogram of $Na_6IP_6$ prepared according to Process 3.
Figure 19:
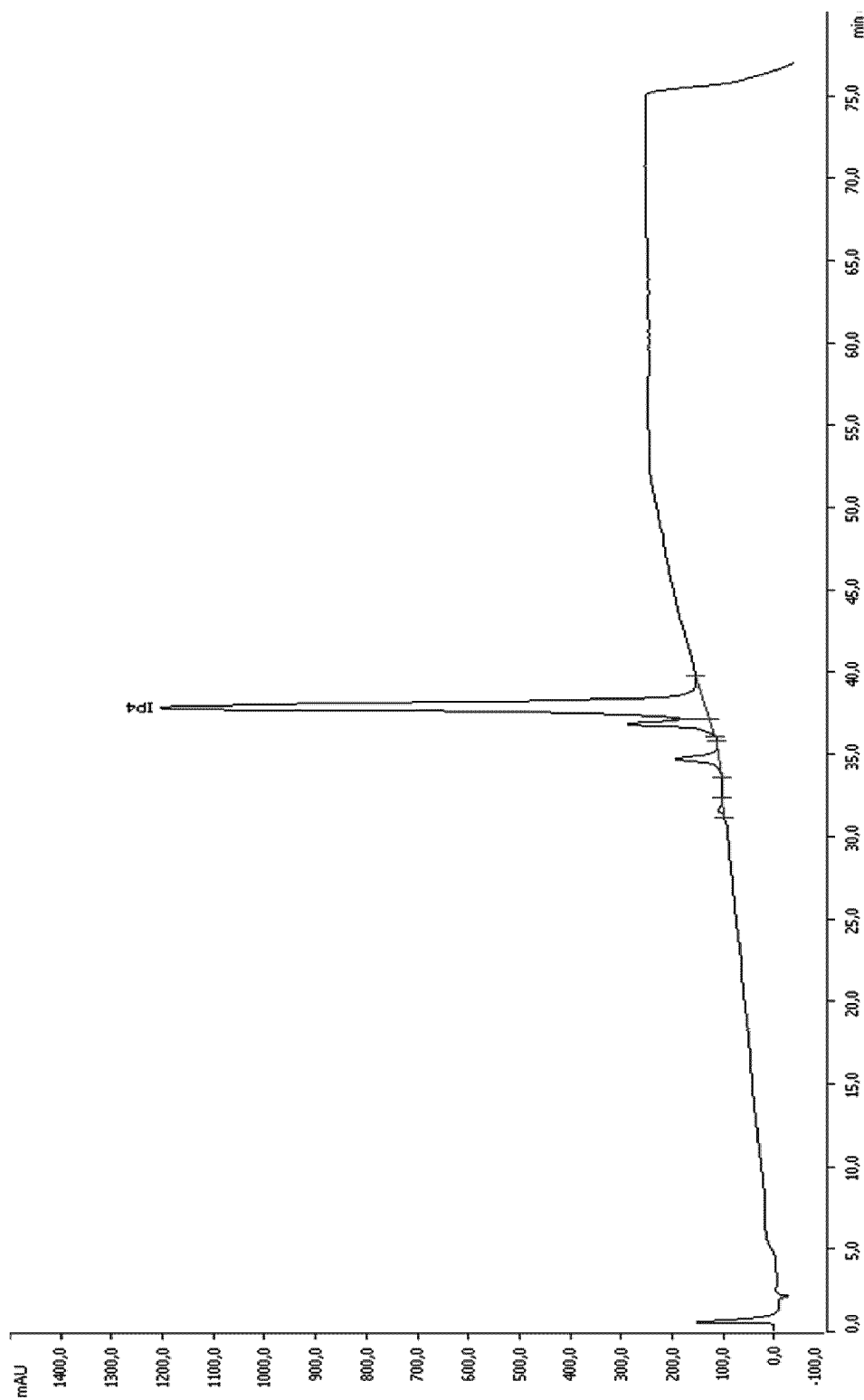
FIG. 19 shows an IC chromatogram of $Na_4IP_4$ salt. The figure shows an $IP_4$ peak at RT 37.83 min. The $IP_4$ is 85.12% (w/w) pure.

Ion exchange chromatography: The spectroscopic data was further confirmed by ion-exchange chromatography in which the retention time of the phytic acid peak in Na$_6$IP$_6$ was compared to that of the phytic acid peak in an analytical reference standard under the same chromatographic conditions. See FIG. 18.

Polymorphism: Na$_6$IP$_6$ was isolated as an amorphous solid material. Several attempts to isolate Na$_6$IP$_6$ as a crystalline material were performed but did not reveal any evidence of a polymorph.

In conclusion, the structural elucidation studies carried out on Na$_6$IP$_6$ together with the synthetic route used for its preparation are consistent with and fully support the proposed structure.

Example 16

Compounding and Formulation of Na$_6$IP$_6$ Prepared from Recrystallized and Non-Recrystallized Na$_{12}$IP$_6$ Step 1—Compounding (preparation of solution): Components (e.g., Na$_6$IP$_6$ obtained from recrystallized Na$_{12}$IP$_6$ or non-recrystallized Na$_{12}$IP$_6$) were diluted with water for injection in a dedicated 400L mixing bag equipped with a magnetic stirrer. The batch composition was detailed in the table below. The pH was adjusted to 6.0 0.4 with a 6.0M NaOH solution.

TABLE 13

Batch composition

| Name of Substance | Concentration | Quantity per vial | Quantity per batch |
|---|---|---|---|
| Na$_6$IP$_6$ | 3% | 300 mg | 12600 g |
| Sodium chloride | 0.9% | 90 mg | 3780 g |
| NaOH* | q.s to pH 5.6-6.4 | | |

TABLE 13-continued

Batch composition

| Name of Substance | Concentration | Quantity per vial | Quantity per batch |
|---|---|---|---|
| Water for injection | To 100% | To 10 mL | 420 L |

*6.0M NaOH solution (allows a faster adjustment with a minimum impact on drug product volume)

Step 2—Filtration: The final bulk solution was filtered through a single-use filtration transfer equipped with a 0.2 μm PES filter.

Step 3—Solution collection: The filtered solution was collected into a 400 L feeder bag.

Step 4—Filling process: A filling machine feeder bag was used. The filtered final bulk was filled into glass vials type I.

Step 5—Stoppering and capping: Vials were stoppered, and caps were placed on the stoppered vials with a capping machine.

Step 6—Visual inspection and testing: 100% of the vials were visually inspected and the drug product was analyzed according to the established specifications Step 7—Storage: Vials were bulk packed into secondary packaging and transferred to warehouse for storage at 2-8° C. until shipment.

Example 17

Stability of Pharmaceutical Compositions

A $Na_6IP_6$ aqueous pharmaceutical composition having the ingredients and content according to the protocol described in Example 16 (i.e., Table 13) was prepared. The recrystallized $Na_6IP_6$ salt used for preparing the solution was obtained and characterized according to the protocol described in Example 7.

Aliquots of the $Na_6IP_6$ aqueous pharmaceutical composition were stored at: (i) −20° C., and (ii) 5° C. for 12 months, and (iii) at 25° C. and 60% relative humidity (RH) for 6 months. The stability of the items (i) and (ii) aliquots was assayed at the beginning and at 3, 6, 9, and 12 months. The stability of the item (iii) aliquots was assayed at the beginning and at 1, 3, and 6 months. The ion chromatography protocols described above were used for assessing stability. All the $Na_6IP_6$ aqueous pharmaceutical compositions were found to be stable and within specifications at all temperatures and RH conditions tried. See Tables 14 and 15. These results show that the $Na_6IP_6$ aqueous pharmaceutical compositions are stable at room temperature.

TABLE 14

Stability of liquid compositions at −20° C. and 5° C.

| | | Stability | | | | |
|---|---|---|---|---|---|---|
| Temperature | RH | Initial | 3 months | 6 months | 9 months | 12 months |
| −20° C. | — | 100.0% | 98.5% | 98.3% | 98.9% | 98.0% |
| 5° C. | — | 100.0% | 98.8% | 98.4% | 98.9% | 98.2% |

TABLE 15

Stability of liquid compositions at 25° C. and 60% RH

| | | Stability | | | |
|---|---|---|---|---|---|
| Temperature | RH | Initial | 1 month | 3 months | 6 months |
| 25° C. | 60% | 100.0% | 97.5% | 97.8% | 96.0% |

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the person skilled in the art in light of the teachings and guidance. All the cited references are incorporated to the description in their entireties.

The breadth and scope of the present invention should not be limited to any of the above-described examples or aspects but should be defined only in accordance with the following claims and its equivalents.

The invention claimed is:
1. A process for preparing a purified inositol phosphate (IP) salt, wherein the process comprises
 (A) an ion removal step comprising:
  (a) dissolving an IP salt in water to obtain an IP solution;
  (b) contacting the IP solution of step (a) with an ion exchange medium, thereby yielding an ion exchanged IP solution;
  (c) concentrating the ion exchanged IP solution of step (b) to obtain an IP syrup containing a soluble IP salt; and,
  (d) separating the soluble IP salt of step (c) from the IP syrup in the presence of an alkoxide; and,
 (B) a purification step comprising:
  (i) dissolving the soluble IP salt separated in step (d) in water to obtain an IP solution;
  (ii) converting the IP solution of step (i) to an IP suspension;
  (iii) washing the IP suspension of step (ii) with an alcohol solution to obtain an IP solid; and,

(iv) drying the IP solid of step (iii) to obtain the purified IP salt.

2. The process of claim 1, wherein the ion exchange medium of step (b) is an ion exchange chromatography, batch process, or pH adjustment system.

3. The process of claim 1, wherein the concentrating of step (c) is conducted by distilling the ion exchanged IP solution of step (b) at a temperature of about 25° C. to about 55° C.

4. The process of claim 3, wherein the distilling is for about 1 hour to about 16 hours.

5. The process of claim 1, wherein the water content of the IP syrup of step (c) is between about 30% and about 60% (w/w).

6. The process of claim 1, wherein the alkoxide of step (d) is a $C_1$-$C_4$ alkoxide.

7. The process of claim 5, wherein the $C_1$-$C_4$ alkoxide is $CH_3NaO$, $CH_3CH_2NaO$, $CH_3KO$, $CH_3CH_2KO$, or a combination thereof.

8. The process of claim 1, wherein the separating of step (d) is conducted between about pH 4.0 and about pH 5.5.

9. The process of claim 1, further comprising a step (e) following step (d) wherein step (e) comprises spray drying the soluble IP salt of step (d).

10. The process of claim 1, wherein the soluble IP salt and water of step (i) are mixed in about 1:1 to about 1:30 weight ratio.

11. The process of claim 1, wherein the IP solution of step (i) is heated at a temperature of about 45° C. to about 50° C. for about 0.2 hours to about 4 hours.

12. The process of claim 1, wherein the IP solution of step (i) is seeded with crystals of a soluble IP salt previously purified, wherein the soluble IP salt previously purified represents about 0.01% to about 0.4% (w/w) of the soluble IP salt of step (i).

13. The process of claim 1, wherein the alcohol solution in step (iii) comprises a $C_1$-$C_4$ alcohol.

14. The process of claim 13 wherein the $C_1$-$C_4$ alcohol is ethanol.

15. The process of claim 1, wherein the drying of the IP solid of step (iv) is conducted
(d1) at a temperature of about 20° C. to about 50° C.;
(d2) for about 25 minutes to about 120 minutes;
(d3) at a pressure of about 0.01 mbar to about 1 mbar;
(d4) under vacuum; or,
(d5) applying a combination of $(d_1)$-$(d_4)$.

16. The process of claim 1, wherein the purified IP salt of step (iv) is inositol hexaphosphate.

17. The process of claim 16, wherein the inositol hexaphosphate is myo-inositol hexaphosphate.

18. The process of claim 1, wherein the purified IP salt of step (iv) contains at least one monovalent cation selected from the group consisting of sodium, potassium, ammonium, or a combination thereof.

19. The process of claim 1, wherein the purified IP salt of step (iv) is a hexasodium salt.

20. The process of claim 1, wherein the purified IP salt of step (iv) is $Na_6IP_6$.

21. A process for preparing a purified inositol phosphate (IP) salt, wherein the process comprises an ion removal step comprising:
(a) dissolving an IP salt in water to obtain an IP solution;
(b) contacting the IP solution of step (a) with an ion exchange medium, thereby yielding an ion exchanged IP solution;
(c) concentrating the ion exchanged IP solution of step (b) to obtain an IP syrup containing a soluble IP salt; and,
(d) separating the soluble IP salt of step (c) from the IP syrup in the presence of an alkoxide.

22. The process of claim 21, wherein the ion exchange medium of step (b) is an ion exchange chromatography, batch process, or pH adjustment system.

23. The process of claim 21, wherein the concentrating of step (c) is conducted by distilling the ion exchanged IP solution of step (b) at a temperature of about 25° C. to about 55° C.

24. The process of claim 23, wherein the distilling is for about 1 hour to about 16 hours.

25. The process of claim 21, wherein the water content of the IP syrup of step (c) is between about 30% and about 60% (w/w).

26. The process of claim 21, wherein the alkoxide of step (d) is a $C_1$-$C_4$ alkoxide.

27. The process of claim 26, wherein the $C_1$-$C_4$ alkoxide is $CH_3NaO$, $CH_3CH_2NaO$, $CH_3KO$, $CH_3CH_2KO$, or a combination thereof.

28. The process of claim 21, wherein the separating of step (d) is conducted between about pH 4.0 and about pH 5.5.

29. The process of claim 21, further comprising a step (e) following step (d) wherein step (e) comprises spray drying the soluble IP salt of step (d).

30. The process of claim 21, wherein the purified IP is $Na_6IP_6$.

* * * * *